US008105775B2

(12) United States Patent
Kornman et al.

(10) Patent No.: US 8,105,775 B2
(45) Date of Patent: Jan. 31, 2012

(54) IL-1 GENE CLUSTER AND ASSOCIATED INFLAMMATORY POLYMORPHISMS AND HAPLOTYPES

(75) Inventors: Kenneth S. Kornman, Newton, MA (US); Kenneth Huttner, Chestnut Hill, MA (US); John Rogus, North Andover, MA (US)

(73) Assignee: Interleukin Genetics, Inc., Waltham, MA (US)

( * ) Notice: Subject to any disclaimer, the term of this patent is extended or adjusted under 35 U.S.C. 154(b) by 243 days.

(21) Appl. No.: 12/084,181

(22) PCT Filed: Oct. 25, 2006

(86) PCT No.: PCT/US2006/041847
§ 371 (c)(1),
(2), (4) Date: Jun. 8, 2009

(87) PCT Pub. No.: WO2007/050794
PCT Pub. Date: May 3, 2007

(65) Prior Publication Data
US 2009/0298063 A1     Dec. 3, 2009

Related U.S. Application Data

(60) Provisional application No. 60/729,953, filed on Oct. 25, 2005.

(51) Int. Cl.
*C12Q 1/68* (2006.01)
(52) U.S. Cl. ........................................ 435/6.1
(58) Field of Classification Search ............... None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,833,080 A | 5/1989 | Brent et al. | |
| 4,968,607 A | 11/1990 | Dower et al. | |
| 4,998,617 A | 3/1991 | Ladd, Jr. et al. | |
| 5,459,039 A | 10/1995 | Modrich et al. | |
| 5,596,826 A | 1/1997 | Barden | |
| 5,686,246 A | 11/1997 | Kornman et al. | |
| 6,140,047 A | 10/2000 | Duff et al. | |
| 6,210,877 B1 | 4/2001 | Francis et al. | |
| 6,268,142 B1 | 7/2001 | Duff et al. | |
| 6,524,795 B1 * | 2/2003 | Francis et al. | 435/6 |
| 6,558,905 B1 | 5/2003 | van Dijk et al. | |
| 6,706,478 B2 | 3/2004 | Duff et al. | |
| 6,730,476 B1 | 5/2004 | Duff et al. | |
| 6,733,967 B1 | 5/2004 | Kornman et al. | |
| 6,746,839 B1 | 6/2004 | Duff et al. | |
| 2002/0182612 A1 | 12/2002 | Duff et al. | |
| 2003/0235890 A1 | 12/2003 | Wyllie et al. | |
| 2004/0171038 A1 | 9/2004 | Nicklin et al. | |
| 2005/0064453 A1 | 3/2005 | Duff et al. | |
| 2005/0084882 A1 | 4/2005 | Kornman et al. | |
| 2005/0282198 A1 | 12/2005 | Duff et al. | |
| 2006/0252055 A1 | 11/2006 | Francis et al. | |
| 2007/0264645 A1 | 11/2007 | Kornman et al. | |
| 2008/0254476 A1 | 10/2008 | Kornman et al. | |
| 2008/0254477 A1 | 10/2008 | Kornman et al. | |
| 2009/0098141 A1 | 4/2009 | Kornman et al. | |

FOREIGN PATENT DOCUMENTS

| | | |
|---|---|---|
| WO | WO-9416101 A2 | 7/1994 |
| WO | WO-9815653 A1 | 4/1998 |
| WO | WO-9840517 A1 | 9/1998 |
| WO | WO-9854359 A1 | 12/1998 |
| WO | WO-0072015 A2 | 11/2000 |
| WO | WO-02103031 A2 | 12/2002 |
| WO | WO-03044176 A2 | 5/2003 |
| WO | WO-03064600 A2 | 8/2003 |
| WO | WO-03106652 A2 | 12/2003 |
| WO | WO-2005108619 A2 | 11/2005 |
| WO | WO-2007050794 A2 | 5/2007 |
| WO | WO-2008060627 A2 | 5/2008 |

OTHER PUBLICATIONS

U.S. Appl. No. 09/617,720, filed Jul. 17, 2000, Nicklin, Martin.
Altschul et al., "Gapped BLAST and PSI-BLAST: a new generation of protein database search programs", *Nucl. Acids Res.*, 25(17):3389-3402 (1997).
Armitage et al., "Low Prevalence of a Periodontitis-Associated Interleukin-1 Composite Genotype in Individuals of Chinese Heritage", *J. Periodontology*, 7(2):164-171 (2000).
Bailly et al., "Genetic polymorphism of human interleukin-1α", *Eur. J. Immunol.*, 23:1240-1245 (1993). Barton et al., "A tissue specific IL-1 receptor antagonist homolog from the IL-1 cluster lacks IL-1, IL-1ra, IL-18 and IL-18 antagonist activities", *Eur. J. Immunol.*, 30:3299-3308 (2000).
Bazan et al., "A newly defined interleukin-1?", *Nature*, 379:591 (1996).
Berger et al., "C-reactive protein levels are influenced by common IL-1 gene variations", *Cytokine*, 17(4):171-174 (2002).
Born et al., "Cloning of a Novel Receptor Subunit, AcPL, Required for Interleukin-18 Signaling", *J. Biol. Chem.*, 273(45):29445-29450 (1998).
Busfield et al., "Identification and Gene Organization of Three Novel Members of the IL-1 Family on Human Chromosome 2", *Genomics*, 66:213-216 (2000).
Clark et al., "Genomic sequence for human prointerleukin 1 beta: possible evolution from a reverse transcribed prointerleukin 1 alpha gene", *Nucl. Acids Res.*, 14(20):7897-7914 (1986).

(Continued)

*Primary Examiner* — Kenneth R. Horlick
*Assistant Examiner* — David Thomas
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The invention provides methods and compositions relating to identification and use of genetic information from the IL-I gene cluster—including the structure and organization of novel IL-I-like genes found within the IL-I locus as well as polymorphisms and associated haplotypes within these genes. The invention thereby expands the repertoire of useful genetic information available from the IL-I locus—which contains the previously-identified IL-1α, EL-1β and IL-IRN genes, for predicting IL-I associated phenotypes (e.g. increased or decreased risks of inflammatory disease) and for treating IL-I haplotype associated inflammatory phenotypes.

2 Claims, 44 Drawing Sheets

OTHER PUBLICATIONS

Clay et al., "Novel interleukin-1 receptor antagonist exon polymorphisms and their use in allele-specific mRNA assessment", *Hum Genet.*, 97:723-726 (1996).

Cox et al., "An Analysis of Linkage Disequilibrium in the Interleukin-1 Gene Cluster, Using a Novel Grouping Method for Multiallelic Markers", *Am. J. Hum. Genet.*, 62: 1180-1188 (1998).

Cox et al., "Cytokines as Genetic Modifying Factors in Immune and Inflammatory Diseases", *J. Ped. Endocrinol. Metab.*, 9:(Suppl. 1):129-132 (1996).

di Giovine et al., "Detection and population analysis of IL-1 and TNF gene polymorphisms", in *Cytokine Molecular Biology*, Oxford University Press, Oxford, UK Ch. 2, pp. 21-46 (2000).

Ewing et al., "Base-Calling of Automated Sequencer Traces Using *Phred.* II. Error Probabilities", *Genome Res.*, 8(3):186-194 (1998).

Francis et al., "Interleukin-1 Receptor Antagonist Gene Polymorphism and Coronary Artery Disease", *Circulation*, 99:861-866 (1999).

Furutani et al., "Complete nucleotide sequence of the gene for human interleukin 1 alpha", *Nucl. Acids Res.*, 14(8):3167-3179 (1986).

GenBank Accession No. NM_012455 dated Mar. 5, 2010.

GenBank Accession No. X04500 dated Oct. 23, 2008.

GenBank Accession No. X64532 dated Nov. 14, 2006.

GenBank Accession No. XM_002217 dated Aug. 1, 2002.

GenBank Accession No. XM_041373 dated Oct. 16, 2001.

GenBank Accession No. X03833 dated Oct. 23, 2008.

Greenfeder et al., "Molecular Cloning and Characterization of a Second Subunit of the Interleukin 1 Receptor Complex", *J. Biol. Chem.*, 270(23):13757-13765 (1997).

Guzman et al., "Association Between Interleukin-1 Genotype and Periodontal Disease in a Diabetic Population", *J. Periodontology*, 74:1183-1190 (2003).

Halushka et al., "Patterns of single-nucleotide polymorphisms in candidate genes for blood-pressure homeostasis", *Nature*, 22:239-247 (1999).

Heguy et al., "Amino Acids Conserved in Interleukin-1 Receptors (IL-1Rs) and the *Drosophila* Toll Protein Are Essential for IL-1R Signal Transduction" *J. Biol. Chem.*, 267(4):2605-2609 (1992).

Hermann et al., "Association between interleukin-6 polymorphism and age-at-onset of type 1 diabetes. Epistatic influences of the tumor necrosis factor-α and interleukin-1β polymorphisms", *Eur. Cytokine Net.*, 16(4):277-281 (2005).

Hirschhorn et al., "A comprehensive review of genetic association studies", *Genet. Med.*, 4(2):45-61 (2002).

Iacoviello et al., "Polymorphisms of the Interleukin-1β Gene Affect the Risk of Myocardial Infarction and Ischemic Stroke at Young Age and the Response of Mononuclear Cells to Stimulation in Vitro", *Arterioscler. Thromb. Vasc. Biol.*, 25:222-227 (2005).

International Search Report for PCT/US2003/02232 mailed Sep. 14, 2005.

International Search Report for PCT/US2006/041847 mailed Aug. 28, 2007.

International Search Report for PCT/US2007/024107 mailed Aug. 12, 2008.

Kornman et al., "Interleukin-1 genotypes and the association between periodontitis and cardiovascular disease", *J. Periodontal Res.*, 34:353-357 (1999).

Kumur et al., "Identification and Initial Characterization of Four Novel Members of the Interleukin-1 Family", *J. Biol. Chem.*, 275(14):10308-10314 (2000).

Lander et al., "Initial sequencing and analysis of the human genome", *Nature*, 409:860-921(2001).

Langdahl et al., "Osteoporotic Fractures Are Associated with an 86-Base Pair Repeat Polymorphism in the Interleukin-1-Receptor Antagonist Gene But Not with Polymorphisms in the Interleukin-1β Gene", *J. Bone Mineral Res.*, 15(3):402-414 (2000).

Latkovskis et al., "C-reactive protein levels and common polymorphisms of the interleukin-1 gene cluster and interleukin-6 gene in patients with coronary heart disease", *Eur. J. Immunogenetics*, 31:207-213 (2004).

Lin et al., "Cloning and Characterization of IL-1HY2, a Novel Interleukin-1 Family Member", *J. Biol. Chem.*, 276(23):20597-20602 (2001).

Lucentini et al., "Gene Association Studies Typically Wrong", *Scientist*, 18(24):20 (2004).

Mansfield et al., "Novel Genetic Association Between Ulcerative Colitis and the Anti-inflammatory Cytokine Interleukin-1 Receptor Antagonist", *Gastroenterology*, 106:637-642 (1994).

Minton et al., "Clearance of Hepatitis C Virus Is Not Associated With Single Nucleotide Polymorphisms in the IL-1, -6, or -10 Genes", *Human Immunology*, 66:127-132 (2005).

Mulero et al., "IL1HY1: A Novel Interleukin-1 Receptor Antagonist Gene", *Biochem. Biophys Res. Commun.*, 263(3):702-706 (1999).

Muraki et al., "Polymorphisms of IL-1β Gene in Japanese Patients with Sjogren's Syndrome and Systemic Lupus Erythematosus", *J. Rheumatol.*, 31:720-725 (2004).

Murphy et al., "Rate of cognitive decline in AD is accelerated by the interleukin-1α -889 *1 allele", *Neurology*, 56:1595-1597 (2001).

Nicklin et al., "A Physical Map of the Region Encompassing the Human Interleukin-1α, Interleukin-1β, and Interleukin-1 Receptor Antgonist Genes", *Genomics*, 19:382-384, 1994.

Nolan et al., "The Human Interleukin 18 Gene *IL* 18 Maps to 11q22.2-q22.3, Closely Linked to the DRD2 Gene Locus and Distinct from Mapped IDDM Loci", *Genomics*, 51:161-163 (1998).

Nothwang et al., "Molecular Cloning of the Interleukin-1 Gene Cluster: Construction of an Integrated YAC/PAC Contig and a Partial Transcriptional Map in the Region of Chromosome 2q13", *Genomics*, 41:370-378 (1997).

Pan et al., "Forced Expression of Murine IL-17E Induces Growth Retardation, Jaundice, a Th2-Biased Response, and Multiorgan Inflammation in Mice", *J. Immunol.*, 167(11):6559-6567 (2001).

Priestle et al., "Crystallographic refinement of interleukin 1β at 2.0 A resolution", *Proc. Natl. Acad. Sci. U.S.A.*, 86:9667-9971 (1989).

Rosenmann et al., "Lack of association of interleukin-1beta polymorphism with Alzheimer's disease in the Jewish population", *Neuroscience Lett.*, 363:131-133 (2004).

Ross, R., "The pathogenesis of atherosclerosis: a perspective for the 1990s", *Nature*, 362:801-809 (1993).

Schaid, D. J., "Relative Efficiency of Ambiguous vs. Directly Measured Haplotype Frequencies", *Genetic Epidemiology*, 23(4):426-443 (2002).

Sims et al., "A new nomenclature for IL-1-family genes", *Trends Immunol.*, 22:536-537 (2001).

Sims et al., "Interleukin 1 signaling occurs exclusively via the type I receptor", *Proc. Natl. Acad. Sci. U.S.A.*, 90:6155-6159 (1993).

Smith et al., "Four New Members Expand the Interleukin-1 Superfamily", *J. Biol. Chem.*, 275(2):1169-1175 (2000).

Torigoe et al., "Purification and Characterization of the Human Interleukin-18 Receptor", *J. Biol. Chem.*, 272(41):25737-25742 (1997).

Vigers et al., "X-ray Structure of Interleukin-1 Receptor Antagonist at 2.0-A resolution", *J Biol. Chem.*, 269(17):12874-12879 (1994).

Wesche et al., "The Interleukin-1 Receptor Accessory Protein (IL-1RAcP) is Essential for IL-1-induced Activation of Interleukin-1 Receptor-associated Kinase (IRAK) and Stress-activated Protein Kinases (SAP kinases)", *J. Biol Chem.*, 272(12):7727-7731 (1997).

Zmuda et al., "The search for human osteoporosis genes", *J. Musculoskelet Neuronal Interaction*, 6(1):3-15 (2006).

* cited by examiner

| Linkage Disequilibrium (D') Values and their Statistical Significance among representative SNPs of the IL-1 Gene Cluster | | | | | | | | | | | | | | | | | | | | |
|---|---|---|---|---|---|---|---|---|---|---|---|---|---|---|---|---|---|---|---|
| SNPs | 1 | 2 | 3 | 4 | 5 | 6 | 7 | 8 | 9 | 10 | 11 | 12 | 13 | 14 | 15 | 16 | 17 | 18 | 19 | 20 |
| 1 | | 1 | 1 | 1 | 1 | 1 | 1 | 0.8287 | 1 | 0.9397 | 0.3447 | 0.3409 | 0.3718 | 0.0082 | 0.8955 | 0.875 | 0.6448 | 0.5615 | 0.5208 | 0.6402 |
| 2 | 1 | | 1 | 1 | 1 | 1 | 1 | 1 | 0.8379 | 0.5977 | 0.2729 | 0.2349 | 0.0107 | 0.6073 | 0.689 | 0.8439 | 0.3754 | 0.387 | 0.352 | 0.3954 |
| 3 | 1 | 1 | | 1 | 1 | 1 | 1 | 1 | 1 | 0.9424 | 0.3371 | 0.3332 | 0.3803 | 0.0365 | 0.8876 | 0.8743 | 0.6495 | 0.5709 | 0.5259 | 0.6374 |
| 4 | 1 | 1 | 1 | | 1 | 1 | 1 | 1 | 1 | 0.9398 | 0.3485 | 0.3445 | 0.402 | 0.0692 | 0.8781 | 0.8733 | 0.6499 | 0.5707 | 0.5255 | 0.6537 |
| 5 | 1 | 1 | 1 | 1 | | 1 | 1 | 1 | 1 | 0.9397 | 0.3447 | 0.3409 | 0.3718 | 0.0082 | 0.8955 | 0.875 | 0.6448 | 0.5615 | 0.5208 | 0.6402 |
| 6 | 1 | 1 | 1 | 1 | 1 | | 1 | 0.7653 | 0.7782 | 0.7469 | 0.2809 | 0.2869 | 0.6504 | 0.5214 | 0.7485 | 1 | 0.4313 | 0.4276 | 0.3958 | 0.1879 |
| 7 | 1 | 1 | 1 | 1 | 1 | 1 | | 0.8367 | 0.8451 | 0.5952 | 0.3264 | 0.2928 | 0.0487 | 0.6087 | 0.7019 | 0.8408 | 0.2806 | 0.2919 | 0.2641 | 0.4135 |
| 8 | 1 | 1 | 1 | 1 | 1 | 1 | 1 | | 1 | 1 | 0.7308 | 0.7301 | 0.8639 | 0.9104 | 0.8654 | 0.7648 | 0.7505 | 0.7574 | 0.6502 | 0.5592 |
| 9 | 1 | 1 | 1 | 1 | 1 | 1 | 1 | 1 | | 1 | 0.7405 | 0.7399 | 0.8683 | 0.9148 | 0.8726 | 0.7748 | 0.6434 | 0.6523 | 0.5668 | 0.5781 |
| 10 | 1 | 0.999 | 1 | 1 | 1 | 1 | 0.92 | 1 | 0.999 | | 0.7326 | 0.7343 | 0.6217 | 0.8323 | 0.922 | 1 | 0.6817 | 0.6835 | 0.679 | 0.5739 |
| 11 | 1 | 0.831 | 1 | 1 | 1 | 0.917 | 0.893 | 1 | 1 | 1 | | 1 | 0.9788 | 1 | 1 | 1 | 0.634 | 0.5435 | 0.617 | 0.6942 |
| 12 | 1 | 0.754 | 1 | 1 | 1 | 0.93 | 0.201 | 0.999 | 1 | 0.997 | 1 | | 0.9791 | 1 | 1 | 1 | 0.6348 | 0.5435 | 0.618 | 0.6746 |
| 13 | 1 | 0.071 | 1 | 1 | 0.013 | 1 | 1 | 1 | 1 | 1 | 1 | 1 | | 1 | 1 | 1 | 0.6298 | 0.5163 | 0.5901 | 0.6244 |
| 14 | 0.023 | 1 | 0.181 | 0.378 | 1 | 1 | 1 | 1 | 1 | 1 | 1 | 1 | 1 | | 1 | 1 | 0.6906 | 0.6583 | 0.6831 | 0.2527 |
| 15 | 0.999 | 1 | 1 | 1 | 1 | 1 | 0.981 | 0.93 | 0.913 | 0.99 | 0.987 | 0.995 | 1 | 1 | | 1 | 0.8597 | 0.8637 | 1 | 0.6825 |
| 16 | 1 | 0.975 | 1 | 1 | 1 | 0.998 | 0.866 | 0.999 | 0.997 | 1 | 0.998 | 0.999 | 0.982 | 1 | 0.98 | | 1 | 1 | 1 | 1 |
| 17 | 0.998 | 0.939 | 0.997 | 0.994 | 0.996 | 1 | 0.88 | 0.999 | 0.994 | 1 | 0.997 | 0.99 | 0.993 | 1 | 1 | 0.988 | | 1 | 1 | 0.8782 |
| 18 | 0.983 | 0.951 | 0.996 | 0.995 | 0.984 | 1 | 0.83 | 1 | 0.995 | 0.999 | 1 | 1 | 0.973 | 1 | 1 | 0.992 | 0.9831 | | 1 | 0.8782 |
| 19 | 0.99 | 0.931 | 0.992 | 0.98 | 0.986 | 0.871 | 0.83 | 0.995 | 0.995 | 1 | 0.999 | 0.99 | 0.996 | 1 | 1 | 0.986 | 1 | 1 | | 0.848 |
| 20 | 1 | 0.985 | 1 | 1 | 1 | 1 | 0.996 | 1 | 1 | 1 | 1 | 1 | 1 | 0.984 | 1 | 1 | 1 | 1 | 1 | |

Fig. 2A

|    |       |       |       |       |       |       |       |       |       |       |       |       |       |       |       |       |       |       |       |
|----|-------|-------|-------|-------|-------|-------|-------|-------|-------|-------|-------|-------|-------|-------|-------|-------|-------|-------|-------|
| 21 | 0.705 | 0.686 | 0.749 | 0.755 | 0.743 | 0.212 | 0.677 | 0.321 | 0.368 | 0.001 | 0.999 | 0.999 | 0.995 | 0.655 | 0.933 | 0.093 | 0.946 | 0.888 | 0.883 | 1 |
| 22 | 0.755 | 0.756 | 0.598 | 0.746 | 0.714 | 0.289 | 0.804 | 0.473 | 0.5   | 0.105 | 0.998 | 0.999 | 0.997 | 0.56  | 0.953 | 0.077 | 0.943 | 0.897 | 0.91 | 1 |
| 23 | 1     | 0.922 |       | 1     | 1     | 0.881 | 0.956 | 0.996 | 1     | 0.999 | 0.998 | 0.999 | 0.995 | 0.647 | 0.974 | 0.998 | 1     | 1     | 1 | 1 |
| 24 | 1     | 0.96  |       |       |       | 0.911 | 0.991 | 0.998 | 1     | 1     | 0.999 | 1     | 1     | 0.782 | 0.997 | 1     | 1     | 1     | 1 | 1 |
| 25 | 0.233 | 0.003 | 0.091 | 0.095 | 0.216 | 0.085 | 0.028 | 0.483 | 0.406 | 0.455 | 1     | 1     | 1     | 0.999 | 0.159 | 1     | 0.79  | 0.851 | 0.42 | 0.946 |
| 26 | 0.827 | 0.999 | 0.799 | 0.809 | 0.818 | 0.978 | 1     | 0.999 | 0.997 | 0.587 | 1     | 1     | 0.997 | 0.664 | 1     | 1     | 0.882 | 0.752 | 0.892 | 0.992 |
| 27 | 0.662 | 0.992 | 0.773 | 0.8   | 0.632 | 0.997 | 0.985 | 0.954 | 0.96  | 1     | 0.995 | 1     | 0.993 | 1     | 0.925 | 0.019 |       |       |       | 1 |
| 28 | 1     | 0.928 |       | 0.999 | 1     | 0.828 | 0.984 | 1     | 1     | 0.92  | 0.998 | 1     | 1     | 1     | 1     | 0.985 | 0.993 | 0.979 | 0.993 | 1 |
| 29 | 0.999 | 0.939 | 0.998 | 0.999 | 0.997 | 0.81  | 0.991 | 1     | 1     | 0.935 | 1     | 1     | 1     | 0.999 | 1     | 0.974 | 0.993 | 0.986 | 0.999 | 1 |
| 30 | 0.998 | 0.944 | 0.996 | 0.999 | 1     | 0.78  | 0.986 | 1     | 1     | 0.919 | 1     | 1     | 1     | 1     | 1     | 0.974 | 0.998 | 0.992 | 0.998 | 1 |
| 31 | 1     | 0.96  | 0.997 | 1     | 1     | 0.817 | 0.989 | 1     | 1     | 0.845 | 1     | 1     | 1     | 1     | 1     | 0.985 | 0.994 | 0.985 | 0.997 | 1 |
| 32 | 0.997 | 0.935 | 0.996 | 0.995 | 0.994 | 0.767 | 0.986 | 1     | 1     | 0.921 | 1     | 1     | 1     | 0.999 | 1     | 0.98  | 0.991 | 0.991 | 0.989 | 1 |
| 33 | 0.996 | 0.931 | 0.998 | 0.998 | 0.999 | 0.698 | 0.981 | 1     | 1     | 0.839 | 1     | 1     | 1     | 1     | 1     | 0.982 | 0.997 | 0.985 | 0.995 | 1 |
| 34 | 0.997 | 0.959 | 0.997 | 0.993 | 0.998 | 0.61  | 0.995 | 1     | 1     | 0.727 | 1     | 1     | 1     | 1     | 1     | 0.981 | 0.988 | 0.979 | 0.988 | 1 |
| 35 | 0.997 | 0.969 | 0.993 | 0.993 | 0.993 | 0.44  | 0.993 | 1     | 1     | 0.703 | 1     | 1     | 1     | 1     | 1     | 0.984 | 0.992 | 0.973 | 0.987 | 1 |
| 36 | 1     | 0.994 | 0.999 | 0.999 | 0.999 | 0.253 | 0.997 | 1     | 1     | 0.965 | 1     | 1     | 1     | 0.996 | 0.998 | 0.986 |       |       |       | 1 |
| 37 | 0.426 | 0.638 | 0.475 | 0.585 | 0.441 | 0.871 | 0.59  | 0.355 | 0.378 | 0.914 | 0.971 | 0.975 | 0.86  | 0.688 | 0.185 | 1     | 0.88  | 0.896 | 0.952 | 0.761 |
| 38 | 0.999 | 0.835 | 0.999 | 0.998 | 0.996 | 0.79  | 0.944 | 0.995 | 0.998 | 0.981 | 0.987 | 0.99  | 0.88  | 0.381 | 0.996 | 0.997 | 1     | 1     | 1 | 1 |
| 39 | 0.996 | 0.84  | 0.999 | 0.999 | 0.998 | 0.799 | 0.944 | 0.994 | 0.998 | 0.999 | 0.999 | 0.99  | 0.88  | 0.064 | 0.991 | 0.999 | 1     | 1     | 1 | 1 |

Note: Numbers above the diagonal represent 1 – p (where p = significance of the Chi-square) values. Numbers below the diagonal represent D' values.

Fig. 2A (Cont'd)

| Linkage Disequilibrium (D') Values and their Statistical Significance among representative SNPs of the IL-1 Gene Cluster | | | | | | | | | | | | | | | | | | | |
|---|---|---|---|---|---|---|---|---|---|---|---|---|---|---|---|---|---|---|---|
| SNPs | 21 | 22 | 23 | 24 | 25 | 26 | 27 | 28 | 29 | 30 | 31 | 32 | 33 | 34 | 35 | 36 | 37 | 38 | 39 |
| 1 | 0.3475 | 0.3584 | 0.6609 | 0.6957 | 0.0502 | 0.3759 | 0.2999 | 0.3054 | 0.2863 | 0.2829 | 0.2903 | 0.2642 | 0.2572 | 0.2592 | 0.2566 | 0.6685 | 0.0718 | 0.5657 | 0.5741 |
| 2 | 0.1404 | 0.1535 | 0.1861 | 0.2174 | 0.0036 | 0.3596 | 0.7162 | 0.3923 | 0.4023 | 0.407 | 0.4233 | 0.4148 | 0.3988 | 0.4351 | 0.4472 | 0.2321 | 0.1028 | 0.1222 | 0.1267 |
| 3 | 0.3619 | 0.3739 | 0.6622 | 0.6908 | 0.0197 | 0.3465 | 0.3617 | 0.2965 | 0.2767 | 0.2732 | 0.2806 | 0.2604 | 0.2509 | 0.2493 | 0.2416 | 0.6605 | 0.085 | 0.6043 | 0.6119 |
| 4 | 0.408 | 0.4218 | 0.6569 | 0.6861 | 0.0281 | 0.382 | 0.3914 | 0.3128 | 0.2914 | 0.2875 | 0.2955 | 0.2739 | 0.2636 | 0.2618 | 0.2488 | 0.6543 | 0.1009 | 0.5979 | 0.6057 |
| 5 | 0.3475 | 0.3584 | 0.6609 | 0.6957 | 0.0502 | 0.3759 | 0.2999 | 0.3054 | 0.2863 | 0.2829 | 0.2903 | 0.2642 | 0.2572 | 0.2592 | 0.2566 | 0.6685 | 0.0718 | 0.5657 | 0.5741 |
| 6 | 0.0694 | 0.1112 | 0.1442 | 0.1497 | 0.0139 | 0.4913 | 0.4567 | 0.2589 | 0.2418 | 0.2177 | 0.2436 | 0.2213 | 0.1768 | 0.1433 | 0.1038 | 0.0322 | 0.1767 | 0.1226 | 0.1324 |
| 7 | 0.1374 | 0.1604 | 0.2201 | 0.2481 | 0.0086 | 0.3901 | 0.6124 | 0.465 | 0.4734 | 0.4772 | 0.4802 | 0.4935 | 0.4695 | 0.4998 | 0.5054 | 0.2557 | 0.0879 | 0.1537 | 0.1574 |
| 8 | 0.0511 | 0.0695 | 0.3696 | 0.3911 | 0.077 | 0.3061 | 0.6649 | 0.8908 | 0.892 | 0.892 | 0.8929 | 0.8876 | 0.8873 | 0.8979 | 0.8992 | 0.3612 | 0.0597 | 0.2698 | 0.289 |
| 9 | 0.0534 | 0.075 | 0.396 | 0.4156 | 0.0657 | 0.3139 | 0.6442 | 0.8931 | 0.8945 | 0.8952 | 0.896 | 0.8912 | 0.8909 | 0.9007 | 0.901 | 0.3916 | 0.0693 | 0.2932 | 0.2992 |
| 10 | 0.0205 | 0.0579 | 0.415 | 0.4338 | 0.0961 | 0.2094 | 0.6239 | 0.3856 | 0.379 | 0.3409 | 0.3021 | 0.3439 | 0.2747 | 0.2158 | 0.2003 | 0.2157 | 0.2429 | 0.2128 | 0.273 |
| 11 | 1 | 1 | 0.5326 | 0.5824 | 0.5656 | 0.8676 | 0.8447 | 0.6411 | 0.6057 | 0.5956 | 0.5816 | 0.5655 | 0.5841 | 0.5798 | 0.5901 | 0.6923 | 0.6377 | 0.4049 | 0.4459 |
| 12 | 1 | 1 | 0.5356 | 0.5853 | 0.5683 | 0.8669 | 0.8465 | 0.6391 | 0.6035 | 0.5934 | 0.5793 | 0.5632 | 0.5818 | 0.5775 | 0.5878 | 0.6446 | 0.641 | 0.4048 | 0.4463 |
| 13 | 1 | 1 | 0.4785 | 0.5346 | 0.7152 | 0.769 | 0.8137 | 0.5437 | 0.5398 | 0.5398 | 0.5319 | 0.518 | 0.5518 | 0.558 | 0.5557 | 0.555 | 0.7765 | 0.2871 | 0.3202 |
| 14 | 0.1953 | 0.17 | 0.0947 | 0.1148 | 0.3034 | 0.1834 | 0.6785 | 0.6419 | 0.6038 | 0.574 | 0.551 | 0.5331 | 0.5651 | 0.5255 | 0.5597 | 0.1164 | 0.4983 | 0.0587 | 0.0052 |
| 15 | 0.1991 | 0.2258 | 0.2963 | 0.3271 | 0.0244 | 0.3521 | 0.6167 | 0.8784 | 0.8818 | 0.8822 | 0.8825 | 0.8747 | 0.8757 | 0.8944 | 0.8891 | 0.3124 | 0.0318 | 0.3114 | 0.2696 |
| 16 | 0.07 | 0.1141 | 1 | 1 | 0.8263 | 0.2531 | 0.0164 | 1 | 1 | 1 | 1 | 1 | 1 | 1 | 1 | 1 | 0.8726 | 1 | 1 |
| 17 | 0.6779 | 0.6775 | 0.8441 | 0.8514 | 0.2268 | 0.4428 | 0.6256 | 0.6544 | 0.6883 | 0.6924 | 0.6763 | 0.5932 | 0.628 | 0.6034 | 0.5978 | 0.3968 | 0.2508 | 0.4331 | 0.425 |
| 18 | 0.5665 | 0.5657 | 0.8181 | 0.8266 | 0.242 | 0.341 | 0.6467 | 0.5441 | 0.5887 | 0.5933 | 0.5729 | 0.5932 | 0.5391 | 0.51 | 0.5018 | 0.369 | 0.25 | 0.4156 | 0.4066 |
| 19 | 0.5499 | 0.5554 | 0.801 | 0.8095 | 0.0964 | 0.4239 | 0.6028 | 0.6144 | 0.6467 | 0.6467 | 0.6318 | 0.5628 | 0.5962 | 0.573 | 0.5669 | 0.3527 | 0.2907 | 0.3699 | 0.3689 |
| 20 | 1 | 1 | 1 | 1 | 0.1731 | 0.4708 | 0.7597 | 0.5849 | 0.6038 | 0.6115 | 0.6028 | 0.569 | 0.5868 | 0.5913 | 0.584 | 0.9344 | 0.1041 | 0.7722 | 0.8022 |

Fig. 2B

| | | | | | | | | | | | | | | | | | | |
|---|---|---|---|---|---|---|---|---|---|---|---|---|---|---|---|---|---|---|
| 21 | ▨ | 1 | 1 | 1 | 1 | 1 | 0.409 | 0.0342 | 1 | 0.1186 | 0.1863 | 0.1639 | 0.1804 | 0.1732 | 0.2058 | 0.2625 | 0.2301 | 0.6962 | 0.3323 | 0.8836 | 0.8756 |
| 22 | | ▨ | 1 | 1 | 1 | 1 | 0.3903 | 0.0305 | | 0.0936 | 0.1111 | 0.0704 | 0.0894 | 0.0771 | 0.1224 | 0.1837 | 0.1467 | 0.7023 | 0.3066 | 0.8853 | 0.8781 |
| 23 | 1 | 1 | ▨ | 1 | 1 | 1 | 0.424 | 0.3041 | 0.8146 | 0.6153 | 0.6383 | 0.6437 | 0.5372 | 0.5882 | 0.606 | 0.6036 | 0.6026 | 0.8187 | 0.0187 | 0.8162 | 0.8358 |
| 24 | 1 | 1 | 1 | ▨ | 1 | 1 | 0.4026 | 0.3333 | 0.8303 | 0.6562 | 0.675 | 0.6799 | 0.6437 | 0.6227 | 0.6391 | 0.6437 | 0.6421 | 0.8338 | 0.0078 | 0.8344 | 0.8496 |
| 25 | 0.978 | 0.952 | 1 | 0.999 | ▨ | 1 | 1 | 0.3062 | 0.7033 | 1 | 1 | 1 | 1 | 1 | 1 | 1 | 1 | 0.5969 | 0.8335 | 0.7108 | 0.7028 |
| 26 | 0.227 | 0.166 | 0.958 | 1 | 1 | ▨ | 0.841 | ▨ | 1 | 1 | 1 | 1 | 1 | 1 | 1 | 1 | 1 | 0.4497 | 0.347 | 0.4189 | 0.4801 |
| 27 | 0.984 | 1 | 0.983 | 1 | 1 | 1 | ▨ | 0.972 | 1 | 1 | 1 | 1 | 1 | 1 | 0.892 | 0.8873 | 0.8859 | 0.8176 | 0.8652 | 0.8072 | 0.7888 |
| 28 | 0.257 | 0.202 | 1 | 1 | 0.997 | 1 | 1 | ▨ | 1 | 1 | 1 | 1 | 1 | 0.9814 | 1 | 1 | 1 | 1 | 1 | 0.7218 | 0.7877 |
| 29 | 0.403 | 0.206 | 1 | 1 | 1 | 1 | 1 | 1 | ▨ | 1 | 0.999 | 1 | 1 | 0.9821 | 1 | 1 | 1 | 1 | 1 | 0.7392 | 0.8015 |
| 30 | 0.338 | 0.187 | 1 | 1 | 1 | 1 | 1 | 1 | 0.999 | ▨ | 1 | 1 | 1 | 0.9824 | 1 | 1 | 1 | 1 | 1 | 0.7422 | 0.8015 |
| 31 | 0.356 | 0.211 | 1 | 1 | 1 | 1 | 1 | 0.999 | 1 | 1 | ▨ | 1 | 1 | 0.982 | 1 | 1 | 1 | 1 | 1 | 0.741 | 0.8004 |
| 32 | 0.377 | 0.165 | 0.998 | 1 | 1 | 1 | 1 | 0.999 | 0.999 | 0.999 | 0.999 | ▨ | 1 | 0.9641 | 0.982 | 1 | 0.9811 | 0.9356 | 1 | 0.725 | 0.7872 |
| 33 | 0.398 | 0.297 | 1 | 1 | 1 | 1 | 1 | 0.997 | 0.997 | 0.997 | 0.997 | 1 | ▨ | 1 | 1 | 1 | 1 | 1 | 1 | 0.7393 | 0.7993 |
| 34 | 0.552 | 0.414 | 0.999 | 1 | 1 | 1 | 1 | 0.999 | 0.994 | 0.994 | 0.994 | 1 | 1 | ▨ | 1 | 1 | 1 | 1 | 1 | 0.7463 | 0.805 |
| 35 | 0.456 | 0.307 | 1 | 1 | 1 | 1 | 1 | 0.995 | 1 | 1 | 1 | 1 | 1 | 1 | ▨ | 1 | 1 | 1 | 1 | 0.7456 | 0.8038 |
| 36 | 0.979 | 0.978 | 1 | 1 | 1 | 1 | 1 | 1 | 1 | 1 | 1 | 1 | 1 | 1 | 1 | ▨ | 1 | 1 | 1 | 0.8721 | 0.9064 |
| 37 | 0.825 | 0.798 | 0.069 | 0.003 | 1 | 1 | 1 | 0.975 | 1 | 1 | 1 | 1 | 1 | 1 | 1 | 1 | ▨ | 0.152 | 0.0308 | 0.0737 | 0.0942 |
| 38 | 1 | 1 | 1 | 1 | 1 | 1 | 1 | 1 | 1 | 1 | 1 | 1 | 1 | 1 | 1 | 1 | 1 | ▨ | 1 | 0.506 | 0.9662 |
| 39 | 0.997 | 0.998 | 1 | 1 | 1 | 1 | 1 | 1 | 1 | 1 | 1 | 1 | 1 | 1 | 1 | 1 | 1 | 1 | ▨ | 0.598 | |

Note: Numbers above the diagonal represent 1 - p (where p = significance of the Chi-square) values. Numbers below the diagonal represent D' values.

Fig. 2B (Cont'd)

Organization of specific nucelotides on IL-1 haplotypes: Pattern 1) TTC = 2_2_1

| GTC Loc. | 15191 | 11079 | 10963 | 8099 | 6483 | 5342 | 4725 | 2467 | 14233 | 13921 | 12561 | 10965 | 10888 | 6970 | 6490 | 5521 | 3243 | 1824 | ? | ? | ? |
|---|---|---|---|---|---|---|---|---|---|---|---|---|---|---|---|---|---|---|---|---|---|
| ILGN SNPs | | | | | | A-889 | | | | | | | | b-31 | | | b-3737 | | ↑ | ↑ | ↑ |
| HAPTAGS | | | | | | | | Haptag | | | | | Haptag | | | Haptag | | | | | |
| GTC SNP# | ILA31 | ILA26 | ILA25 | ILA17 | ILa15 | | ILA11 | ILA2 | ILB38 | ILB37 | ILB30 | ILB25 | ILB24 | ILB15 | ILB14 | ILB10 | ILB4 | ILB1 | S002 | S497 | SS11 |
| 9.25391 | A | | C | A | T | C | C | T | C | C | A | | G | T | | G | C | C | C | G | C |
| 3.0703 | A | | C | A | T | C | C | T | C | C | A | | G | T | | G | C | C | C | G | C |
| 1.81561 | A | | C | A | T | C | C | T | C | C | A | | G | T | | G | C | C | C | G | C |
| 1.23456 | A | | C | A | T | C | C | T | C | C | A | | G | T | | G | T | T | C | A | T |
| 0.65352 | A | | C | A | T | C | C | T | C | C | A | | G | T | | G | C | C | C | G | C |
| 0.63874 | A | | C | A | T | C | C | T | C | C | A | | G | T | | G | C | C | C | G | C |
| 0.61728 | A | | C | A | T | C | C | T | C | C | A | | G | T | | G | C | C | G | G | C |
| 0.61728 | A | | C | A | T | C | C | T | C | C | A | | G | T | | G | C | T | G | G | C |
| 0.61728 | A | | C | A | T | C | C | T | C | C | A | | G | T | | G | C | T | C | G | C |
| 0.30864 | A | | C | A | T | C | C | T | C | C | A | | G | T | | G | T | C | C | G | C |
| 0.30864 | A | | C | A | T | C | C | T | C | C | A | | G | T | | G | C | C | C | G | C |
| 0.30864 | A | | C | A | T | C | C | T | C | C | A | | G | T | | G | C | C | C | G | C |
| 19.75304 | | | | | | | | | | | | | | | | | | | | | |
| | A 4845:1=G and 2=T | | | | | | | | | | | | | | | | | | | | |
| | B 3954:1=C and 2=T | | | | | | | | | | | | | | | | | | | | |
| | B-511:1=C and 2=T | | | | | | | | | | | | | | | | | | | | |

Fig. 3A

| Organization of specific nucleotides on IL-1 haplotypes: Pattern 1) TTC = 2_2_1 | | | | | | | | | | | | | | | | | | | | | | |
|---|---|---|---|---|---|---|---|---|---|---|---|---|---|---|---|---|---|---|---|---|---|---|
| GTC Loc. | ? | 3872 | 5428 | 5711 | 8093 | 12412 | 2251 | 3763 | 4543 | 6493 | 6742 | 6953 | 7156 | 9239 | 18726 | 18792 | 20097 | 20311 | 20418 | 20579 | 21822 | |
| ILGN SNPs | | | | | | | | | | | | | | | | | | | | | | |
| HAPTAGS | Haptag | | | | | Haptag | Haptag | | | | | | | | RA2018 | | | | | Haptag | | |
| GTC SNP# | S122 | ILL13 | ILL15 | ILL17 | ILL28 | ILL49 | RA15 | RA21 | RA25 | RA31 | RA34 | RA35 | RA39 | RA44 | RA61 | RA63 | RA77 | RA78 | RA79 | RA81 | RA89 | |
| 9.25391 | C | C | T | A | C | T | T | T | C | G | A | G | T | A | T | G | T | A | T | A↑ | C | |
| 3.0703 | C | T | T | A | T | C | G | C | C | G | A | G | T | A | T | G | T | A | A | G | T | |
| 1.81561 | C | C | C | G | C | C | G | C | C | G | A | G | T | A | T | G | T | A | A | G | T | |
| 1.23456 | G | C | T | A | C | T | T | C | C | G | A | G | T | A | T | G | T | A | T | G | C | |
| 0.65352 | G | C | T | A | C | T | G | C | C | G | A | G | T | A | T | G | T | A | T | G | T | |
| 0.63874 | C | C | T | A | C | T | T | T | C | G | A | G | T | A | C | A | C | A | A | A | T | |
| 0.61728 | C | C | T | A | C | C | T | C | C | G | A | G | T | A | C | G | T | A | T | G | T | |
| 0.61728 | C | C | T | A | C | T | G | C | C | G | A | G | T | A | C | G | T | A | A | G | T | |
| 0.30864 | C | T | C | G | T | C | G | C | C | G | A | G | T | A | C | G | T | A | T | G | T | |
| 0.30864 | C | C | T | A | C | T | G | C | C | G | A | G | T | A | C | G | T | A | A | G | T | |
| 0.30864 | C | C | T | A | C | C | G | C | C | G | A | G | T | A | C | G | T | A | A | G | T | |
| 19.75304 | | | | | | | | | | | | | | | | | | | | | | |

Fig. 3B

Organization of specific nucelotides on IL-1 haplotypes: Pattern 2) GCT = 1_1_2

| GTC Loc. | 15191 | 11079 | 10963 | 8099 | 6483 | 5342 | 4725 | 2467 | 14233 | 13921 | 12561 | 10965 | 10888 | 6970 | 6490 | 5521 | 3243 | 1824 | ? | ? | ? |
|---|---|---|---|---|---|---|---|---|---|---|---|---|---|---|---|---|---|---|---|---|---|
| ILGN SNPs | ↓ | | | | A-889 | | | | | ↓ | | | | b-31 | | | b-3737 | | ↑ | | ↑ |
| HAPTAGS | | | | | | | Haptag | | | | | | | | | | | | | | |
| GTCSNP# | ILA31 | ILA26 | ILA25 | ILA17 | ILa15 | | ILA11 | ILA2 | ILB38 | ILB37 | ILB30 | ILB25 | ILB24 | ILB15 | ILB14 | ILB10 | ILB4 | ILB1 | S002 | S497 | S511 |
| Freq. | | | | | | | | | | | | | | | | | | | | | |
| 8.13959 | C | T | C | A | T | T | T | T | T | G | G | | | C | | C | C | T | C | G | C |
| 2.85817 | A | T | A | T | C | C | C | T | T | G | G | | | C | | G | C | T | C | G | C |
| 1.73695 | C | T | C | A | T | T | T | T | T | G | G | | | C | | C | C | T | C | G | C |
| 1.34788 | A | T | A | T | C | C | C | T | T | G | G | | | C | | G | C | T | C | G | C |
| 1.23456 | C | T | C | A | T | T | T | T | T | G | G | | | C | | C | C | T | C | A | T |
| 1.23456 | C | T | C | A | T | T | T | T | T | G | G | | | C | | C | C | T | G | G | C |
| 0.73221 | A | T | A | T | C | C | C | T | T | G | G | | | C | | G | C | T | C | G | C |
| 0.61728 | C | T | C | A | T | T | T | T | T | G | G | | | C | | C | C | T | C | G | T |
| 0.61728 | C | T | C | A | T | T | T | T | T | G | G | | | C | | C | C | T | C | G | C |
| 0.61728 | C | T | C | A | T | T | T | C | T | G | G | | | C | | C | C | T | C | G | C |
| 0.61728 | C | T | C | A | T | T | T | T | T | G | G | | | C | | C | C | T | C | G | C |
| 0.61728 | A | T | A | T | C | C | C | T | T | G | G | | | C | | G | C | T | C | G | C |
| 0.61728 | A | T | A | T | C | C | C | T | T | G | G | | | C | | G | C | T | C | A | C |
| 0.61728 | A | T | A | T | C | C | C | T | T | G | G | | | C | | G | C | T | C | G | C |
| 0.41686 | A | T | A | C | T | T | T | T | T | G | A | | | C | | C | C | T | C | G | C |
| 0.30864 | C | T | C | A | T | T | T | T | T | G | A | | | C | | C | C | T | C | G | C |
| 0.30864 | C | T | C | A | T | T | T | T | T | G | G | | | C | | C | C | T | C | G | C |
| 0.20041 | A | T | A | T | C | C | C | T | T | G | A | | | C | | C | C | T | C | G | C |

A 4845: 1=G and 2=T
B 3954: 1=C and 2=T
B -511: 1=C and 2=T

Fig. 4A

Organization of specific nucleotides on IL-1 haplotypes; Pattern 2) GCT = 1_1_1

| GTC Loc. | ? | 3872 | 5428 | 5711 | 8093 | 12412 | 2251 | 3763 | 4543 | 6493 | 6742 | 6953 | 7156 | 9239 | 18726 | 18792 | 20097 | 20311 | 20418 | 20579 | 21822 |
|---|---|---|---|---|---|---|---|---|---|---|---|---|---|---|---|---|---|---|---|---|---|
| ILGN SNP | | | | | | | | | | | | | | | RA2018 | | | | | | |
| HAPTAGS | Haptag | | | | | Haptag | Haptag | | | | | | | | | | | | | Haptag | |
| GTC SNP Freq. | S122 | ILL13 | ILL15 | ILL17 | ILL28 | ILL49 | RA15 | RA21 | RA25 | RA31 | RA34 | RA35 | RA39 | RA44 | RA61 | RA63 | RA77 | RA78 | RA79 | RA81 | RA89 |
| 8.13959 | C | T | T | A | C | C | T | C | C | C | C | A | C | C | A | A | C | T | A | A | T |
| 2.85817 | C | T | T | A | C | C | G | T | C | C | A | G | T | T | C | G | T | A | G | A | T |
| 1.73695 | C | T | T | A | C | C | T | C | C | C | A | A | C | C | C | A | C | T | A | A | C |
| 1.34788 | C | T | T | A | C | T | T | C | C | C | C | A | T | T | C | G | T | A | A | A | T |
| 1.23456 | G | T | C | A | T | C | G | T | C | C | A | G | T | T | C | A | T | T | A | A | T |
| 1.23456 | C | T | T | A | C | C | G | T | C | C | A | G | T | T | A | G | T | A | A | G | T |
| 0.73221 | C | T | T | A | C | T | T | C | C | C | C | A | T | T | C | G | T | A | A | A | T |
| 0.61728 | G | T | C | A | T | C | T | C | C | C | A | A | C | C | C | A | T | T | A | A | T |
| 0.61728 | C | C | T | A | C | T | T | C | C | C | A | A | C | C | A | G | T | A | A | A | C |
| 0.61728 | C | T | T | A | C | T | T | C | C | C | A | A | T | T | C | G | T | A | A | A | T |
| 0.61728 | C | T | T | A | C | C | T | C | C | C | A | A | C | C | C | G | T | A | A | G | T |
| 0.61728 | C | T | T | A | C | C | T | C | C | C | A | A | C | C | C | G | T | A | A | A | T |
| 0.61728 | C | T | T | A | C | C | T | C | C | C | A | A | T | T | C | G | T | A | A | G | T |
| 0.61728 | C | T | T | A | C | C | T | C | C | C | A | A | T | T | C | G | T | A | A | A | C |
| 0.41686 | C | T | T | A | C | C | T | T | C | C | A | G | T | T | C | A | T | A | T | A | T |
| 0.30864 | C | T | T | A | C | C | T | C | C | C | A | A | C | C | A | G | T | A | T | A | T |
| 0.30864 | C | T | T | A | C | C | T | C | C | C | A | A | T | T | A | G | T | A | T | A | C |
| 0.20041 | C | T | T | A | C | C | T | T | C | C | A | A | C | C | A | A | T | A | A | A | C |

Fig. 4B

| Organization of specific nucleotides on IL-1 haplotypes: Pattern 3) GCC = 1_1_1 | | | | | | | | | | | | | | | | | | | | | | | |
|---|---|---|---|---|---|---|---|---|---|---|---|---|---|---|---|---|---|---|---|---|---|---|---|
| | | Details on the haplotypes derived from the Sheffield families, in relation to the ILGN functional and GTC SNPs - 38 sites used in the LD map | | | | | | | | | | | | | | | | | | | | | |
| GTC Loc. | 15191 | 11079 | 10963 | 8099 | 6483 | 5342 | 4725 | 2467 | | 14233 | 13921 | 12561 | 10965 | 10888 | 6970 | 6490 | 5521 | 3243 | 1824 | ? | ? | ? |
| ILGM SNPs | | | | | A-889 | | | Haptag | | | | | | b-31 | | Haptag | b-3737 | | | | | |
| HAPTAGS | | | | | | | | | | | | | | | | | | | | | | | |
| GTC SNP Freq. | ILA31 | ILA26 | ILA25 | ILA17 | ILa15 | | ILA11 | ILA2 | ILB38 | ILB37 | | ILB30 | ILB25 | ILB24 | ILB15 | ILB14 | ILB10 | ILB4 | ILB1 | S002 | S497 | SS11 |
| 7.98845 | A | | T | A | T | C | C | C | T | G | | G | | A | T | | G | T | T | C | A | T |
| 4.91681 | A | | T | A | T | C | C | C | T | G | | G | | A | T | | G | T | T | C | A | T |
| 3.7037 | C | | T | C | A | T | T | T | T | G | | G | | A | T | | G | T | T | G | G | C |
| 3.08641 | A | | T | A | T | C | C | C | T | G | | G | | A | T | | G | T | T | C | G | C |
| 2.59406 | A | | T | A | T | C | C | C | T | G | | G | | A | T | | G | T | T | C | G | C |
| 2.35423 | A | | T | A | T | C | C | T | T | G | | G | | G | T | | G | T | T | G | G | C |
| 2.24088 | A | | T | A | T | C | C | T | T | G | | G | | G | T | | G | T | T | C | A | T |
| 1.85185 | C | | T | C | A | T | T | T | T | G | | G | | G | T | | G | T | T | G | G | C |
| 1.38412 | A | | T | C | T | C | C | T | T | G | | G | | G | T | | G | T | T | C | G | C |
| 1.23456 | C | | T | C | A | T | T | T | T | G | | G | | A | T | | G | T | T | G | G | C |
| 1.23456 | A | | T | A | T | C | T | T | T | G | | G | | A | T | | G | T | T | C | A | T |
| 1.23456 | A | | T | A | T | C | T | T | T | G | | G | | A | T | | G | T | T | G | G | C |
| 0.63339 | A | | T | A | T | C | C | T | T | G | | G | | G | T | | G | T | T | C | A | T |
| 0.62263 | A | | T | A | T | T | T | T | T | G | | G | | A | T | | G | T | T | G | G | C |
| 0.61728 | C | | T | C | A | T | T | T | T | G | | G | | G | T | | G | T | T | C | A | T |
| 0.61728 | C | | T | C | A | T | T | T | T | G | | G | | G | T | | G | T | T | G | A | T |
| 0.61728 | C | | T | C | A | T | T | T | T | G | | G | | G | T | | G | T | T | G | G | C |
| 0.61728 | C | | T | C | A | T | T | T | T | G | | G | | G | T | | G | T | C | G | G | T |
| Haplotype 0.61728 | A | | T | A | T | C | C | T | T | G | | G | | A | T | | G | T | T | G | A | T |
| Frequency 0.61728 | A | | T | A | T | T | T | T | T | G | | G | | A | T | | G | T | T | C | G | C |
| 0.1149 | A | | T | A | T | C | C | T | T | G | | G | | G | T | | G | T | T | C | G | C |
| 0.07716 | C | | T | C | A | T | T | T | T | G | | G | | G | T | | G | T | T | C | A | T |

Organization of specific nucleotides on IL-1 haplotypes: Pattern 3) GCC = 1_1_1

| GTC Loc. | ? | 3872 | 5428 | 5711 | 8093 | 12412 | 2251 | 3763 | 4543 | 6491 | 6742 | 6953 | 7156 | 9239 | 18726 | 18792 | 20097 | 20311 | 20418 | 20579 | 21822 |
|---|---|---|---|---|---|---|---|---|---|---|---|---|---|---|---|---|---|---|---|---|---|
| IIGN SNPs | | | | | | | | | | | | | | | RA2018 | | | | | | |
| HAPTAGS | Haptag | | | | | Haptag | Haptag | | | | | | | | | | | | | Haptag | |
| GTC SNP Freq | S122 | ILL13 | ILL15 | ILL17 | ILL28 | ILL49 | RA15 | RA21 | RA25 | RA31 | RA34 | RA35 | RA39 | RA44 | RA61 | RA63 | RA77 | RA76 | RA79 | RA81 | RA89 |
| 7.98845 | G | C | T | A | C | T | T | C | T | G | A | G | T | A | T | G | T | A | T | G | |
| 4.91681 | G | C | T | A | C | T | G | C | C | G | A | G | T | A | T | G | T | A | A | G | |
| 3.7037 | C | T | T | A | T | C | T | T | C | G | A | G | T | A | T | G | T | A | A | G | |
| 3.08641 | C | C | T | A | C | C | G | C | C | C | C | A | T | C | C | A | C | T | T | A | |
| 2.58406 | C | T | T | A | T | C | T | C | C | G | A | G | T | A | T | G | T | A | A | G | |
| 2.35423 | G | C | T | G | T | C | G | C | C | G | A | G | U | A | T | G | T | A | A | A | |
| 2.24088 | C | C | T | A | C | C | T | C | C | C | C | A | T | C | U | A | C | T | A | G | |
| 1.85185 | C | C | C | G | T | C | G | C | C | G | A | G | T | A | T | G | T | A | A | G | |
| 1.38412 | C | C | C | A | T | C | T | C | C | G | A | G | T | A | T | G | T | A | A | G | |
| 1.23456 | C | C | C | G | T | C | G | C | C | G | A | G | T | A | T | G | T | A | A | G | |
| 1.23456 | C | C | T | G | T | C | G | C | C | G | A | G | T | A | T | G | T | A | A | G | |
| 1.23456 | G | C | T | A | C | T | T | C | T | G | A | G | T | A | U | G | T | A | T | G | |
| 0.63339 | G | C | T | A | C | T | T | C | C | G | A | G | T | A | T | G | T | T | A | A | |
| 0.62263 | G | C | T | A | C | T | T | C | C | G | A | G | T | A | U | G | T | A | A | G | |
| 0.61728 | C | C | T | A | C | T | G | C | C | G | A | G | T | C | T | G | T | A | A | G | |
| 0.61728 | G | C | T | A | C | T | T | T | C | G | A | G | T | A | T | A | T | T | A | G | |
| 0.61728 | G | C | T | A | C | T | G | T | C | G | A | G | T | A | T | G | T | A | A | G | |
| 0.61728 | G | C | T | A | C | T | G | C | C | G | A | G | T | C | T | A | T | A | A | G | |
| 0.61728 | G | C | C | A | C | T | T | C | C | G | A | G | T | A | U | A | T | A | A | G | |
| Haplotype 0.61728 | G | C | T | G | T | C | G | C | C | G | A | G | T | A | T | G | T | T | A | A | |
| Frequency 0.61728 | C | C | T | A | T | T | T | C | C | G | A | G | T | A | U | A | T | A | A | G | |
| 0.1149 | G | C | C | G | T | C | T | C | C | G | A | G | T | A | U | A | T | T | A | A | |
| 0.07716 | G | C | T | A | C | T | T | C | C | G | A | G | T | A | U | G | T | T | T | G | |

| 0.0716 | G | C | T | A | C | T | T | C | G | A | G | T | A | C | G | T | A | G |
|---|---|---|---|---|---|---|---|---|---|---|---|---|---|---|---|---|---|---|
| 0.0716 | G | C | C | T | A | C | T | T | C | G | A | G | T | A | C | G | T | G |
| 0.0716 | G | C | C | T | A | C | T | T | C | G | A | G | T | A | C | G | A | G |
| 0.0716 | G | C | C | T | A | C | T | T | C | G | A | G | T | A | C | G | A | G |
| 0.0716 | G | C | C | T | A | C | T | T | C | G | A | G | T | A | C | G | A | G |
| 0.0716 | G | C | C | T | A | C | T | T | C | G | A | G | T | A | C | G | A | G |
| 0.0716 | G | C | C | T | A | C | T | T | C | G | A | G | T | A | C | G | T | G |
| 0.0716 | C | C | C | T | C | T | T | T | T | G | A | G | T | A | C | G | T | G |
| 0.0716 | C | C | C | T | C | T | T | T | T | G | A | G | T | A | C | G | T | G |
| 0.0716 | C | C | C | T | C | T | T | T | T | G | A | G | T | A | C | G | A | G |
| 0.0716 | C | C | C | T | C | T | T | T | T | G | A | G | T | A | C | G | A | G |
| 0.0716 | C | C | C | T | C | T | T | T | T | G | A | G | T | A | C | G | A | G |
| 0.0716 | C | C | C | T | C | T | T | T | T | G | A | G | T | A | C | G | A | G |
| 0.0716 | C | C | C | T | C | T | T | T | T | G | A | G | T | A | C | G | A | G |

Organization of specific nucleotides on IL-1 haplotypes: Pattern 4) CCC = 1_1_1

| GTC Loc | 15191 | 111079 | 10963 | 8099 | 6483 | 5342 | 4725 | 2467 | 14233 | 13921 | 12561 | 10965 | 10888 | 6970 | 6490 | 5521 | 3243 | 1824 | ? | ? | ? |
|---|---|---|---|---|---|---|---|---|---|---|---|---|---|---|---|---|---|---|---|---|---|
| ILGN SNPs | a4845 | | | | A-889 | | | | | | | | | b-31 | | | | | | | |
| HAP TAGS | | | | | | | Haptag | | | | | | | | | Haptag | | | | | |
| GTC SNP# | ILA31 | ILA26 | ILA25 | ILA17 | ILA15 | | ILA1? | ILA2 | ILB38 | ILB37 | ILB30 | ILB25 | ILB24 | ILB15 | ILB14 | ILB10 | ILB4 | ILB1 | S002 | S497 | S511 |
| 0.61728 | A | G | T | A | T | | C | C | T | G | G | C | | T | | | | C | C | G | C |
| 0.30864 | A | T | C | A | T | | C | T | C | G | G | C | A | T | | | | C | C | G | C |
| 0.30864 | A | T | C | A | T | | C | T | C | G | G | C | A | T | | | | C | C | G | C |
| 0.07716 | C | G | T | C | A | | T | T | T | G | G | C | A | T | | G | | C | C | G | C |
| 0.07716 | C | G | T | C | A | | T | T | T | G | G | C | A | T | | C | | C | C | G | C |
| 0.07716 | C | G | T | C | A | | T | T | T | G | G | C | A | T | | G | | C | C | G | C |
| 0.07716 | C | G | T | C | A | | T | T | T | G | G | C | A | T | | G | | C | C | G | C |
| 0.07716 | C | G | T | C | A | | T | T | T | G | G | C | A | T | | G | | C | C | G | C |
| 0.07716 | C | G | T | C | A | | T | T | T | G | G | C | A | T | | G | | C | C | G | C |
| 0.07716 | C | G | T | C | A | | T | T | T | G | G | C | A | T | | G | | C | C | G | C |

B 3954: 1=C and 2=T
B-511: 1=C and 2=T
B 3737: 1=C and 2=T

| Organization of specific nucleotides on IL-1 haplotypes: Pattern 4) CCC = 1_1_1 | | | | | | | | | | | | | | | | | | | | | | | |
|---|---|---|---|---|---|---|---|---|---|---|---|---|---|---|---|---|---|---|---|---|---|---|---|
| GTC Loc | ? | 3872 | 5428 | 5711 | 8093 | 12412 | 2251 | 3763 | 4543 | 6493 | 6742 | 6953 | 7156 | 9239 | 18726 | 18792 | 20097 | 20311 | 20418 | 20579 | 21822 | | |
| ILGN SNPs | | | | | | | | | | | | | | | | RA2018 | | | | | | | |
| HAPTAGS | Haptag | | | | | Haptag | Haptag | | | | | | | | | | | | | Haptag | | | |
| GTC SNP# | S122 | ILL13 | ILL15 | ILL17 | ILL28 | ILL49 | RA15 | RA21 | RA25 | RA31 | RA34 | RA35 | RA39 | RA44 | RA61 | RA63 | RA77 | RA78 | RA79 | RA81 | RA89 | | |
| 0.61728 | C | C | C | G | T | C | G | T | C | G | A | G | T | A | T | G | T | A | A | G | T | | |
| 0.30864 | C | C | C | G | T | C | T | C | T | C | C | A | C | C | T | A | C | T | A | G | T | | |
| 0.30864 | C | C | C | G | T | C | T | C | T | C | C | A | C | C | C | A | C | T | A | A | T | | |
| 0.07716 | C | C | C | G | T | C | T | C | T | G | A | G | T | A | T | G | T | A | T | G | T | | |
| 0.07716 | C | C | C | G | T | C | T | C | T | G | A | G | T | A | C | G | T | A | T | G | T | | |
| 0.07716 | C | C | C | G | T | C | T | C | T | G | A | G | T | A | C | G | T | A | A | G | C | | |
| 0.07716 | C | C | C | G | T | C | T | C | T | G | A | G | T | A | C | G | T | A | A | G | T | | |
| 0.07716 | C | C | C | G | T | C | T | C | T | G | A | G | T | A | C | G | T | A | A | G | C | | |
| 0.07716 | C | C | C | G | T | C | T | C | T | G | A | G | T | A | C | G | T | A | A | G | T | | |
| 0.07716 | C | C | C | G | T | C | T | C | T | G | A | G | T | A | C | G | T | A | A | G | C | | |

Fig.6B

List of SNPs not included in the LD table and diagram of LD and/or HAP blocks. These SNPs are in strong LD with one or more of the SNPs included in the LD table.

| Gene | GTC SNP/Site #* | Combination of sites with > 0.9 LD |
|---|---|---|
| IL-1A | 1 | 1 and 2 |
| | 3 | 2 and 3 |
| | 5 | 4 and 5 |
| | 10 | 9 and 10 |
| | 12 | 11 and 12 |
| | 14 | 13 and 14 |
| | 16 | 15 and 16 |
| | 19 | 18 and 19 |
| | 26 | 25 and 26 |
| | 32 | 31 and 32 |
| | 34 | 33 and 34 |
| IL-1B | 2 | 1 and 2 |
| | 3 | 3 and 4 |
| | 5 | 4 and 5 |
| | 6 | 5 and 6 |
| | 7 | 6 and 7 |
| | 8 | 7 and 8 |
| | 9 | 8 and 9 |
| | 17 | High heterozygosity and informative |
| IL-1F5 | 5 | 5 and 6 |
| | 7 | 6 and 7 |
| | 9 | 8 and 9 |
| | 10 | 9 and 10 |
| | 11 | 10 and 11 |
| | 14 | 13 and 14 |
| | 22 | 21 and 22 |
| | 23 | 22 and 23 |
| | 24 | 23 and 24 |
| | 27 | 27 and 28 |
| | 29 | 28 and 29 |
| | 35 | High heterozygosity and informative |
| | 36 | 36 and 37 |
| | 38 | High heterozygosity and informative |
| | 40 | High heterozygosity and informative |
| | 43 | High heterozygosity and informative |
| | 45 | High heterozygosity and informative |
| | 48 | 47 and 48 |
| | 50 | 49 and 50 |
| | 51 | High heterozygosity and informative |
| | 54 | 54 and 55 |
| | 56 | 55 and 56 |
| | 57 | 56 and 57 |

Fig. 7A

| Gene | GTC SNP/Site #* | Combination of sites with > 0.9 LD |
|---|---|---|
| IL-1RN | 14 | 14 and 15 |
|  | 19 | High heterozygosity and informative |
|  | 22 | 21 and 22 |
|  | 30 | 30 and 31 |
|  | 36 | 35 and 36 |
|  | 37 | High heterozygosity and informative |
|  | 38 | 37 and 38 |
|  | 40 | 39 and 40 |
|  | 43 | 43 and 44 |
|  | 62 | 62 and 63 |
|  | 64 | High heterozygosity and informative |
|  | 76 | 76 and 77 |
|  | 82 | 81 and 82 |

* Note: Numbers in this column represent the position of SNPs in the GTC sequence panel, consisting four genes. For example, in the gene IL1-A, sites # 1, 3 and 5 correspond, respectively, to SNP sites 2346, 2505 and 3116 in the GTC map.

| SNP# | GTC Location | Base # in IL-1 α gene | Relative to +1 | Region | cDNA | Location | AA# | Mutation | Type | % | | SNP Sequence | SEQ ID No |
|---|---|---|---|---|---|---|---|---|---|---|---|---|---|
| 1 | 2346 | 1553 | -3885 | 343903 | | Promoter | | | C/T | C=98% | T=2% | GCATGAGCCA\CGGCACCCAGCCACT | 1 |
| 2 | 2467 | 1674 | -3764 | 343782 | | Promoter | | | C/T | C=62 | T=38 | TGAACTAGAA\CTCAAGAAATTGA | 2 |
| 3 | 2505 | 1712 | -3726 | 343744 | | Promoter | | | T/C | T=98 | T=2 | CACACTCTCA\TATGAATTCTCCAT | 3 |
| 4 | 2623 | 1830 | -3608 | 343626 | | Promoter | | | G/A | G=62 | A=38 | CATATTCTGG\GACCTTCAATAAA | 4 |
| 5 | 3116 | 2323 | -3115 | 343133 | | Promoter | | | C/T | T=74 | C=26 | AAAAGTTATG\TTTTCTCTTCATTCA | 5 |
| 6 | 3475 | 2682 | -2756 | 342774 | | Promoter | | | C/T | C=66 | T=34 | TCTTTATAAG\CCATCACTTGGTG | 6 |
| 9 | 3962 | 3169 | -2269 | 342287 | | Promoter | | | G/A | G=70 | A=30 | CGAGAGGTGG\GTGCCTGAAGCCACC | 7 |
| 10 | 4113 | 3320 | -2118 | 342136 | | Promoter | | | C/T | C=98 | T=2 | TGTTCACAGT\CCCAGAAAAGCGGGC | 8 |
| 11 | 4725 | 3932 | -1506 | 341504 | | Promoter | | | C/T | C=68 | T=32 | TAAAGAGGAA\CCAAGTAAGCAGAA | 9 |
| 12 | 5029 | 4236 | -1202 | 341220 | | Promoter | | | C/T | C=78 | T=22 | ACACAAGCTG\CTTTCTCCCAGATC | 10 |
| 13 | 5342 | 4549 | -889 | 340907 | | Promoter | | | C/T | C=72 | T=28 | CCAGGCAACA\CCATTGAAGGCTC | 11 |
| 14 | 6377 | 5583 | +145 | 340907 | | Intron 1 | | | C/T | C=78 | T=22 | AAAGCTACAG\CCTCTCCTTTCTT | 12 |
| 15 | 6483 | 5689 | +251 | 339766 | | Intron 1 | | | T/A | T=66 | A=34 | CTGATTCGTT\TACTGAGGGACG | 13 |
| 16 | 6495 | 5701 | +263 | 339754 | | Intron 1 | | | G/A | G=70 | A=30 | ACTGAGGGAC\GGCAGAACTAGTTTC | 14 |
| 17 | 8099 | 7302 | +1864 | 338150 | | Intron 3 | | | A/C | A=66 | C=34 | CTTGAATCTT\AAATACTTTTGTT | 15 |
| 18 | 8127 | 7330 | +1892 | 338122 | | Intron 3 | | | G/A | G=72 | A=28 | CTCACTAGAG\GTCCAGAGACCT | 16 |
| 19 | 9058 | 8260 | +2822 | 337191 | 290 | Exon 4 | 85 | R to Q | G/A | G=98 | A=2 | AAGAAGAGAC\GGTTGAGTTT | 17 |
| 24 | 10950 | 10153 | +4718 | 335286 | | Intron 4 | | | A/C | A=78 | C=22 | TCTGGATTGG\AATATTCCTA | 18 |
| 25 | 10963 | 10166 | +4728 | 335286 | | Intron 4 | | | T/C | T=72 | C=28 | ATTCCTAATA\TCCCCTCCAG | 19 |
| 26 | 11079 | 10282 | +4845 | 335170 | 376 | Exon 5 | 114 | A to S | G/T | G=72 | T=28 | GCCTAGGTCA\GCACCTTTAG | 20 |
| 30 | 12864 | 12065 | +6627 | 333385 | | Intron 6 | | | G/C/A | G=38 C=36 A=26 | | GCCCCCACCT\GCCACCCA | 21 |
| 31 | 15191 | 14249 | +8811 | 331038 | | Intron 6 | | | A/C | A=68 | T=32 | CCTTTTTCTA\ACATCTTGTTCTCTA | 22 |
| 32 | 15840 | 14898 | +9460 | 330409 | 1260 | Exon 7 3' UTR | | | G/A | A=74 | G=26 | TTTGCCTTCT\CTVACTTTTAAGTT | 23 |
| 33 | 15993 | 15051 | +9613 | 330256 | 1440 | Exon 7 3'UTR | | | C/T | T=72 | C=28 | AAATACTTCT\TGAAGCCGAGC | 24 |
| 34 | 16129 | 15187 | +9749 | 330120 | 1549 | Exon 7 3'UTR | | | C/G | C=96 | G=4 | CTGAGTGTGA\CCAGGCATCCTC | 25 |

| SNP# | GTC Location | Base # in IL-1β gene | Relative to +1 | Region | cDNA | Location | AA# | Mutation Type | Type | % | SNP Sequence | SEQ ID No |
|---|---|---|---|---|---|---|---|---|---|---|---|---|
| 1 | 1824 | 770 | -5164 | 397483 | | Promoter | | | C/T | C=84 T=16 | GCCTGGGTCC/CAGACTTGACAAA | 26 |
| 2 | 3029 | 1975 | -3959 | 396278 | | Promoter | | | T/C | T=96 C=4 | AGAAAAGACA/TAGAGTAGGA | 27 |
| 3 | 3095 | 2041 | -3893 | 396212 | | Promoter | | | G/A | G=70 A=30 | TCCAAAGGAA/GGACAAGGTC | 28 |
| 4 | 3243 | 2189 | -3745 (-3737) | 396063 | | Promoter | | | C/T | C=62 T=38 | GGGAGGAGAATGGAATGTCCCTTGGACTCT | 29 |
| 5 | 3302 | 2248 | -3686 | 396005 | | Promoter | | | A/G | A=98 G=2 | GAAGAAGCCCATTGGAGATGATG | 30 |
| 6 | 3734 | 2680 | -3254 | 395573 | | Promoter | | | T/C | T=96 C=4 | GATAACTGGCTGCGAAGCCCATGAT | 31 |
| 7 | 4083 | 3029 | -2905 | 395224 | | Promoter | | | A/G | A=98 G=2 | GGAAGACAGG/ATCTGATACATAC | 32 |
| 8 | 4594 | 3540 | -2394 | 394713 | | Promoter | | | G/A | G=98 A=2 | CCTGTCACTG/GCTTTGATCCTCCTT | 33 |
| 9 | 4610 | 3556 | -2378 | 394697 | | Promoter | | | G/A | G=96 A=4 | ATCCTCCTTC/GTTCAGCTTGTAATC | 34 |
| 10 | 5521 | 4464 | -1470 (-1464) | 393786 | | Promoter | | | G/C | G=70 C=30 | CACTCCCTTG/GATAATGCAGAGCGAG | 35 |
| 14 | 6490 | 5423 | -511 | 392837 | | Promoter | | | T/C | T=54 C=46 | AGAGAGTCCT/CTGAGGCAGAGAAC | 36 |
| 15 | 6970 | 5903 | -31 | 392337 | | Promoter | | | C/T | C=54 T=46 | TTTTGAAAGC/CATAAAAACAGCGAGGGAG | 37 |
| 17 | 7046 | 5979 | +45 | 392261 | 45 | Exon 1 5' UTR | | | T/C | T=54 C=46 | GCTCTGGGAT/TCTCTTCAGCCAATCTTCAT | 38 |
| 19 | 7750 | 6680 | +746 | 391557 | | Intron 2 | | | C/T | none | ACTACTTTCC/CATTACAAGTCCCTCCAG | 39 |
| 24 | 10888 | 9810 | +3876 | 388419 | | Intron 4 | | | G/A | G=64 A=36 | AAATTTTGCC/GCCTCGCCTCGCCTCACGAG | 40 |
| 25 | 10965 | 9887 | 3953 | 388342 | 401 | Exon 5 | 105 | F to F | T/C | C=78 T=22 | CTATCTTCTT/CGACACATGGGATAACG | 41 |
| 30 | 12561 | 11482 | +5548 | 386746 | | Intron 6 | | | G/A | G=78 A=22 | CCTTCTCCCC/GCCCCCATCCCTAGG | 42 |
| 35 | 13517 | 12440 | +6506 | 385790 | 997 | Exon 7 3' UTR | | | C/A | C=98 A=2 | ATAGCCTGGA/CTTTCCTGTTGTCT | 43 |
| 37 | 13921 | 12845 | +6911 | 385386 | 1401 | Exon 7 3' UTR | | | G/C | G=78 A=22 | CTTTAATTAA/GACTGAAAATATATAAGC | 44 |
| 38 | 14233 | 13148 | +7214 | 385074 | | | | | C/T | C=84 T=16 | CAGTGCACAT/CTGGAACAGGATC | 45 |

Fig. 9

IL-1 RNic

| SNP # | GTC Location | Base # in IL-1 RN Gene | Relative to +1 | Region | cDNA | Location | AA # | Mutation | Type | % | | SNP Sequence | SEQ ID No |
|---|---|---|---|---|---|---|---|---|---|---|---|---|---|
| 14 | 2189 | 11268 | -4864 | 669240 | | | | | G/A | G=86 | A=14 | GTTGGGTCAC\GTACCGACGTGCTA | 46 |
| 15 | 2251 | 11330 | -4744 | 669277 | | | | | T/G | T=76 | G=24 | ACTGTTCACATAGCCAAGATATGGA | 47 |
| 18 | 3332 | 12412 | -3662 | 670358 | | | | | T/G | T=56 | G=4 | TGTTTGCTTGTTCTTCTCTCTCAGC | 48 |
| 19 | 3576 | 12657 | -3417 | 670602 | | | | | A/G | G=80 | A=20 | AGCTGGGTCT\GTGAGTTGTGGTGGC | 49 |
| 21 | 3763 | 12844 | -3230 | 670789 | | | | | C/T | C=82 | T=18 | GTGTGTGTCTCTGTGTTTGTGTGTG | 50 |
| 22 | 3803 | 12886 | -3188 | 670829 | | | | | G/A | G=98 | A=2 | GAGAGAATGAGAATATGAGTGGTG G | 51 |
| 25 | 4543 | 13626 | -2448 | 671580 | | | | | T/C | C=78 | T=22 | TATCTTGCTCTCCATTCCTGATGC | 52 |
| 26 | 4648 | 13731 | -2343 | 671674 | | | | | T/C | T=98 | C=2 | GTCACCATCA\TTGGGGTTGTGGATC | 53 |
| 29 | 5534 | 14616 | | 672560 | | Promoter | | | C/T | C=98 | T=2 | TGAGCCAAGG\CGGAAGAGAACAGG A | 54 |
| 30 | 5992 | 15073 | -1002 | 673020 | | Promoter | | | T/C | T=74 | C=26 | GCAGATAGCA\TCAGGTCATTTTGC | 55 |
| 31 | 6493 | 15573 | -501 | 673519 | | Promoter | | | G/C | G=70 | C=30 | CTCTCAGAGAG\GGGCTTCCCTGGCCA | 56 |
| 32 | 6494 | 15574 | -500 | 673520 | | Promoter | | | G/A | G=98 | A=2 | TCTCAGAGAG\GGGCTTCCCTGGCCAC | 57 |
| 33 | 6606 | 15686 | -388 | 673632 | | Promoter | | | C/T | C=70 | T=30 | TATTTTATTTGCTAACTTGTTTCTTG | 58 |
| 34 | 6742 | 15822 | -252 | 673768 | | Promoter | | | A/C | A=70 | C=30 | GCACACATGCATGAGCTGGCGGCAG | 59 |
| 35 | 6953 | 16033 | -41 | 673979 | | Promoter | | | G/A | G=70 | A=30 | GGGAGGGGAGGCTGGGCTCCTCCTT | 60 |
| 36 | 7034 | 16114 | +40 | 674060 | 36 | Exon 1 5' UTR | | | G/A | G=70 | A=30 | CCCAGGTACT\GCCCGGGTGCTACTT | 61 |
| 37 | 7090 | 16170 | +96 | 674116 | 92 | Exon 1 5' UTR | | | G/A | G=74 | A=26 | GGAAGACCTC\GGAAGACCTCCTGTC | 62 |
| 38 | 7109 | 16189 | +115 | 674135 | 111 | Exon 1 5' UTR | | | G/C | G=70 | C=30 | CCTGTCCTATGAGGCCCTCCCCATG | 63 |
| 39 | 7156 | 16235 | +162 | 674182 | | Intron 1 | | | T/C | T=70 | C=30 | TCTCATTTTTCACCTGAGAAATGA | 64 |
| 40 | 7298 | 16378 | +304 | 674324 | | Intron 1 | | | A/G | A=70 | G=30 | GGAGGCATCCATGGGAGACCATGCA | 65 |
| 42 | 9021 | 18100 | +2027 | 676047 | | Intron 1 | | | G/T | G=80 | T=20 | GTGCATACTC\GGACTGGAAACTGGA | 66 |
| 43 | 9064 | 18143 | +2060 | 676090 | | Intron 1 | | | G/C | G=70 | C=30 | AAAGGATAGA\GATGGAACCATGTG C | 67 |
| 44 | 9239 | 18316 | +2245 | 676265 | | Intron 1 | | | A/C | A=70 | C=30 | AGGGTAAATT\ATTTTTAGGATCCAA | 68 |

Fig. 10A

IL-1 RNic (Continued)

| SNP # | GTC Location | Base # in IL-1 RN Gene | Relative to +1 | Region | cDNA | Location | AA # | Mutation | Type | % | SNP Sequence | SEQ ID No |
|---|---|---|---|---|---|---|---|---|---|---|---|---|
| 61 | 18726 | 27810 | +11732 | 685752 | 239 | Exon 3 | 39 | A to A | T/C | T=72 C=28 | AACTAGTTGCTGGATACTTGCAAGG | 69 |
| 62 | 18781 | 27865 | +11787 | 685807 | | Intron 3 | | | T/C | T=74 C=26 | GCCAGGAAAGTCAATGTATGTGGGC | 70 |
| 63 | 18792 | 27876 | +11797 | 685818 | | Intron 3 | | | G/A | G=72 A=28 | CAATGTATGTGGGCATCACGTCACT | 71 |
| 64 | 18813 | 27897 | +11819 | 685839 | | Intron 3 | | | G/C | G=72 C=28 | CACTTTGCCCGTCTGTCTGCAGCAG | 72 |
| 65 | 18841 | 27938 | +11860 | 685880 | | Intron 3 | | | T/G | T=88 G=12 | TGCACAAACCCTAGGTCAATGTCCTAATC | 73 |
| 66 | 18857 | 27941 | +11855 | 685903 | | Intron 3 | | | A/C | A=72 C=28 | AAACCCTAGGTGCAATGTCCTAATC | 74 |
| 67 | 18892 | 27975 | +11890 | 685918 | | Intron 3 | | | T/C | T=96 C=4 | TGTATTCAAGTTTGAAGCTGGGAGG | 75 |
| 68 | 18895 | 27979 | +11892 | 685921 | | Intron 3 | | | G/A | G=98 C=2 | ATTCAAGTTTGAAGCTGGGAGGGCC | 76 |
| 76 | 20075 | 28987 | +13070 | 687101 | | Intron 3 | | | G/A | G=74 A=26 | AAAAATACCCGGGGTCTTCTTCATTA | 77 |
| 77 | 20097 | 29010 | +13092 | 687123 | | Intron 3 | | | T/C | T=70 C=30 | TTATTGCTGCTTCCTCTTCTATTAA | 78 |
| 78 | 20311 | 29224 | +13307 | 687337 | | Intron 3 | | | A/T | A=78 T=22 | AAACAACCAAAATTTTTCTTATGA | 79 |
| 79 | 20418 | 29331 | +13414 | 687444 | | Intron 4 | | | T/A | T=58 A=42 | GCAGAGTGCCTGGCTTGCGCTGGGC | 80 |
| 80 | 20524 | 29436 | +13520 | 687550 | | Intron 4 | | | T/G | T=76 G=24 | GCATGGCGGCTGACTTCCAAAAGGG | 81 |
| 81 | 20579 | 29491 | +13575 | 687605 | | Intron 4 | | | G/A | G=50 A=50 | CGCTTATTATGACTTCTGCTTGCAT | 82 |
| 82 | 20618 | 29531 | +13614 | 687644 | | Intron 4 | | | C/T | C=70 T=30 | AAGCCAGTCACGTGGCTAAGTCTAG | 83 |
| 89 | 21822 | 30735 | +14818 | 688848 | 458 | Exon 4 | 112 | S to S | T/C | T=60 C=40 | GCTCAGACAGTGGCCCCACCACCAG | 84 |

Fig. 10B

IL-1 RNsec

| SNP # | GTC Location | Base # in IL-1 RN gene | Relative to +1 | Region | cDNA | Location | AA # | Mutation | Type | % | | SNP Sequence | SEQ ID No |
|---|---|---|---|---|---|---|---|---|---|---|---|---|---|
| 61 | 18726 | 27810 | 2014 (+2018) | 685752 | 194 | Exon 2 | 57 | A to A | T/C | T=72 | C=28 | AACTAGTTGCTGGATACTTGCAAGG | 85 |
| 62 | 18781 | 27865 | 2069 | 685807 | | Intron 2 | | | T/C | T=74 | C=26 | GCCAGGAAAGTCAATGTATGTGGGC | 86 |
| 63 | 18792 | 27876 | 2080 | 685818 | | Intron 2 | | | G/A | G=72 | A=28 | CAATGTATGTGGGCATCACGTCACT | 87 |
| 64 | 18813 | 27897 | 2101 | 685839 | | Intron 2 | | | G/C | G=72 | C=28 | CACTTTGCCGTCTGTCTGCAGCAG | 88 |
| 66 | 18857 | 27938 | 2142 | 685903 | | Intron 2 | | | A/C | A=72 | C=28 | AAACCCTAGGTGCVAATGTCCTAATC | 89 |
| 67 | 18892 | 27976 | 2180 | 685918 | | Intron 2 | | | T/C | T=96 | C=4 | TGTATTCAAGTTTGAAGCTGGGAGG | 90 |
| 68 | 18895 | 27979 | 2183 | 685921 | | Intron 2 | | | G/A | G=98 | C=2 | ATTCAAGTTTGAAGCTGGGAGGGCC | 91 |
| 76 | 20075 | 28988 | 3192 | 687101 | | Intron 2 | | | G/A | G=74 | A=26 | AAAAATACCCGGGGTCTCTTCATTA | 92 |
| 77 | 20097 | 29010 | 3214 | 687123 | | Intron 2 | | | T/C | T=70 | C=30 | TTATTGCTGCTTCCTGTCTTCTATTAA | 93 |
| 78 | 20311 | 29224 | 3428 | 687337 | | Intron 2 | | | A/T | A=78 | T=22 | AAACAACCAAAATTTTTTCTTATGA | 94 |
| 79 | 20418 | 29331 | 3535 | 687444 | | Intron 3 | | | T/A | T=58 | A=42 | GCAGAGTGCCTGGCTTGCGCTGGGC | 95 |
| 80 | 20524 | 29437 | 3641 | 687550 | | Intron 3 | | | T/G | T=76 | G=24 | GCATGGCGGCTGACTTCCAAAAGGG | 96 |
| 81 | 20579 | 29492 | 3696 | 687605 | | Intron 3 | | | G/A | G=50 | A=50 | CGCTTATTATGACTTCTGCTTGCAT | 97 |
| 82 | 20618 | 29531 | 3735 | 687644 | | Intron 3 | | | C/T | C=70 | T=30 | AAGCCAGTCACGTGGCTAAGTCTAG | 98 |
| 89 | 21822 | 30735 | 4939 | 688848 | 413 | Exon 4 | 130 | S to S | T/C | T=60 | C=40 | GCTCAGACAGCGGCCCCACCACCAG | 99 |
| 90 | 22104 | 31017 | 5221 | 689130 | | Exon 4 3' UTR | | | C/G | C=60 | G=40 | GGCGTCACAACAACCTGGTCACAGG | 100 |
| 91 | 22930 | 31843 | 6047 | 689956 | | Exon 4 3' UTR | | | | insertion | | CTCCCCCACCVAGGCTGGGAGCTCTG | 101 |
| 93 | 23062 | 32206 | 6410 | 690319 | | | | | T/C | T=68 | C=32 | GCAAAAAGATATGGGCAGCACTG | 102 |
| 94 | 23293 | 32236 | 6440 | 690349 | | | | | A/G | A=98 | G=2 | AACAGCCTCTACTGGAAACAACCCA | 103 |
| 95 | 23323 | 31975 | 6179 | 690088 | | | | | A/G | A=96 | G=4 | AAAGTTCCCTACTTCCTGTGACTTC | 104 |

Fig. 11

IL1A SNP CONSTRUCT GENOTYPES

| CONSTRUCTS/SNP# | 1 | 2 | 3 | 4 | 5 | 6 | 7 | 8 | 9 | 10 | 11 | 12 | 13 | 14 | 15 | 16 | SEQ ID No |
|---|---|---|---|---|---|---|---|---|---|---|---|---|---|---|---|---|---|
| pGL-AL4G | | | | | | | | | | | | | | | | | |
| pGL-A1T | T | | | | | | | | | | | | | | | | |
| pGL-A2T | C | T | | | | | | | | | | | | | | | |
| pGL-A3C | C | C | C | | | | | | | | | | | | | | |
| pGL-A4T | C | C | T | T | | | | | | | | | | | | | |
| pGL-A5C | C | C | T | G | C | | | | | | | | | | | | |
| pGL-A6T | C | C | T | G | T | T | | | | | | | | | | | |
| pGL3-IL1AL3X | | | | | | | | | | | | | | | | | |
| pGL-A9A | | | | | | | | | A | | | | | | | | |
| pGL-A10T | | | | | | | | | G | T | | | | | | | |
| pGL-A11T | | | | | | | | | G | C | T | | | | | | |
| pGL-A12T | | | | | | | | | G | C | C | T | | | | | |
| pGL-A13T | | | | | | | | | G | C | C | C | T | | | | |
| pGL3-IL1AL3SX | | | | | | | | | | | | | | C | T | G | 105 |
| pGL-A14T | | | | | | | | | | | | | | T | T | G | 106 |
| pGL-A15A | | | | | | | | | | | | | | C | A | G | 107 |
| pGL-A16A | | | | | | | | | | | | | | C | T | A | 108 |

Fig. 14A

IL1A SNP CONSTRUCT GENOTYPES

| CONSTRUCTS/SNP# | 1 | 2 | 3 | 4 | 5 | 6 | 7 | 8 | 9 | 10 | 14 | 15 | 17 | SEQ ID No |
|---|---|---|---|---|---|---|---|---|---|---|---|---|---|---|
| pGL3-IL1BS | T | T | G | C | A | T | A | G | G | G | C | T | T | 112 |
| pGL-B1C | T | C | G | C | A | T | A | G | G | G | C | T | T | 113 |
| pGL3-IL1BS3KM | T | T | G | C | A | T | A | G | G | G | C | T | T | 114 |
| pGL-B2C | T | T | C | C | A | T | A | G | G | G | C | T | T | 115 |
| pGL-B3A | T | T | A | C | A | T | A | G | G | G | C | T | T | 116 |
| pGL-B4T | T | T | G | T | A | T | A | G | G | G | C | T | T | 117 |
| pGL-B5G | T | T | G | C | G | T | A | G | G | G | C | T | T | 118 |
| pGL-B6C | T | T | G | C | A | C | A | G | G | G | C | T | T | 119 |
| pGL-B7G | T | T | G | C | A | T | G | G | G | G | C | T | T | 120 |
| pGL-B8A | T | T | G | C | A | T | A | A | G | G | C | T | T | 121 |
| pGL-B9A | T | T | G | C | A | T | A | G | A | G | C | T | T | 122 |
| pGL-B10C | T | T | G | C | A | T | A | G | G | C | C | T | T | 123 |
| pGL-B14T | T | T | G | C | A | T | A | G | G | G | T | T | T | 124 |
| pGL-B15C | T | T | G | C | A | T | A | G | G | G | C | C | T | 125 |
| pGL3-IL1BL3KM | T | T | G | C | A | T | A | G | G | G | C | T | C | 126 |
| pGL-B17T | T | T | G | C | A | T | A | G | G | G | C | T | T | 127 |

Fig. 15A

IL1B PROMOTER SNP CONSTRUCTS (ALLELE 2 AT 14 AND 15)

| CONSTRUCTS/SNP# | 1 | 2 | 3 | 4 | 5 | 6 | 7 | 8 | 9 | 10 | 14 | 15 | 17 | SEQ ID No |
|---|---|---|---|---|---|---|---|---|---|---|---|---|---|---|
| pGL-BS.2    | T | T | G | C | A | T | A | A | G | G | T | C |   | 128 |
| pGL-B1C.2   | C | T | G | C | A | T | A | A | G | G | T | C |   | 129 |
| pGL-BSK.2   | T | T | G | C | A | T | A | A | G | G | T | C |   | 130 |
| pGL-B2C.2   | T | C | G | C | A | T | A | A | G | G | T | C |   | 131 |
| pGL-B3A.2   | T | T | A | C | A | T | A | A | G | G | T | C |   | 132 |
| pGL-B4T.2   | T | T | G | T | A | T | A | A | G | G | T | C |   | 133 |
| pGL-B5G.2   | T | T | G | C | G | T | A | A | G | G | T | C |   | 134 |
| pGL-B6C.2   | T | T | G | C | A | C | A | A | G | G | T | C |   | 135 |
| pGL-B7G.2   | T | T | G | C | A | T | G | A | G | G | T | C |   | 136 |
| pGL-B8A.2   | T | T | G | C | A | T | A | A | G | G | T | C |   | 137 |
| pGL-B9A.2   | T | T | G | C | A | T | A | A | G | G | T | C |   | 138 |
| pGL-B10C.2  | T | T | G | C | A | T | A | A | G | C | T | C |   | 139 |
| pGL-B14T.2  | T | T | G | C | A | T | A | A | G | G | T | C |   | 140 |
| pGL-B15C.2  | T | T | G | C | A | T | A | A | G | G | T | C |   | 141 |
| pGL-BLK.2   | T | T | G | C | A | T | A | A | G | G | C | T |   | 142 |
| pGL-B17T.2  | T | T | G | C | A | T | A | A | G | G | T | C | T | 143 |

Fig. 15C

IL1RN SNP CONSTRUCT GENOTYPES

| CONSTRUCTS/SNP# | 15 | 18 | 19 | 21 | 22 | 25 | 26 | 29 | 30 | 31 | 32 | 33 | 34 | 35 | 36 | 37 | 38 | SEQ ID No |
|---|---|---|---|---|---|---|---|---|---|---|---|---|---|---|---|---|---|---|
| pGL3-IL1RNS | T | T | G | C | G | C | T | C | T | G | G | C | A | G | G | | | 144 |
| pGL-RN15G | G | T | G | C | G | C | T | C | T | G | G | C | A | G | G | | | 145 |
| pGL-RN18G | T | G | G | C | G | C | T | C | T | G | G | C | A | G | G | | | 146 |
| pGL-RN19A | T | T | A | C | G | C | T | C | T | G | G | C | A | G | G | | | 147 |
| pGL-RN21T | T | T | G | T | G | C | T | C | T | G | G | C | A | G | G | | | 148 |
| pGL-RN22A | T | T | G | C | A | C | T | C | T | G | G | C | A | G | G | | | 149 |
| pGL3-IL1RNS | | | | | | C | T | C | T | G | G | C | A | G | G | | | 150 |
| pGL-RN25T | | | | | | T | T | C | T | G | G | C | A | G | G | | | 151 |
| pGL-RN26C | | | | | | C | C | C | T | G | G | C | A | G | G | | | 152 |
| pGL-RN29T | | | | | | C | T | T | T | G | G | C | A | G | G | | | 153 |
| pGL-RN30C | | | | | | C | T | C | C | G | G | C | A | G | G | | | 154 |
| pGL3-IL1RNS | | | | | | | | | | G | G | C | A | G | G | | | |
| pGL-RN31C | | | | | | | | | | C | G | C | A | G | G | | | |
| pGL-RN32A | | | | | | | | | | G | A | C | A | G | G | | | |
| pGL-RN33T | | | | | | | | | | G | G | T | A | G | G | | | |
| pGL-RN34C | | | | | | | | | | G | G | C | C | G | G | | | |
| pGL-RN35A | | | | | | | | | | G | G | C | A | A | G | | | |
| pGL-RN36A | | | | | | | | | | G | G | C | A | G | A | | | |
| pGL3-IL1RNL3SX | | | | | | C | T | C | T | G | G | C | A | G | G | A | G | 155 |
| pGL-RN37G | | | | | | C | T | C | T | G | G | C | A | G | G | G | G | 156 |
| pGL-RN38C | | | | | | C | T | C | T | G | G | C | A | G | G | A | C | 157 |

Fig. 16A

| Gene: *IL1A (IL1F1)* | | Orientation: Reversed | | SEQ ID No |
|---|---|---|---|---|
| Position | Exon | Exon boundaries | Type | |
| 065938-067002 | *IL1A-7* | GAGATGCCTGAGATA - ACATTAATTACCTTG | CE3 + 3 | 158 |
| 069496-069620 | *IL1A-6* | TGAAATTTGACATGG - CCAGTGCTGCTGAAG | CE2 | 159 |
| 071005-071175 | *IL1A-5* | AAATCATCAAGCCTA - ATCTGGATGAAGCAG | PS + CE1 | 160 |
| 073111-073333 | *IL1A-4* | AAATCCTTCTATCAT - ATGACTCAGAGGAAG | PS | 161 |
| 074223-074271 | *IL1A-3* | TGAAAATGAAGAAGA - CTGTCTCTGAATCAG | PS | 162 |
| 075233-075287 | *IL1A-2* | AAGTCAAGATGGCCA - GAAGAACTGTTACAG | 5' + PS | 163 |
| 075952-076002 | *IL1A-1* | AAGCTGCCAGCCAGA - TTTGAGTCAGCAAAG | 5' | 164 |

Coding Interleukin-1α cDNA sequence NM_000575, genomic sequence X03833.

| | | |
|---|---|---|
| IL1A-1: | 0 | |
| IL1A-2: | makvpdmfed lkncys² | 165 |
| IL1A-3: | eneedsssid hlslng³ | 166 |
| IL1A-4: | ksfyhvsygp lhegcmdqsv slsisetskt skltfkesmv vvatngkvlk krrlslsqsi .tdddleaian dseee¹ | 167 |
| IL1A-5: | iikprsapfs flsnvkynfm riikyefiln dalnqsiira ndqyltaaal hnldeav¹ | 168 |
| IL1A-6: | kfdmgaykss kddakitvil risktqlyvt aqdedqpvll k³ | 169 |
| IL1A-7: | empeipktit gsetnllffw ethgtknyft svahprlfia tkqdywvcla ggppsitdf qilenqa* | 170 |

Fig. 18A

| Gene: *IL1B* (*IL1F2*) | | Orientation: Reversed | | SEQ ID |
|---|---|---|---|---|
| Position | Exon | Exon boundaries | Type | No |
| 121295-122108 | *IL1B-7* | AGTGTAGATCCCAAA-TAAACTTCACTGAAG | CE3 + 3' | 171 |
| 122827-122957 | *IL1B-6* | TGGTGTTCTCCATGT-ACTCTACAGCTGGAG | CE2 | 172 |
| 124196-124360 | *IL1B-5* | AACCTATCTTCTTCG-ATATGGAGCAACAAG | PS + CE1 | 173 |
| 124908-125109 | *IL1B-4* | TGCTCCTTCCAGGAC-TCATCTTTGAAGAAG | PS | 174 |
| 127099-127150 | *IL1B-3* | TGGCAATGAGGATGA-CCTAAACAGATGAAG | PS | 175 |
| 127715-127777 | *IL1B-2* | GTGTCTGGAAGCAGC-GATGGCTTATTACAG | 5'+ PS | 176 |
| 128240-128311 | *IL1B-1* | ACCAACCTCTTCGAG-ATCTTCATTGCTCAA | 5' | 177 |

Coding Interleukin-1β
*IL-1B*, from cDNA sequence M15330 and genomic sequence X04500.

```
IL1B-1:  ø
IL1B-2:  maevpklase mmayys²                                                          178
IL1B-3:  gnehdlffea dgpkqmk³                                                         179
IL1B-4:  csfqdldlcp ldggiqlris dhhyskgfrq aasvvvamdk lrkmlvpcpq tfqendlstf fpfifeee¹  180
IL1B-5:  piffdtwdnq ayvhdapvrs lnctlrdsqq kslvmsgpye lkalhlqgqd meqgv¹                181
IL1B-6:  vfsmsfvqge esndkipval alkeknlyls cvlkddkptl qle³                             182
IL1B-7:  svdpknypkk kmekpfvfnk ieinnklefe saqfpnwyis tsqaenmpvf lggtkggqdi
         tdftmqfvss *                                                                183
```

Fig. 18B

| Gene: *IL1F7* | | Orientation: Forward | | SEQ ID |
|---|---|---|---|---|
| Position | Exon | Exon boundaries | Type | No |
| 204598-204721 | *IL1F7*-b1/c1 | CTTCATTCCATTTTC-AGTGCTGCTTAGAAG | 5'+PS? | 184 |
| 205420-205482 | *IL1F7*-b2/c2 | ACCCGGCTGGAAGCC-ATTTTGTTCACACAA | PS? | 185 |
| <206821-206887 | *IL1F7*-a1 | ...ATGTCAGGCTGTGAT-AGAAGCGCTTAAGAG | PS? | 186 |
| 208769-208888 | *IL1F7*-a2/b3 | GTCCAAAGGTGAAGA-ACTACATACGCCCAG | CE1 | 187 |
| 209275-209417 | *IL1F7*-a3/b4/c3 | AGATCTTCTTTGCAT-TCCCTTCAGCTGAAG | CE2 | 188 |
| 210204-210529 | *IL1F7*-a4/b5/c4 | AAGGAGAAACTGATG-AACCTGCTCACTAAA | CE3+3' | 189 |

Coding

Different cDNAs: IL-1F7a (AF201832), IL-1F7b (AF200496) and IL-1F7c (AF251120).

| | | | | |
|---|---|---|---|---|
| IL1F7-b1/c1: | msfvgensgv | kmgsedwekd | epqccled[1] | 190 |
| IL1F7-b2/c2: | pagsplepgp | slptmnfvht | (s/k)[1] | 191 |
| IL1F7-a1: | msgcdrrete | tkgknsfkkr | lrg[1] | 192 |
| IL1F7-a2/b3: | pkvknlnpkk | fsihdqdhkv | lvldsgnlia vpdknyirpe[1] | 193 |
| IL1F7-a3/b4/c3: | iffalassls | sasaekgspi | llgvskgefc lycdkdkgqs hlqlk[3] | 194 |
| IL1F7-a4/b5/c4: | keklmklaaq | kesarrpfif | yraqvgswnm lesaahpgwf ictscncnep | |
| | vgvtdkfenr | khiefsfqpv | ckaemsevsd * | 195 |

Fig. 18C

| Gene: *IL1F9* | | Orientation: Forward | | SEQ ID |
|---|---|---|---|---|
| Position | Exon | Exon boundaries | Exon type | No |
| 269711-269760 | *IL1F9*-1 | GAGCCACGATTCAGT-ACCCTTTCTTGCCAG | 5' | 196 |
| 270302-270375 | *IL1F9*-2 | GTGCTGAGACAACCA-CCGTCTATCAATCAA | 5'+CS | 197 |
| 270903-271007 | *IL1F9*-3 | TGTGTAAACCTATTA-ACAGTGTGACCCCAG | CE1 | 198 |
| 271691-271830 | *IL1F9*-4 | TCACTGTTGCTGTTA-ACATTGCAGCTAAAA | CE2 | 199 |
| 276523-277335 | *IL1F9*-5 | GAGCAGAAGATCATG-CTAAAACTGATATAA | CE3+3' | 200 |

Coding
cDNA sequences AF200492 and AF206696.

IL1F9-1:Ø
```
IL1F9-2:mrgtpgdadg ggravyqsm¹                                          201
IL1F9-3:ckpitgtind lnqqvwtlqg qnlvavprsd svtpv¹                        202
IL1F9-4:tvavitckyp ealeqgrgdp iylgiqnpem clycekvgdq ptlqlk³            203
IL1F9-5:eqkimdlygq pepvkpflfy raktgrtstl esvafpdwfi asskrdqpii ltselqksyn
        tafelnind*                                                      204
```

| Gene: *IL1F6* | | Orientation: Forward | | SEQ ID |
|---|---|---|---|---|
| Position | Exon | Exon boundaries | Exon type | No |
| <297556-297565 | *IL1F6*-1? | ...ATGGAAAAAG | 5'+CS | 205 |
| 297658-297771 | *IL1F6*-2 | CATTGAAAATTGACA-ACCGTATGTCTCCAG | CE1 | 206 |
| 298282-298421 | *IL1F6*-3 | TCACTATTGCCTTAA-ACACTGCAGCTGAAG | CE2 | 207 |
| 299516->299728 | *IL1F6*-4 | GAAAAGGATATAATG-ACTATGCTGTTTTAA... | CE3 | 208 |

Coding
cDNA sequences AF201831.

**IL1F9-1:*meka¹***
```
IL1F6-2:lkidtpqqgs iqdinhrvwv lqdqtliavp rkdrmspv¹                      209
IL1F6-3:tialiscrhv etlekdrgnp iylglnglnl clmcakvgdq ptlqlk³             210
IL1F6-4:ekdimdlynq pepvksflfy hsqsgrnstf esvafpgwfi avsseggcpl iltqelgkan 211
        ttdfgltmlf *                                                    212
```

Fig. 18D

| Gene: *IL1F8* | | Orientation: Reversed | | SEQ ID No |
|---|---|---|---|---|
| Position | Exon | Exon boundaries | Exon type | |
| <313785-314471 | *IL1F8*-b6 | GTAGAAAGAAGTGGA-TAGTTTTTCCCATGT | CS+3' | 213 |
| 317797-317926 | *IL1F8*-b5 | CTTCAGGGCTCCCAA-GGGGAATAGGAGTGG | CS | 214 |
| <319597-319809 | *IL1F8*-a5 | GAAAAAAATATCATG-GATTCTGTGGAATAA... | CE3... | 215 |
| 320633-320772 | *IL1F8*-a4/b4 | TCACTCTTCATTTAA-ACTTTGCAGCTTAAG | CE2 | 216 |
| 322742-322849 | *IL1F8*-a3/b3 | GGGAGGCAGCACCCA-GCAGCATTAAGCCTG | CE1 | 217 |
| 323391-323460 | *IL1F8*-a2/b2 | CCTCCTCACCACCAT-TCATGAACCCACAAC | 5'+CS | 218 |
| 344518->344570 | *IL1F8*-a1/b1 | GACACGGGTTCCTCC-CTTCACTTTTCCTAG... | 5' | 219 |

Coding
Different cDNAs: IL-1F8a (AF201833), and IL-1F8b (AF200494).

| | | | | |
|---|---|---|---|---|
| IL1F8-a1/b1: | ∅ | | | |
| IL1F8-a2/b2: | mnpgr[1] | | | 220 |
| IL1F8-a3/b3: | eaapksyair dsrqmvwvls gnsliaapls rsikpv[1] | | | 221 |
| IL1F8-a4/b4: | tlhliacrdt efsdkekgnm vylgikgkdl clfcaeiqgk ptlqlk[3] | | | 222 |
| IL1F8-a5: | eknimdlyve kkaqkpflff hnkegstsvf qsvsypgwfi atsttsgqpi fltkergitn ntnfyldsve * | | | 223 |
| IL1F8-b5: | lqgsqdnigk dtcwklvgih tcinldvres cfmgtldqwg igvg[1] | | | 224 |
| IL1F8-b6: | rkkwkssfqh hhlrkkdkdf ssmrtnigmp grm* | | | 225 |

Fig. 18E

**Gene: *IL1F5***            Orientation: Forward

| Position | Exon | Exon boundaries | Exon type | SEQ ID No |
|---|---|---|---|---|
| <350401-350445 | *IL1F5*-b1 | ...AAGGAAGGAGGGAGA-GAAGGAGTGAAAAAG | 5' | 226 |
| 350810-350943 | *IL1F5*-a1 | CGCTGGGAATCCTGC-AAGGAACATTCTGAG | 5'+SORF | 227 |
| 351114-351169 | *IL1F5*-a2/b2 | GGGAGTCTACACCCT-GGCGCTGTGCTTCCG | 5'+CS | 228 |
| 352555-352640 | *IL1F5*-a3/b3 | AATGAAGGACTCGGC-GGAAGGTCATTAAAG | CE1 | 229 |
| 353827-353954 | *IL1F5*-a4/b4 | GTGAAGAGATCAGCG-ACTCTAACACTAGAG | CE2 | 230 |
| 354156-356451 | *IL1F5*-a5/b5 | CCAGTGAACATCATG-AGAAAGAGAAACAAA | CE3+3' | 231 |

Coding:
Different cDNAs: IL-1F5a (AF186094 and AJ242737) and IL-1F5b (AJ242738).

| | | |
|---|---|---|
| IL1F5-b1: | ∅ | |
| IL1F5-a1: | magrkdrgrkegegke* | 232 |
| IL1F5-a2/b2: | mvlsgalcfr² | 233 |
| IL1F5-a3/b3: | mkdsalkvly lhnnqllagg lhagkvikg¹ | 234 |
| IL1F5-a4/b4: | eeisvvpnrw ldaslspvil gvgggsqcls cgvgqeptlt le³ | 235 |
| IL1F5-a5/b5: | pvnimelylg akesksftfy rrdmgltssf esaaypgwfl ctvpeadqpv rltqlpengg wnapitdfyf qqcd* | 236 |

**Gene: *IL1F10***        Orientation: Forward

| Position | Exon | Exon boundaries | Exon type | SEQ ID No |
|---|---|---|---|---|
| 364023-364475 | *ILF10*-a1 | GGCAGTGGGACTGGG-GGCAAGATACTACAT | 5'+CS | 237 |
| 366034-366119 | *ILF10*-a2 | AATTAAATATGCAGA-ACAACTGCTGTGCAG | CE1 | 238 |
| 366244-366555 | *\*ILF10*-b1 | GCTGTGGCCTCTCCT-TCCCTACAGCTGGAG | 5'+CS + CE2 | 239 |
| 366428-366555 | *\*ILF10*-a3 | AGAAGATCTGCATAC-TCCCTACAGCTGGAG | CE2 | 240 |
| 366857-367553 | *ILF10*-a4/b2 | GATGTGAACATTGAG-TTATTGTAAACCTCT | CE3 + 3'N | 241 |

Coding

Different cDNAs: IL-1F10a (AF334755) and IL-1F10b (AY026753)

```
IL1F10-a1:    mcslpmaryy i²                                                      242
IL1F10-a2:    ikyadqkaly trdgqllvgd pvadnccae¹                                   243
*IL1F10-b1:   msssflpepl pakslqhgvp lsldsslssl lekicilpnrg
              lartkvpifl qiqggsrcla cveteeglql e³                                244
*IL1F10-a3:   kictlpnrgl drtkvpiflg iqggsrclac veteeglqle³                       245
IL1F10-a4/b2: dvnieelykg geeatrftff qsssgsafrl eaaawpgwfl cgpaepqgpv
              qltkeseart kfyfeqsw*                                               246
```

**Gene: *IL1RN (IL1F3)***        Orientation: Forward

| Position | Exon | Exon boundaries | Exon type | SEQ ID No |
|---|---|---|---|---|
| 409176-409311 | *IL1RN*-b1/c1 | GGGCAGCTCCACCCT-TCCCCATGGCTTTAG | 5'+CS | 247 |
| 411350-411412 | *IL1RN*-c2 | CTGACTTGTATGAAG-ATGCTGACTCAAAGG | CS | 248 |
| 418888-419017 | *\*IL1RN*-a1 | GCTGCAGTCACAGAA-GATGCAAGCCTTCAG | 5'+SS | 249 |
| 418966-419017 | *\*IL1RN*-b2/c3 | AGACGATCTGCCGAC-GATGCAAGCCTTCAG | CS | 250 |
| 420853-420941 | *IL1RN*-a2/b3/c4 | AATCTGGGATGTTAA-ATGTCAATTTAGAAG | CE1 | 251 |
| 422321-422433 | *IL1RN*-a3/b4/c5 | AAAAGATAGATGTGG-AGACTCCAGCTGGAG | CE2 | 252 |
| 423932-425290 | *IL1RN*-a4/b5/c6 | GCAGTTAACATCACT-AATCTTGAAAATGCC | CE3+3' | 253 |

Coding: Interleukin-1 receptor antagonist
Different cDNAs: pro-sIL-1ra (from a, X52015), icIL-1ra (form b, M55646) and icIL-1rall (form c, X84348).

```
IL1RN-b1/c1:    mal(e/a)¹                                                        254
IL1RN-c2:       dlyeeggggg gegednadsk e¹                                         255
*IL1RN-a1:      meicrglrsh litlllflfh seticrgrks skmqafr²                        256
*IL1RN-b2/c3:   ticrgrks skmqafr                                                 257
IL1RN-a2/b3/c4: iwdvnqktfy lrnnqlvagy lqgpnvnlee¹                                258
IL1RN-a3/b4/c5: kidvvpieph alflgihggk mclscvksgd etrlqle³                        259
IL1RN-a4/b5/c6: avnitdlsen rkqdkrfafi rsdsgptttsf esaacpgwfl ctameadqpv
                sltnmpdegv mvtkfyfqed e*                                         260
```

MAP POSITIONS OF POLYMORPHIC MARKERS

| POLYMORPHISM | POSITION | VARIATION (DATABASE STRAND) | VARIABILITY | REFERENCE |
|---|---|---|---|---|
| 222/223 | 069722 | $[GT]_N$ | polyallelic | A |
| IL1A+4845 | 071555 | G/A (SNP) | biallelic | B |
| gz5/gz6 | 072250 | $[AAT]_N$ | quasi-biallelic | A |
| IL1A-889 | 076892 | G/A (SNP) | biallelic | A,B |
| IL1B+3954 | 124347 | A/G (cSNP) | biallelic | A,B |
| IL1B-511 | 128822 | G/A (SNP) | biallelic | A,B |
| gaat.p33330 | 271535 | $[GAAT]_N$ | quasi-triallelic | A |
| Y31 | 335980 | $[GT]_N$ | polyallelic | A |
| IL1RN+2018 | 420907 | C/T (SNP) | biallelic | B |

Fig. 19

IL-1 GENE CLUSTER AND ASSOCIATED INFLAMMATORY POLYMORPHISMS AND HAPLOTYPES

RELATED APPLICATIONS

This application is a national stage application, filed under 35 U.S.C. §371, of International Application No. PCT/US2006/041847, filed on Oct. 25, 2006 which claims the benefit of U.S. Ser. No. 60/729,953, filed Oct. 25, 2005.

1. BACKGROUND OF THE INVENTION

IL-1 is a primary inflammatory cytokine and has been implicated in mediating both acute and chronic pathological inflammatory diseases. Two functionally similar molecules, IL-1 α and IL-1β, are encoded by separate genes (respectively, IL1A and IL1B). The third gene of the family (IL1RN) encodes IL-1 receptor antagonist (IL-1ra), an anti-inflammatory non-signaling molecule that competes for receptor binding with IL-1α and IL-1β. Pairwise comparison of IL-1α, IL-1β and IL-1ra yields <25% identity in each case, yet X-ray crystallography of IL-1β and IL-1ra reveal closely similar folds (Priestle et al. (1989) PNAS USA 86: 9667-967); Vigers et al. (1994) Biol Chem 269: 12874-12879). Structurally, the proteins consist of a single domain of 12 packed β-sheets known as a beta-trefoil. Since most of the packing interactions feature main chain atoms, it has been argued that few invariable amino acid are residues required to produce the IL-1 fold, hence extensive diversification of the coding sequences of the genes has been possible. A very similar fold is achieved in soybean trypsin inhibitor without any detectable sequence similarity. All three proteins bind the only functional signaling receptor for IL-1, the type I IL-1 receptor (IL-1R1) (see Sims et al. (1993) PNAS USA 90: 6155-6159).

IL-1 has been characterized mainly as the product of stimulated monocytes, macrophages and keratinocytes, but important roles have been suggested for IL-1 released from smooth muscle and endothelial cells (reviewed by Ross (1993) Nature 362: 801-9). Signaling through IL-1R1 involves the cytoplasmic Toll-like domain of the receptor (Heguy et al. (1992). J Biol Chem 267: 2605-2609). Functional IL-1 receptors are widely distributed in tissues. It is currently believed that IL-1ra differs from IL-1 in failing to activate the interaction between IL-1R1 and the second receptor component, IL-1 receptor accessory protein, IL-1RacP. This is a transmembrane protein that is a distant relative of IL-1R1, having a similar domain structure, but has no intrinsic affinity for IL-1 (Greenfeder et al. (1995) J Biol Chem 270: 13757-13756; Wesche et al., (1997) J Biol Chem 272: 7727-7731).

The IL-1 gene cluster is on the long arm of chromosome 2 (2q13) and contains at least the genes for IL-1α (IL-1A), IL-1β (IL-1B), and the IL-1 receptor antagonist (IL-1RN), within a region of 430 Kb (Nicklin, et al. (1994) Genomics, 19: 382-4). The maximum separation of the distal genes IL1A and IL1RN has been estimated to be 430 kb by pulse field gel electrophoresis of restriction digests of human genomic DNA (Nicklin, et al. (1994) Genomics, 19: 382-4), and the orientation of the three genes has been determined by sequence analysis of physical clones (Nothwang et al. (1997) Genomics 41: 370-378). IL-18 appears to be the fourth member of the IL-1 structural family (Bazan et al. (1996) Nature 379: 591). It is also a proinflammatory cytokine, but its activity parallels that of IL-1. IL-18 binds to a related receptor (IL-18R1) rather than IL-1R1 (Torigoe et al. (1997) J Biol Chem 272: 25737-25742), which engages a related accessory protein, IL-18RacP, rather than IL-1RacP (Born et al. (1998). The IL-18 gene, IL18, resides on chromosome 11 (Nolan et al., (1998) Genomics 51: 161-3).

Certain other proteins that contain IL-1-like elements have been identified from commercial and public cDNA databases (Mulero et al. (1999) Biochem Biophys Res Commun 5: 702-6; Smith et al. (2000) J Biol Chem 275: 1169-1175); Kumar et al., (2000) J Biol Chem 275: 10308-10314; Busfield et al. (2000) Genomics 66: 213-216; Lin et al. (2001) Biol Chem 276: 20597-20602). One IL-1 like gene was also identified after cDNA selection by hybridization with a YAC clone that incorporated the IL-1 cluster (Barton et al., (2000) Eur J Immunol 30: 3299-3308). This IL-1 gene and its product (i.e. the Interleukin-1-like protein 1 gene/product) are described in detail in our pending application U.S. Ser. No. 09/617,720, the contents or which are incorporated herein by reference. A uniform nomenclature system for the six new genes has recently been agreed by the investigators involved in the discovery of the genes (see Sims et al. (2001) Trends Immunol 22: 536-537) and will be used herein. Recognizing the four previously known IL-1 family members, the new human genes have been named IL1F5 (i.e. IL-1L1), IL1F6, IL1F7, IL1F8, IL1F9 and IL1F10. Protein products are named in the style, IL-1F7b (which would mean, the second described putative protein product of the IL1F7 gene). The genes generally appear to be conserved between man and mouse.

In U.S. Pat. No. 6,268,142, the contents of which is hereby incorporated by reference in its entirety, we have previously described certain polymorphisms, including SNPs, associated with IL-1 inflammatory haplotypes and their use in inflammatory disease diagnostics and therapeutics. In U.S. Ser. No. 09/617,720 and U.S. Ser. No. 09/969,215 [Publication No. US 2002/0182612)}, the contents of which are hereby incorporated in their entirety, we have previously described therapeutics and diagnostics based on the IL-1B allele 2 (+6912) polymorphism. Still further, in U.S. Ser. No. 10/300,011 (also PCT US 02/37222), the contents of which are also hereby incorporated in their entirety, we describe and characterize functional polymorphisms, including those in an upstream region of the IL-1B gene, that affect transcription and susceptibility to inflammatory and infectious disease. In addition, in U.S. Ser. No. 09/617,720, the contents of which are hereby incorporated in their entirety, we previously describe the IL-1 like-gene and its product (i.e. the Interleukin-1-like protein 1 gene/product, i.e. IL-1F5). Recognizing that the entire IL-1 gene locus is centrally involved in inflammatory disease, we herein provide further detailed IL-1 locus polymorphism, linkage, disease association and functional analysis supporting compositions for detecting genetic identity at the human IL-1 locus and their use for the prediction, diagnosis and therapy of inflammatory disease.

2. SUMMARY OF THE INVENTION

In general the invention provides compositions and methods for detecting and IL-1 haplotype (e.g. an IL-1 haplotype associated with an increased risk or a decreased risk of developing an inflammatory disease or condition). In preferred embodiments, the IL-1 haplotype is one associated with either an increased risk or a decreased risk of developing a disease or condition, however the invention necessarily encompasses materials and methods for detecting an IL-1 haplotype associated with neither an increased nor a decreased risk for developing a disease or condition (e.g. a "normal" or "wt" genotype).

In preferred embodiments, the invention provides compositions and methods for determining whether a subject has or is predisposed to developing a disease or condition that is associated with an IL-1 inflammatory haplotype by detecting an IL-1 allele associated with an inflammatory disease or disorder or any IL-1 allele in linkage disequilibrium with such an allele—e.g. one or more linked IL-1 alleles as shown in any of FIG. 1, 2A, 2B, 7A or 7B. In preferred embodiments, the linked allele has a linkage disequilibrium value (D') with the inflammatory associated allele of at least 0.5 and preferably at least 0.6, 0.7, 0.8 or 0.9.

In another embodiment, the invention provides compositions and methods for determining whether a subject has a decreased risk for developing a disease or condition that is associated with an IL-1 inflammatory haplotype by detecting an IL-1 allele associated with a decreased risk of the inflammatory disease or disorder or any IL-1 allele that is in linkage disequilibrium with such a "protective" allele—e.g. one or more linked IL-1 alleles as shown in any of FIG. 1, 2A, 2B, 7A or 7B. In preferred embodiments, the linked allele has a linkage disequilibrium value (D') with the "protective allele" of at least 0.5 and preferably at least 0.6, 0.7, 0.8 or 0.9. In certain preferred embodiments, the invention includes 4 new IL-1 haplotypes (hap1-4), based on newly identified SNPs. In one preferred embodiment, the invention provides hap1 (IL-1 haplotype pattern 1) an IL-1 pro-inflammatory (consistent with the previously described haplotype: 3322146121) which includes: the IL-1 A(+4845) allele 2 (in 100% LD with IL-1A (−889) allele 2); the IL-1B(+3954) allele 2; and the IL-1B(−511) allele 1. In another embodiment, the invention provides a hap1 haplotype comprising a multiplicity of two or more alleles of a hap 1 haplotype pattern as shown in FIGS. 3A and 3B. In preferred embodiments the hap 1 haplotype includes the IL-1 TTC/2-2-1 pattern indicated in FIGS. 3A and B.

In another embodiment, the invention provides an IL-1 haplotype, hap2, consistent with the previously described haplotype: 4411233212, which includes: the IL-1 A(+4845) allele 1 (in 100% LD with IL-1A(−889) allele 1); the IL-1B (+3954) allele 1 IL-1B(−511) allele 2. In another embodiment, the invention provides a hap2 haplotype comprising a multiplicity of two or more alleles of a hap 2 haplotype pattern as shown in FIGS. 4A and 4B. In preferred embodiments the hap 2 haplotype includes the IL-1 GCT/1-1-2 pattern indicated in FIGS. 4A and 4B.

In yet another embodiment, the invention provides an IL-1 haplotype, hap 3, consistent with the previously described ("wild type") allelic pattern 111* which includes: the IL-1 A(+4845) allele 1 (in 100% LD with IL-1A(−889) allele 1); the IL-1B(+3954) allele 1; and the IL-1B(−511) allele 1. In a preferred embodiment, the invention provides a hap3 haplotype comprising a multiplicity of two or more alleles of a hap 3 haplotype pattern as shown in FIGS. 5A and 5B. In preferred embodiments the hap 3 haplotype includes the IL-1 hap3 GCC/1-1-1 pattern indicated in FIGS. 5A and 5B.

In yet another embodiment, the invention provides newly identified SNPs, that are consistent with a new IL-1 haplotype pattern (hap4) comprising: IL-1B (+3877)allele; IL-1B(+ 3954) allele; IL-1B(−511) allele 1; and IL-1B(−3737) allele 1. In a preferred embodiment, the invention provides a hap4 haplotype comprising a multiplicity of two or more alleles of a hap 4 haplotype pattern as shown in FIGS. 6A and 6B. In preferred embodiments the hap 3 haplotype includes the IL-1 hap4 CCC/1-1-1 pattern indicated in FIGS. 6A and 6B.

It is further an object of the invention to provide methods and compositions relating to the use of sequence information from the IL-1 gene cluster and, in particular, from the novel IL-1-like genes of the IL-1 cluster. It is a further object to integrate this sequence information with genetic data. Accordingly, the invention provides a map of the IL-1 cluster that provides detailed information on the structure and organization of the genes and associated polymorphisms. It is still further an object of the invention to provide methods of predicting and diagnosing a disease or disorders associated with the IL-1 gene cluster. It is further a goal to provide a multiplicity of human IL-1 gene cluster sequence identifiers, comprising one or more nucleic acids for the identification of an IL-1 polymorphism as shown in FIG. 4.

3. BRIEF DESCRIPTION OF THE FIGURES

FIGS. 2 (A and B) shows representative quantitative values for linkage disequilibrium (D' values appear below the diagonal) and their statistical significance (1-p values appear above the diagonal) of representative SNPs throughout the IL-1 gene cluster.

FIGS. 3 (A and B) shows the organization of SNPs of IL-1 haplotype pattern 1 (hap 1) (T-T-C=2_2_1).

FIGS. 4 (A and B) shows the organization of SNPs of IL-1 haplotype pattern 2 (hap 2) (G-C-T=1_1_2).

FIGS. 6 (A and B) shows the organization of SNPs of IL-1 haplotype pattern 4 (hap 4) (C-C-C=1_1_1).

FIGS. 7 (A and B) shows the SNPs that are in strong linkage disequilibrium and not specifically included in the LD table FIG. 8 shows the identity and position of IL-1A gene polymorphisms.

FIG. 9 shows the identity and position of IL-1B gene polymorphisms.

FIGS. 10 (A and B) shows the identity and position of IL-1RNic gene polymorphisms.

FIG. 11 shows the identity and position of IL-1RNsec gene polymorphisms.

Figure 15B:
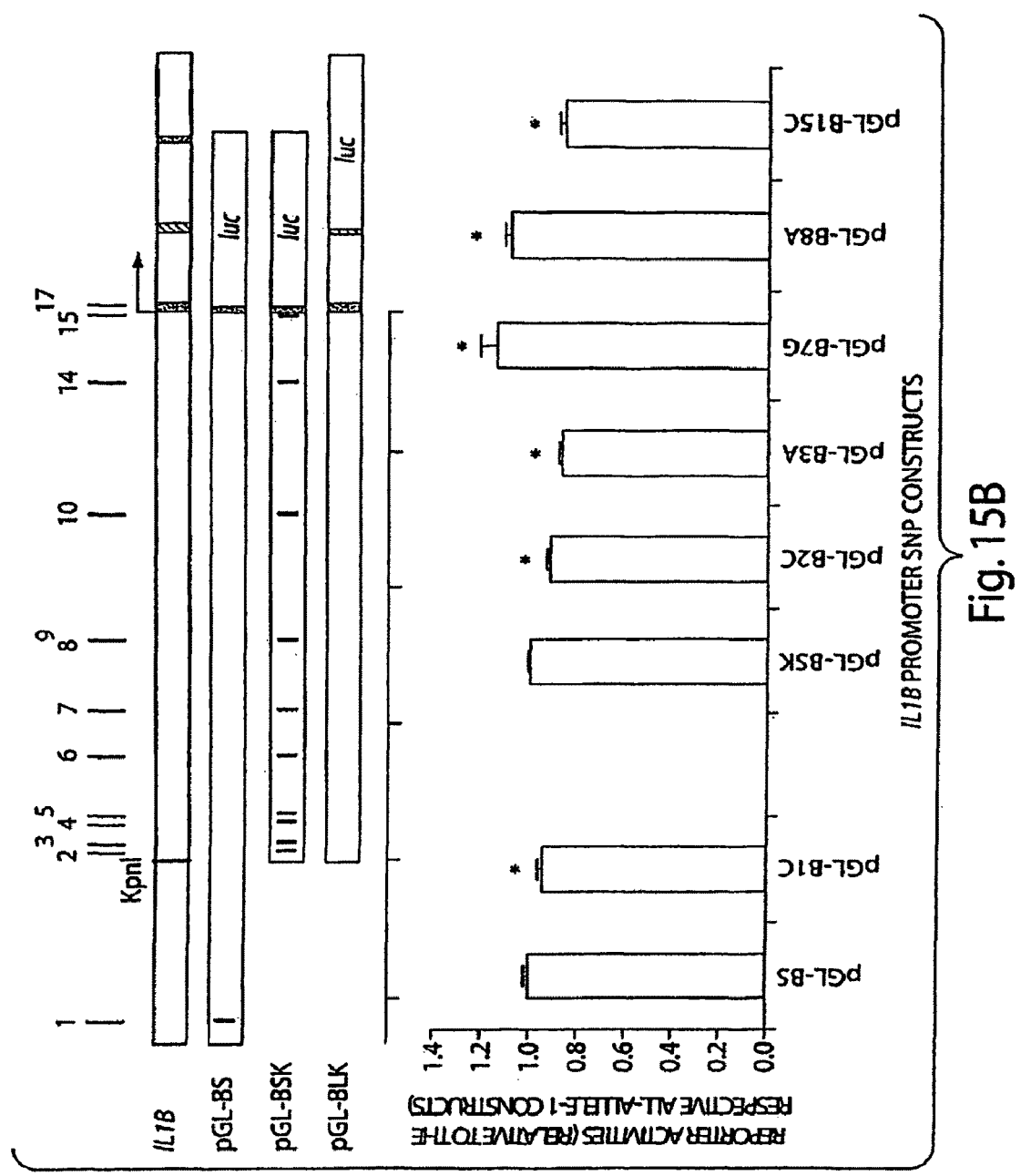
Figure 15D:
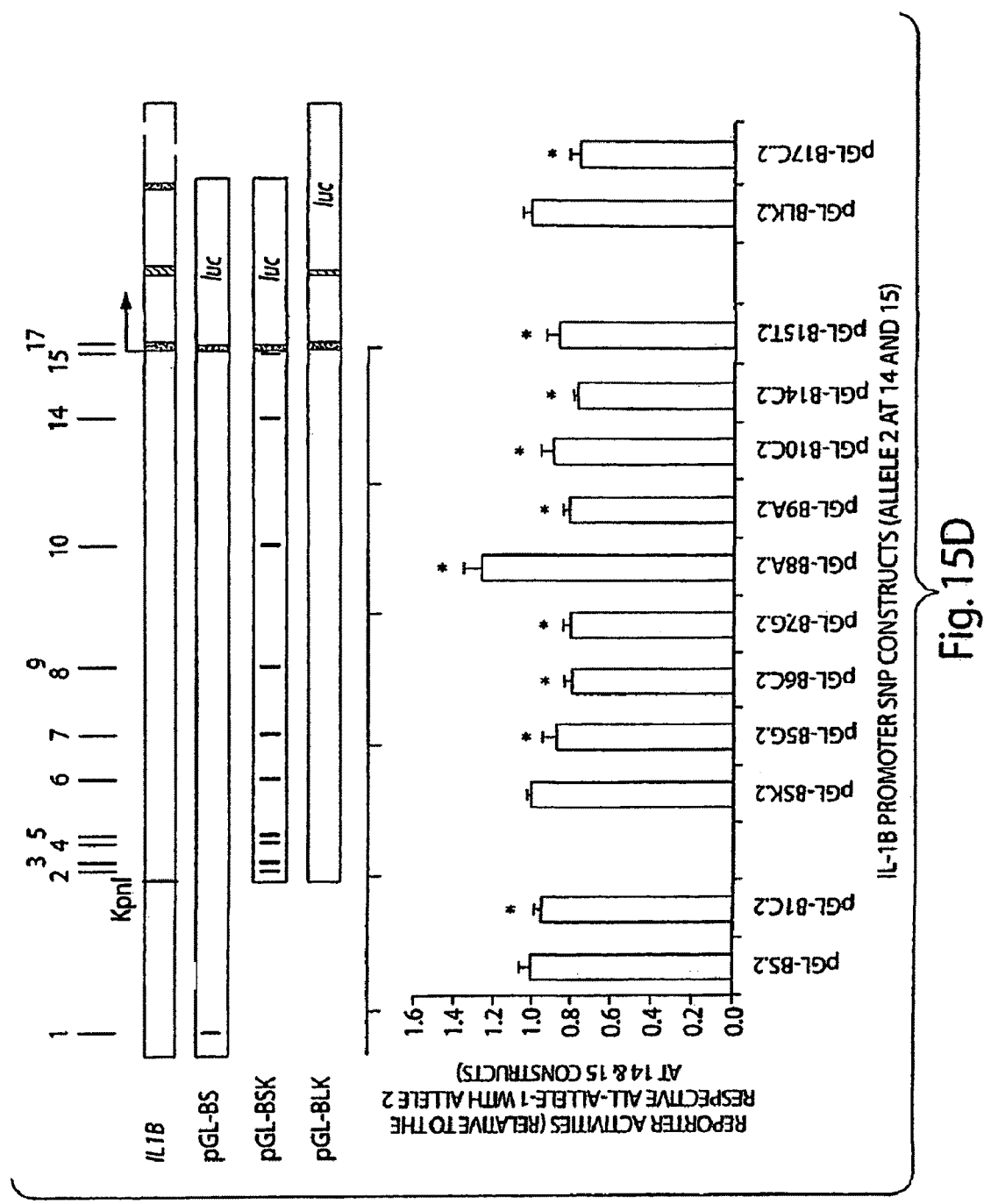

FIGS. 15 (A, B, C, and D) shows the genotypes of IL-1B SNP constructs (A) and selected re reporter activities in a fibroblast cell line (B); as well as the genotypes of another set of IL-1B constructs in with allele 2 occurring at positions 14 and 15 (C) and selected reporter activities in a fibroblast cell line (D).

Figure 16B:
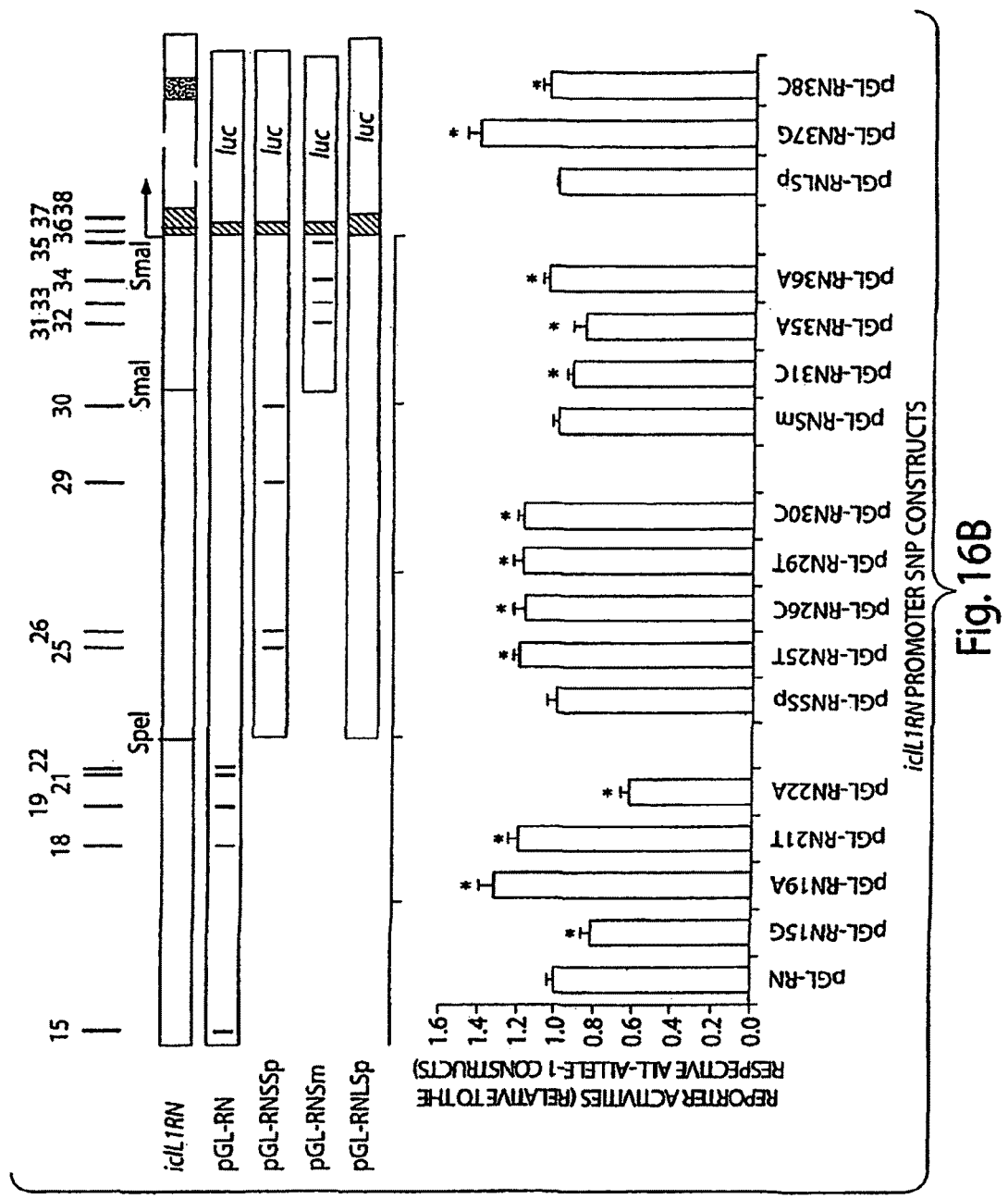

FIGS. 16 (A and B) shows the genotypes of IL-1RN SNP constructs (A) and selected reporter activities in a fibroblast cell line (B).

Figure 17:
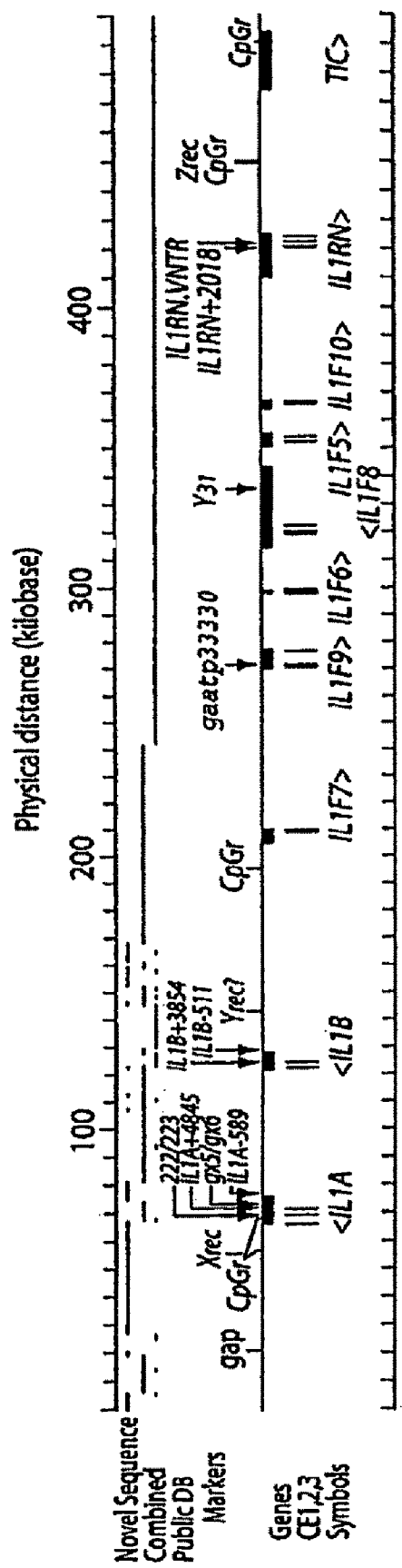

FIG. 17 shows a map of the IL-1 gene cluster. Scale bars (in kb) are provided above and below the data to aid alignments.

FIG. 18 (A-G) shows the alignment of the encoded sequence of the three common exons of the ten known members of the IL-1 family.

FIG. 19 shows the map positions of select polymorphic markers within the IL-1 gene cluster.

Figure 20:
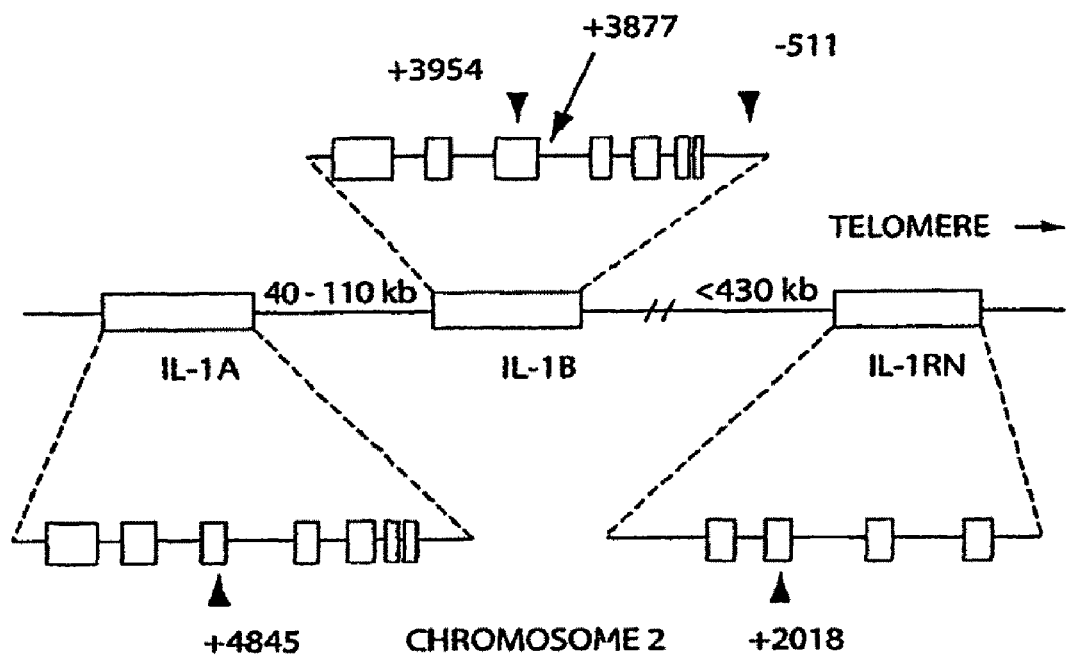

FIG. 20 is a schematic diagram showing the genes for IL-1α, IL-1β, and IL-1 receptor antagonist and SNPs therein.

Figure 21:
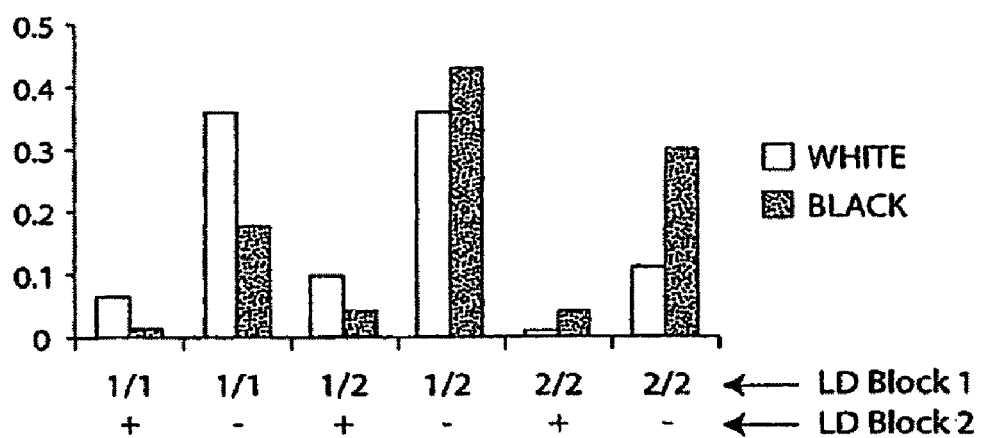

FIG. 21 is a bar graph showing composite genotype frequencies of study participants.

Figure 22:
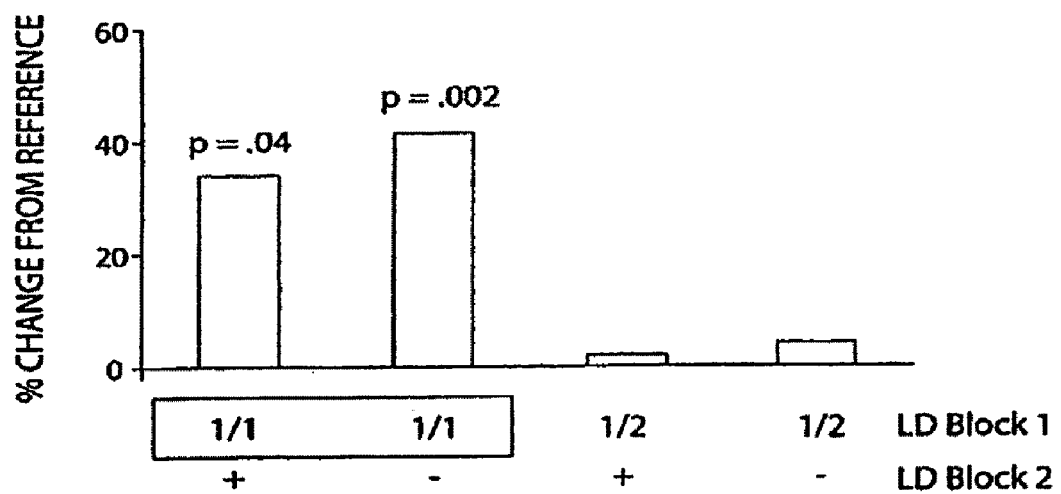

FIG. 22 is a bar graph showing IL-1β levels in Caucasians having composite genotypes.

Figure 23:
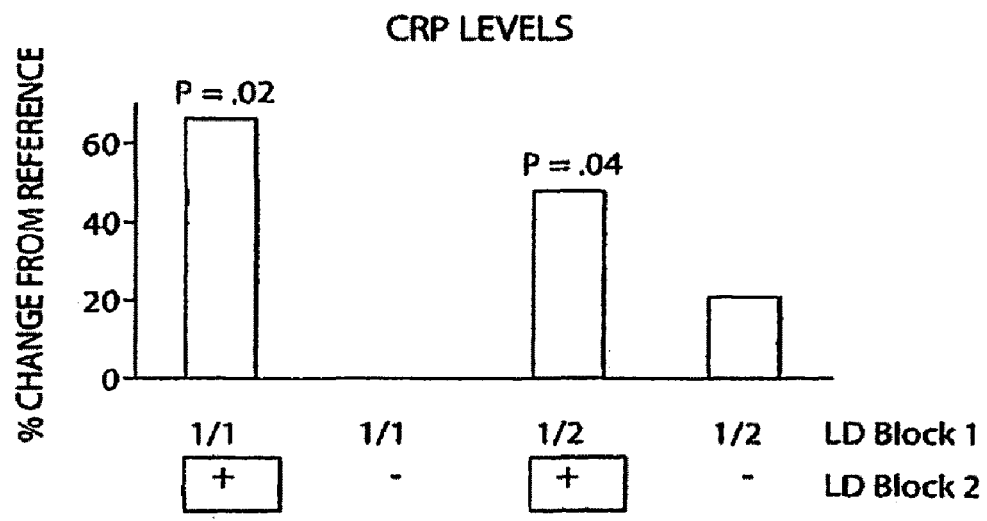

FIG. 23 is a bar graph showing C-reactive protein levels in Caucasians having composite genotypes.

Figure 24:
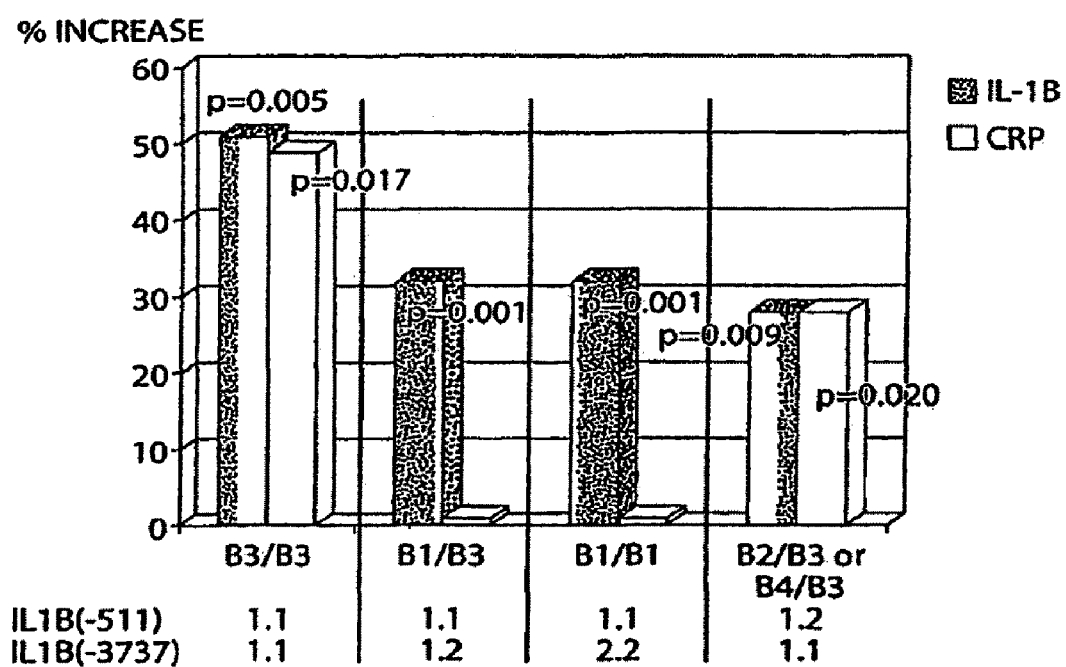

FIG. 24 is a bar graph showing the percent increase in IL-1β levels and C-reactive protein levels in Caucasians with various genotypes.

4. DETAILED DESCRIPTION OF THE INVENTION

4.1. General

Several homologs of the cytokine interleukin (IL)-1 gene map to the previously identified IL-1 gene cluster, but the public sequencing of the region has been relatively slow. We have therefore constructed a contig of the entire cluster and annotated it. In addition, novel human polymorphic loci in this gene cluster (including SNPs in IL-1A, IL-1B and IL-RN) and associated IL-1 haplotypes have been located and identified as summarized in FIGS. 1-11. The features of the invention are further demonstrated in the accompanying detailed description of the invention and examples which.

4.2. Definitions

For convenience, the meaning of certain terms and phrases employed in the specification, examples, and appended claims is provided below.

The term "allele" refers to the different sequence variants found at different polymorphic regions. For example, IL-1RN (VNTR) has at least five different alleles. The sequence variants may be single or multiple base changes, including without limitation insertions, deletions, or substitutions, or may be a variable number of sequence repeats.

The term "allelic pattern" refers to the identity of an allele or alleles at one or more polymorphic regions. For example, an allelic pattern may consist of a single allele at a polymorphic site, as for IL-1RN (VNTR) allele 1, which is an allelic pattern having at least one copy of IL-1RN allele 1 at the VNTR of the IL-1RN gene loci. Alternatively, an allelic pattern may consist of either a homozygous or heterozygous state at a single polymorphic site. For example, IL1-RN (VNTR) allele 2,2 is an allelic pattern in which there are two copies of the second allele at the VNTR marker of IL-1RN that corresponds to the homozygous IL-RN (VNTR) allele 2 state. Alternatively, an allelic pattern may consist of the identity of alleles at more than one polymorphic site.

The term "antibody" as used herein is intended to refer to a binding agent including a whole antibody or a binding fragment thereof which is specifically reactive with an IL-1 polypeptide. Antibodies can be fragmented using conventional techniques and the fragments screened for utility in the same manner as described above for whole antibodies. For example, F(ab)$_2$ fragments can be generated by treating an antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for an IL-1B polypeptide conferred by at least one CDR region of the antibody.

"Biological activity" or "bioactivity" or "activity" or "biological function", which are used interchangeably, for the purposes herein means an effector or antigenic function that is directly or indirectly performed by an IL-1 polypeptide (whether in its native or denatured conformation), or by any subsequence thereof. Biological activities include binding to a target peptide, e.g., an IL-1 receptor. An IL-1 bioactivity can be modulated by directly affecting an IL-1 polypeptide. Alternatively, an IL-1 bioactivity can be modulated by modulating the level of an IL-1 polypeptide, such as by modulating expression of an IL-1 gene.

As used herein the term "bioactive fragment of an IL-1 polypeptide" refers to a fragment of a full-length IL-1 polypeptide, wherein the fragment specifically mimics or antagonizes the activity of a wild-type IL-1 polypeptide. The bioactive fragment preferably is a fragment capable of interacting with an interleukin receptor.

The term "an aberrant activity", as applied to an activity of a polypeptide such as IL-1, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant IL-1 activity due to overexpression or underexpression of an IL-1 locus gene encoding an IL-1 locus polypeptide.

"Cells", "host cells" or "recombinant host cells" are terms used interchangeably herein to refer not only to the particular subject cell, but to the progeny or potential progeny of such a cell. Because certain modifications may occur in succeeding generations due to either mutation or environmental influences, such progeny may not, in fact be identical to the parent cell, but are still included within the scope of the term as used herein.

A "chimera," "mosaic," "chimeric mammal" and the like, refers to a transgenic mammal with a knock-out or knock-in construct in at least some of its genome-containing cells.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested. For example, the controls may be a sample of genomic DNA or a cloned portion of the IL-1 gene cluster. However, where the sample to be tested is genomic DNA, the control sample is preferably a highly purified sample of genomic DNA.

The phrase "diseases and conditions associated with IL-1 polymorphisms" refers to a variety of diseases or conditions, the susceptibility to which can be indicated in a subject based on the identification of one or more alleles within the IL-1 complex. Examples include: inflammatory or degenerative disease, including: Systemic Inflammatory Response (SIRS); Alzheimer's Disease (and associated conditions and symptoms including: chronic neuroinflammation, glial activation; increased microglia; neuritic plaque formation; and response to therapy); Amylotropic Lateral Sclerosis (ALS), arthritis (and associated conditions and symptoms including: acute joint inflammation, antigen-induced arthritis, arthritis associated with chronic lymphocytic thyroiditis, collagen-induced arthritis, juvenile chronic arthritis; juvenile rheumatoid arthritis, osteoarthritis, prognosis and *streptococcus*-induced arthritis), asthma (and associated conditions and symptoms, including: bronchial asthma; chronic obstructive airway disease; chronic obstructive pulmonary disease, juvenile asthma and occupational asthma); cardiovascular diseases (and associated conditions and symptoms, including atherosclerosis; autoimmune myocarditis, chronic cardiac hypoxia, congestive heart failure, coronary artery disease, cardiomyopathy and cardiac cell dysfunction, including: aortic smooth muscle cell activation; cardiac cell apoptosis; and immunomodulation of cardiac cell function; diabetes and associated conditions and symptoms, including autoimmune diabetes, insulin-dependent (Type 1) diabetes, diabetic periodontitis, diabetic retinopathy, and diabetic nephropathy); gastrointestinal inflammations (and related conditions and symptoms, including celiac disease, associated osteopenia, chronic colitis, Crohn's disease, inflammatory bowel disease and ulcerative colitis); gastric ulcers; hepatic inflammations, cholesterol gallstones and hepatic fibrosis, HIV infection (and associated conditions and symptoms, including degenerative responses, neurodegenerative responses, and HIV associated Hodgkin's Disease), Kawasaki's Syndrome (and associated diseases and conditions, including mucocutaneous lymph node syndrome, cervical lymphadenopathy, coronary artery lesions, edema, fever, increased leukocytes, mild anemia, skin peeling, rash, conjunctiva redness, thrombocytosis; multiple sclerosis, nephropathies (and associated diseases and conditions, including diabetic nephropathy, endstage renal disease, glomerulonephritis, Goodpasture's syndrome, hemodialysis survival and renal ischemic reperfusion injury), neurodegenerative diseases (and associated diseases and conditions, including acute neurodegeneration, induction of IL-I in aging and neurodegenerative disease, IL-1 induced plasticity of hypothalamic neurons and chronic stress hyperresponsiveness), Ophthalmopathies (and associated diseases and conditions, including diabetic retinopathy, Graves' Opthalmopathy, and uveitis, osteoporosis (and associated diseases and conditions, including alveolar, femoral, radial, vertebral or wrist bone loss or fracture incidence, postmenopausal bone loss, mass, fracture incidence or rate of bone loss), otitis media (adult or pediatric), pancreatis or pancreatic acinitis, periodontal disease (and associated diseases and conditions, including adult, early onset and diabetic); pulmonary diseases, including chronic lung disease, chronic sinusitis, hyaline membrane disease, hypoxia and pulmonary disease in SEDS; restenosis; rheumatism including rheumatoid arthritis, rheumatic aschoff bodies, rheumatic diseases and rheumatic myocarditis; thyroiditis including chronic lymphocytic thyroiditis; urinary tract infections including chronic prostatitis, chronic pelvic pain syndrome and urolithiasis. Immunological disorders, including autoimmune diseases, such as alopecia aerata, autoimmune myocarditis, Graves' disease, Graves' ophthalmopathy, lichen sclerosis, multiple sclerosis, psoriasis, systemic lupus erythematosus, systemic sclerosis, thyroid diseases (e.g. goiter and struma lymphomatosa (Hashimoto's thyroiditis, lymphadenoid goiter), sleep disorders and chronic fatigue syndrome and obesity (non-diabetic or associated with diabetes). Resistance to infectious diseases, such as Leishmaniasis, Leprosy, Lyme Disease, Lyme Carditis, malaria, cerebral malaria, meningititis, tubulointestitial nephritis associated with malaria), which are caused by bacteria, viruses (e.g. cytomegalovirus, encephalitis, Epstein-Barr Virus, Human Immunodeficiency Virus, Influenza Virus) or protozoans (e.g., *Plasmodium falciparum*, trypanosomes). Response to trauma, including cerebral trauma (including strokes and ischemias, encephalitis, encephalopathies, epilepsy, perinatal brain injury, prolonged febrile seizures, SEDS and subarachnoid hemorrhage), low birth weight (e.g. cerebral palsy), lung injury (acute hemorrhagic lung injury, Goodpasture's syndrome, acute ischemic reperfusion), myocardial dysfunction, caused by occupational and environmental pollutants (e.g. susceptibility to toxic oil syndrome silicosis), radiation trauma, and efficiency of wound healing responses (e.g. burn or thermal wounds, chronic wounds, surgical wounds and spinal cord injuries). Susceptibility to neoplasias, including breast cancer associated osteolytic metastasis, cachexia, colorectal cancer, hyperproliferative diseases, Hodgkin's disease, leukemias, lymphomas, metabolic diseases and tumors, metastases, myeolomas, and various cancers (including breast prostate ovarian, colon, lung, etc), anorexia and cachexia. Hormonal regulation including fertility/fecundity, likelihood of a pregnancy, incidence of preterm labor, prenatal and neonatal complications including preterm low birth weight, cerebral palsy, septicemia, hypothyroxinemia, oxygen dependence, cranial abnormality, early onset menopause. A subject's response to transplant (rejection or acceptance), acute phase response (e.g. febrile response), general inflammatory response, acute respiratory distress response, acute systemic inflammatory response, wound healing, adhesion, immunoinflammatory response, neuroendocrine response, fever development and resistance, acute-phase response, stress response, disease susceptibility, repetitive motion stress, tennis elbow, and pain management and response.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

The term "haplotype" as used herein is intended to refer to a set of alleles that are inherited together as a group (are in linkage disequilibrium) at statistically significant levels ($P_{corr}$<0.05). As used herein, the phrase "an IL-1 haplotype" refers to a haplotype in the IL-1 loci. An IL-1 inflammatory or proinflammatory haplotype refers to a haplotype that is indicative of increased agonist and/or decreased antagonist activities.

The terms "IL-1 gene cluster" and "IL-1 loci" as used herein include all the nucleic acid at or near the 2q13 region of chromosome 2, including at least the IL-1A, IL-1B and IL-1RN genes and any other linked sequences. (Nicklin et al., Genomics 19:382-84, 1994). The terms "IL-1A", "IL-1B", and "IL-1RN" as used herein refer to the genes coding for IL-1, IL-1, and IL-1 receptor antagonist, respectively. The gene accession number for IL-1A, IL-1B, and IL-1RN are X03833, X04500, and X64532, respectively.

"L-1 functional mutation" refers to a mutation within the IL-1 gene cluster that results in an altered phenotype (i.e. effects the function of an IL-1 gene or protein). Examples include: IL-1A(+4845) allele 2, IL-1B (+3954) allele 2, IL-1B (+6912) allele 2 and IL-1RN (+2018) allele 2.

"IL-1X (Z) allele Y" refers to a particular allelic form, designated Y, occurring at an IL-1 locus polymorphic site in gene X, wherein X is IL-1A, B, or RN and positioned at or near nucleotide Z, wherein nucleotide Z is numbered relative to the major transcriptional start site, which is nucleotide +1, of the particular IL-1 gene X. As further used herein, the term "IL-1X allele (Z)" refers to all alleles of an IL-1 polymorphic site in gene X positioned at or near nucleotide Z. For example, the term "IL-1RN (+2018) allele" refers to alternative forms of the IL-1RN gene at marker +2018. "IL-1RN (+2018) allele 1" refers to a form of the IL-1RN gene which contains a cytosine (C) at position +2018 of the sense strand. Clay et al., Hum. Genet. 97:723-26, 1996. "IL-1RN (+2018) allele 2" refers to a form of the IL-1RN gene which contains a thymine (T) at position +2018 of the plus strand. When a subject has two identical IL-1RN alleles, the subject is said to be homozygous, or to have the homozygous state. When a subject has two different IL-1RN alleles, the subject is said to be heterozygous, or to have the heterozygous state. The term "IL-1RN (+2018) allele 2,2" refers to the homozygous IL-1 RN (+2018) allele 2 state. Conversely, the term "IL-1RN (+2018) allele 1,1" refers to the homozygous IL-1 RN (+2018) allele 1 state. The term "IL-1RN (+2018) allele 1,2" refers to the heterozygous allele 1 and 2 state.

The term "IL-1 phenotype" is meant to refer to any phenotype resulting from an IL-1 gene locus genetic identity—i.e. including increased and decreased predispositions to an inflammatory disease or condition as well as a "normal" (e.g. average or "wild type") associated likelihood of an inflammatory disease or disorder.

"IL-1 related" as used herein is meant to include all genes related to the human IL-1 locus genes on human chromosome 2 (2q 12-14). These include IL-1 genes of the human IL-1 gene cluster located at chromosome 2 (2q 13-14) which include, the IL-1A gene which encodes interleukin-1α, the IL-1B gene which encodes interleukin-1β, and the IL-1RN (or IL-1ra) gene which encodes the interleukin-1 receptor antagonist. Furthermore these IL-1 related genes include the type I and type II human IL-1 receptor genes located on human chromosome 2 (2q12) and their mouse homologs located on mouse chromosome 1 at position 19.5 cM. Interleukin-1α, interleukin-1β, and interleukin-1RN are related in so much as they all bind to IL-1 type I receptors, however only interleukin-1α and interleukin-1β are agonist ligands which activate IL-1 type I receptors, while interleukin-1RN is a naturally occurring antagonist ligand. Where the term "IL-1" is used in reference to a gene product or polypeptide, it is meant to refer to all gene products encoded by the interleukin-1 locus on human chromosome 2 (2q 12-14) and their corresponding homologs from other species or functional variants thereof. The term IL-1 thus includes secreted polypeptides which promote an inflammatory response, such as IL-1 a and IL-1β, as well as a secreted polypeptide which antagonize inflammatory responses, such as IL-1 receptor antagonist and the IL-1 type II (decoy) receptor.

An "IL-1 receptor" or "IL-1R" refers to various cell membrane bound protein receptors capable of binding to and/or transducing a signal from an IL-1 locus-encoded ligand. The term applies to any of the proteins which are capable of binding interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Examples include the human and murine IL-1 receptors described in U.S. Pat. No. 4,968,607. The term "IL-1 nucleic acid" refers to a nucleic acid encoding an IL-1 protein.

Figure 1:
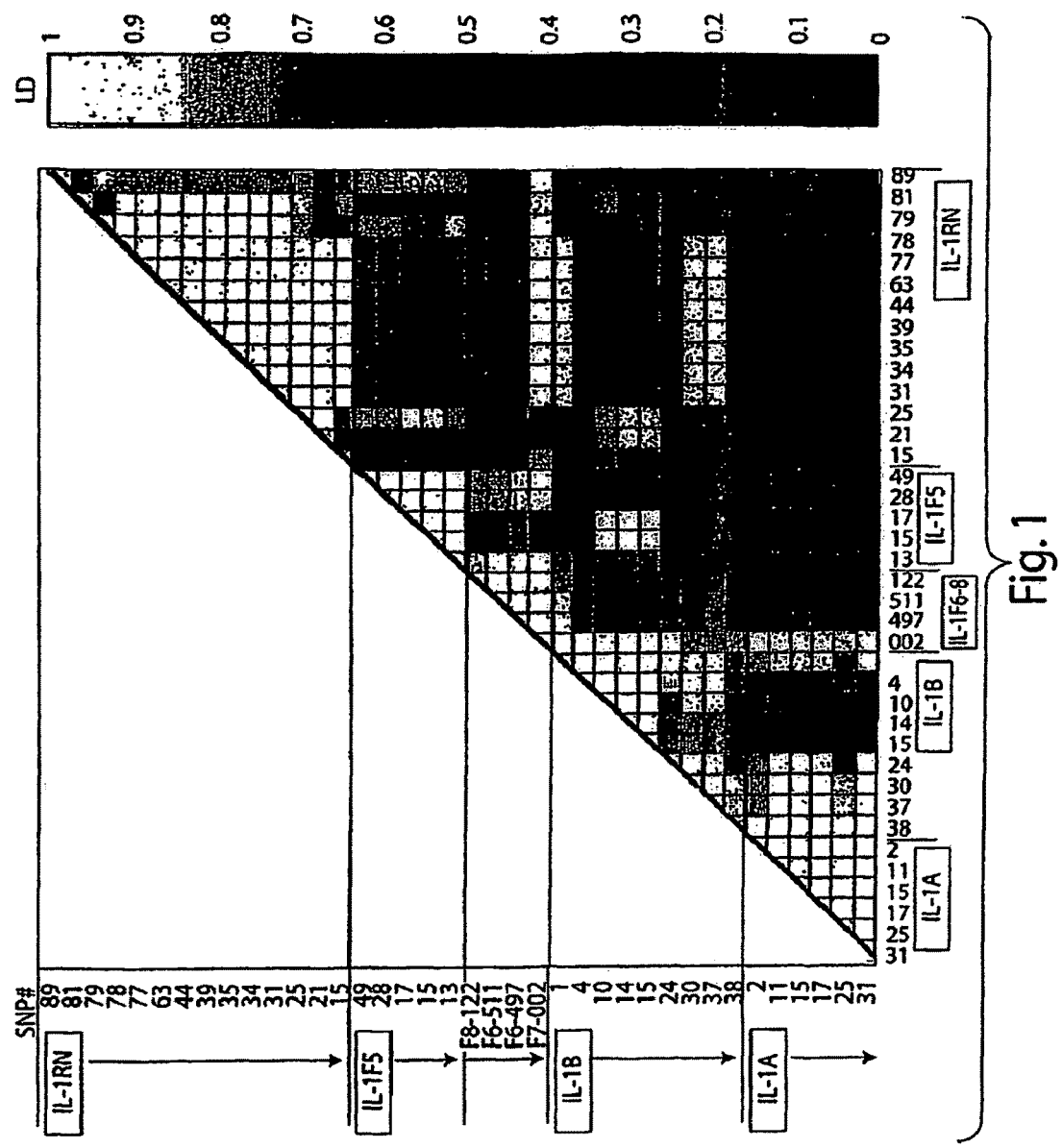
FIG. 1 represents schematically the linkage disequilibrium of representative SNPs throughout the IL-1 gene cluster locus.
Figure 5A:
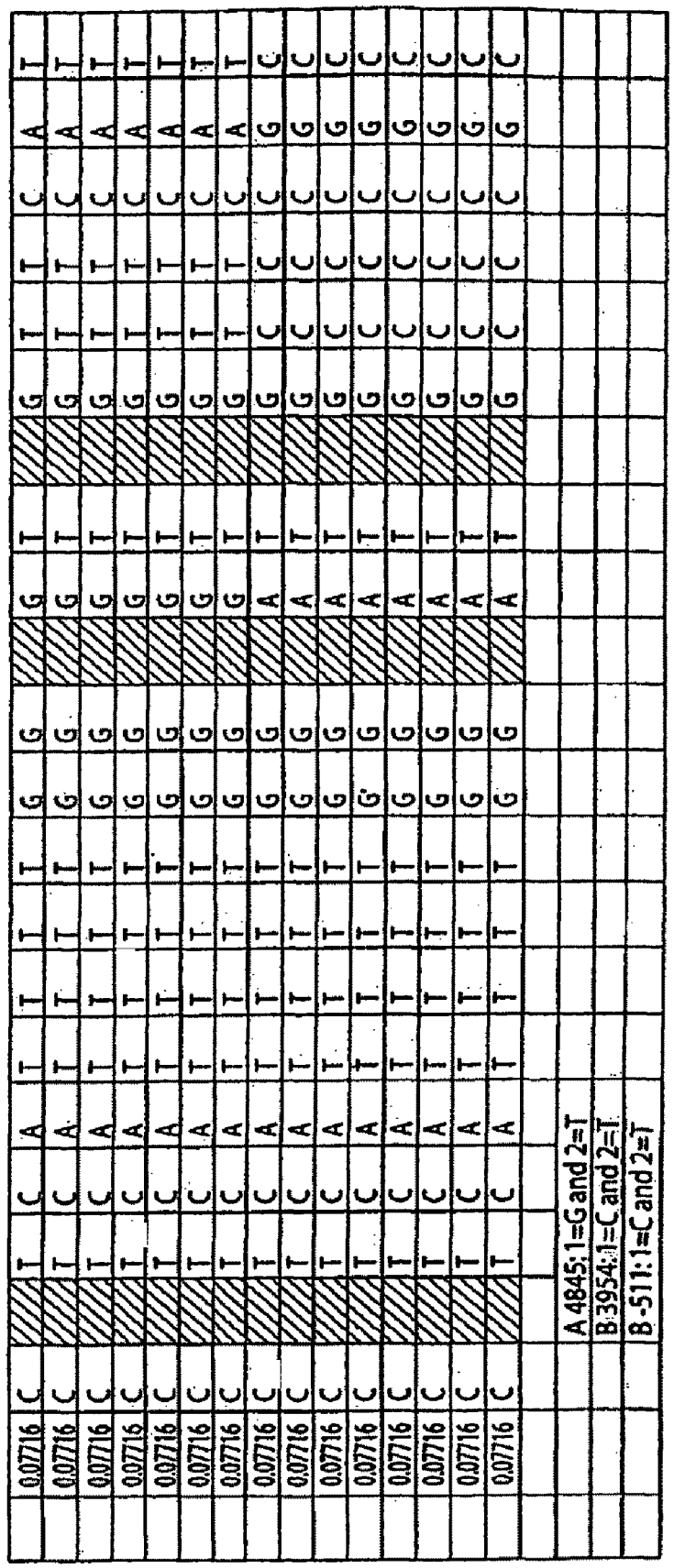
FIGS. 5 (A and B) shows the organization of SNPs of IL-1 haplotype pattern 3 (hap 3) (G-C-C)=1_1_1).

An "IL-1 polypeptide" and "IL-1 protein" are intended to encompass polypeptides comprising the amino acid sequence encoded by the IL-1 genomic DNA sequences shown in FIGS. 1, 2, and 3, or fragments thereof, and homologs thereof and include agonist and antagonist polypeptides.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

"Decreased risk" refers to a statistically lower frequency of occurrence of the disease or condition in an individual carrying a particular polymorphic allele in comparison to the frequency of occurrence of the disease or condition in a member of a population that does not carry the particular polymorphic allele or in the population as a whole.

The term "interact" as used herein is meant to include detectable relationships or associations (e.g. biochemical interactions) between molecules, such as interactions between protein-protein, protein-nucleic acid, nucleic acid-nucleic acid and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject IL-1 polypeptides preferably includes no more than 10 kilobases (kb) of nucleic acid sequence which naturally immediately flanks the IL-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g, based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell. In a simple example, the knock-out construct is comprised of a gene, such as the IL-1RN gene, with a deletion in a critical portion of the gene, so that active protein cannot be expressed therefrom. Alternatively, a number of termination codons can be added to the native gene to cause early termination of the protein or an intron junction can be inactivated. In a typical knock-out construct, some portion of the gene is replaced with a selectable marker (such as the neo gene) so that the gene can be represented as follows: IL-1RN 5'/neo/IL-1RN 3', where IL-1RN5' and IL-1RN 3', refer to genomic or cDNA sequences which are, respectively, upstream and downstream relative to a portion of the IL-1RN gene and where neo refers to a neomycin resistance gene. In another knock-out construct, a second selectable marker is added in a flanking position so that the gene can be represented as: IL-1RN/neo/IL-1RN/TK, where TK is a thymidine kinase gene which can be added to either the IL-1RN5' or the IL-1RN3' sequence of the preceding construct and which further can be selected against (i.e. is a negative selectable marker) in appropriate media. This two-marker construct allows the selection of homologous recombination events, which removes the flanking TK marker, from non-homologous recombination events which typically retain the TK sequences. The gene deletion and/or replacement can be from the exons, introns, especially intron junctions, and/or the regulatory regions such as promoters.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage disequilibrium". The cause of linkage disequilibrium is often unclear. It can be due to selection for certain allele combinations or to recent admixture of genetically heterogeneous populations. In addition, in the case of markers that are very tightly linked to a disease gene, an association of an allele (or group of linked alleles) with the disease gene is expected if the disease mutation occurred in the recent past, so that sufficient time has not elapsed for equilibrium to be achieved through recombination events in the specific chromosomal region. When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern. An example of linkage disequilibrium is that which occurs between the alleles at the IL-1RN (+2018) and IL-1RN (VNTR) polymorphic sites. The two alleles at IL-1RN (+2018) are 100% in linkage disequilibrium with the two most frequent alleles of IL-1RN (VNTR), which are allele 1 and allele 2.

The term "marker" refers to a sequence in the genome that is known to vary among 1 individuals. For example, the IL-1RN gene has a marker that consists of a variable number of tandem repeats (VNTR).

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

A "non-human animal" of the invention includes mammals such as rodents, non-human primates, sheep, dogs, cows, goats, etc. amphibians, such as members of the *Xenopus* genus, and transgenic avians (e.g. chickens, birds, etc.). The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any member of the class Mammalia, except for humans.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs (e.g. peptide nucleic acids) and as applicable to the embodiment being described, single (sense or antisense) and double-stranded polynucleotides.

The term "nutraceutical", as used herein includes the FDA definitions of foods and dietary supplements that may be of value in treating a disease or disorder—particularly a disease or disorder associated with an inflammatory disease. Accordingly, "nutracteuticals" include nutritional ingredients that can be used to achieve health benefits. These ingredients may be in "foods"—i.e. "functional foods" or in dietary supplements. In October 1994, the Dietary Supplement Health and Education Act ("DSHEA") was signed into law. DSHEA acknowledges that millions of consumers believe that dietary supplements may provide health benefits. Congress's intent in passing it was to strike a balance between consumer access to dietary supplements and FDA's authority to act against supplements that present safety problems or bear false or misleading labeling. DSHEA creates a new regulatory framework for the safety and labeling of dietary supplements. The FDA is committed to enforcing DSHEA in a manner that effectuates DSHEA. Accordingly, "nutraceuticals," as used herein, includes dietary supplements known in the art (e.g. vitamins, minerals, herbs and other supplements) which are ingested and are intended to supplement the diet and include a "dietary ingredient." Dietary ingredients may include vitamins, minerals, herbs or other botanicals, amino acids, and dietary substances such as enzymes. Dietary ingredients also can be metabolites, constituents, extracts, concentrates, or combinations of these ingredients. Nutraceutical supplements come in forms including tablets, capsules, liquids, and bars.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

The term "propensity to disease," also "predisposition" or "susceptibility" to disease or any similar phrase, means that certain alleles are hereby discovered to be associated with or predictive of a subject's incidence of developing a particular disease (e.g. a vascular disease). The alleles are thus overrepresented in frequency in individuals with disease as compared to healthy individuals. Thus, these alleles can be used to predict disease even in pre-symptomatic or pre-diseased individuals.

"Small molecule" as used herein, is meant to refer to a composition, which has a molecular weight of less than about 5 kD and most preferably less than about 4 kD. Small molecules can be nucleic acids, peptides, peptidomimetics, carbohydrates, lipids or other organic or inorganic molecules.

As used herein, the term "specifically hybridizes" or "specifically detects" refers to the ability of a nucleic acid molecule to hybridize to at least approximately 6 consecutive nucleotides of a sample nucleic acid.

"Transcriptional regulatory sequence" is a generic term used throughout the specification to refer to DNA sequences, such as initiation signals, enhancers, and promoters, which induce or control transcription of protein coding sequences with which they are operably linked.

As used herein, the term "transgene" means a nucleic acid sequence (encoding, e.g., one of the IL-1 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of an IL-1 polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques. The term is intended to include all progeny generations. Thus, the founder animal and all F1, F2, F3, and so on, progeny thereof are included.

The term "treating" as used herein is intended to encompass curing as well as ameliorating at least one symptom of a condition or disease.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.3 Detection of Alleles

Many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic-occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in an individual. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

Several methods have been developed to facilitate analysis of single nucleotide polymorphisms. In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650, 840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GB A™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

For mutations that produce premature termination of protein translation, the protein truncation test (PTT) offers an efficient diagnostic approach (Roest, et. al., (1993) Hum. Mol Genet. 2:1719-21; van der Luijt, et. al., (1994) Genomics 20:1-4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when, the target region of interest is derived from a single exon.

Any cell type or tissue may be utilized to obtain nucleic acid samples for use in the diagnostics described herein. In a preferred embodiment, the DNA sample is obtained from a bodily fluid, e.g, blood, obtained by known techniques (e.g. venipuncture) or saliva. Alternatively, nucleic acid tests can be performed on dry samples (e.g. hair or skin). When using RNA or protein, the cells or tissues that may be utilized must express an IL-1 gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of at least one allele of an IL-1 proinflammatory haplotype and having about 5, 10, 20, 25, or 30 nucleotides around the mutation or polymorphic region. In a preferred embodiment of the invention, several probes capable of hybridizing specifically to other allelic variants involved in a restenosis are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., 1990, Proc. Natl. Acad. Sci. USA 87:1874-1878), transcriptional amplification system (Kwoh, D. Y. et al., 1989, Proc. Natl. Acad. Sci. USA 86:1173-1177), and Q-Beta Replicase (Lizardi, P. M. et al., 1988, Bio/Technology 6:1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of an IL-1 proinflammatory haplotype under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, the allele of an IL-1 proinflammatory haplotype is identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety of sequencing reactions known in the art can be used to directly sequence the allele. Exemplary sequencing reactions include those based on techniques developed by Maxim and Gilbert (((1977) Proc. Natl. Acad Sci USA 74:560) or Sanger (Sanger et al (1977) Proc. Nat. Acad. Sci USA 74:5463). It is also contemplated that any of a variety of automated sequencing procedures may be utilized when performing the subject assays (see, for example Biotechniques (1995) 19:448), including sequencing by mass spectrometry (see, for example PCT publication WO 94/16101; Cohen et al. (1996) Adv Chromatogr 36:127-162; and Griffin et al. (1993) Appl Biochem Biotechnol 38:147-159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) Science 230:1242). In general, the art technique of "mismatch cleavage" starts by providing heteroduplexes formed by hybridizing (labeled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzyraticaliy digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl. Acad Sci USA 85:4397; and Saleeba et al (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on an allele of an IL-1 locus haplotype is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify an IL-1 locus allele. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125-144; and Hayashi (1992) Genet Anal Tech App 19:73-79). Single-stranded DNA fragments of sample and control IL-1 locus alleles are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of alleles in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265: 12753).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) Nature 324:163); Saiki et al (1989) Proc. Natl. Acad, Sci USA 86:6230), Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) Nucleic Acids Res. 17:2437-2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation: to create cleavage-based detection (Gasparini et al (1992) Mol. Cell. Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al. ((1988) Science 241:1077-1080). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923-27). In this method, PCR is used to achieve the exponential amplification of target DNA, which is then detected using OLA.

Several techniques based on this OLA method have been developed and can be used to detect alleles of ah IL-1 locus haplotype. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microliter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Another embodiment of the invention is directed to kits for detecting a predisposition for developing a restenosis. This kit may contain one or more oligonucleotides, including 5' and 3' oligonucleotides that hybridize 5' and 3' to at least one allele of an IL-1 locus haplotype. PCR amplification oligonucleotides should hybridize between 25 and 2500 base pairs apart, preferably between about 100 and about 500 bases apart, in order to produce a PCR product of convenient size for subsequent analysis.

Particularly preferred primers included nucleotide sequences described in FIGS. 8-11. The design of additional oligonucleotides for use in the amplification and detection of IL-1 polymorphic alleles by the method of the invention is facilitated by the availability of both updated sequence information from human chromosome 2q13—which contains the human IL-1 locus, and updated human polymorphism information available for this locus. For example, the DNA sequence for the IL-1A, IL-1B and IL-1RN is shown in FIGS. 1 (GenBank Accession No. X03833), 2 (GenBank Accession No. X04500) and 3 (GenBank Accession No. X64532) respectively. Suitable primers for the detection of a human polymorphism in these genes can be readily designed using this sequence information and standard techniques known in the art for the design and optimization of primers sequences. Optimal design of such primer sequences can be achieved, for example, by the use of commercially available primer selection programs such as Primer 2.1, Primer 3 or GeneFisher (See also, Nicklin M. H. J., Weith A. Duff G. W., "A Physical Map of the Region Encompassing the Human Interleukin-1α, interleukin-1β, and Interleukin-1 Receptor Antagonist Genes" Genomics 19: 382 (1995); Nothwang H. G., et al. "Molecular Cloning of the Interleukin-1 gene Cluster: Construction of an Integrated YAC/PAC Contig and a partial transcriptional Map in the Region of Chromosome 2q13" Genomics 41:370 (1997); Clark, et al. (1986) Nucl. Acids. Res., 14:7897-7914 [published erratum appears in Nucleic Acids Res., 15:868 (1987) and the Genome Database (GDB) project at the URL http://www.gdb.org).

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moieties, metal binding moieties, antigen or antibody moieties, and the like.

The kit may, optionally, also include DNA sampling means. DNA sampling means are well known to one of skill in the art and can include, but not be limited to substrates, such as filter papers, the AmpliCard™ (University of Sheffield, Sheffield, England S10 2JF; Tarlow, J W, et al., J of Invest Dermatol. 103:387-389 (1994)) and the like; DNA purification reagents such as Nucleon™ kits, lysis buffers, proteinase solutions and the like; PCR reagents, such as 10× reaction buffers, thermostable polymerase, dNTPs, and the like; and allele detection means such as the HinfI restriction enzyme, allele specific oligonucleotides, degenerate oligonucleotide primers for nested PCR from dried blood.

4.4. Pharmacogenomics

Knowledge of the particular alleles associated with a susceptibility to developing a particular disease or condition, alone or in conjunction with information on other genetic defects contributing to the particular disease or condition allows a customization of the prevention or treatment in accordance with the individual's genetic profile, the goal of "pharmacogenomics". Thus, comparison of an individual's IL-1 profile to the population profile for a vascular disorder, permits the selection or design of drugs or other therapeutic regimens that are expected to be safe and efficacious for a particular patient or patient population (i.e., a group of patients having the same genetic alteration).

In addition, the ability to target populations expected to show the highest clinical benefit, based on genetic profile can enable: 1) the repositioning of already marketed drugs; 2) the rescue of drug candidates whose clinical development has been discontinued as a result of safety or efficacy limitations, which are patient subgroup-specific; and 3) an accelerated and less costly development for candidate therapeutics and more optimal drug labeling (e.g. since measuring the effect of various doses of an agent on the causative mutation is useful for optimizing effective dose).

The treatment of an individual with a particular therapeutic can be monitored by determining protein (e.g. IL-1α, IL-1β, or IL-1Ra), mRNA and/or transcriptional level. Depending on the level detected, the therapeutic regimen can then be maintained or adjusted (increased or decreased in dose). In a preferred embodiment, the effectiveness of treating a subject with an agent comprises the steps of: (i) obtaining a preadministration sample from a subject prior to administration of the agent; (ii) detecting the level or amount of a protein, mRNA or genomic DNA in the preadministration sample; (iii) obtaining one or more post-administration samples from the subject; (iv) detecting the level of expression or activity of the protein, mRNA or genomic DNA in the post-administration sample; (v) comparing the level of expression or activity of the protein, mRNA or genomic DNA in the preadministration sample with the corresponding protein, mRNA or genomic DNA in the postadministration sample, respectively; and (vi) altering the administration of the agent to the subject accordingly.

Cells of a subject may also be obtained before and after administration of a therapeutic to detect the level of expression of genes other than an IL-1 gene to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

4.5. Therapeutics For Diseases and Conditions Associated with IL-1 Polymorphisms Therapeutic for diseases or conditions associated with an IL-1 polymorphism or haplotype refers to any agent or therapeutic regimen (including pharmaceuticals, nutraceuticals and surgical means) that prevents or postpones the development of or alleviates the symptoms of the particular disease or condition in the subject. The therapeutic can be a polypeptide, peptidomimetic, nucleic acid or other inorganic or organic molecule, preferably a "small molecule" including vitamins, minerals and other nutrients. Preferably the therapeutic can modulate at least one activity of an IL-1 polypeptide, e.g., interaction with a receptor, by mimicking or potentiating (agonizing) or inhibiting (antagonizing) the effects of a naturally-occurring polypeptide. An agonist can be a wild-type protein or derivative thereof having at least one bioactivity of the wild-type, e.g., receptor binding activity. An agonist can also be a compound that upregulates expression of a gene or which increases at least one bioactivity of a protein. An agonist can also be a compound which increases the interaction of a polypeptide with another molecule, e.g., a receptor. An antagonist can be a compound which inhibits or decreases the interaction between a protein and another molecule, e.g., a receptor or an agent that blocks signal transduction or post-translation processing (e.g., IL-1 converting enzyme (ICE) inhibitor). Accordingly, a preferred antagonist is a compound which inhibits or decreases binding to a receptor and thereby blocks subsequent activation of the receptor. An antagonist can also be a compound that downregulates expression of a gene or which reduces the amount of a protein present. The antagonist can be a dominant negative form of a polypeptide, e.g., a form of a polypeptide which is capable of interacting with a target peptide, e.g., a receptor, but which does not promote the activation of the receptor. The antagonist can also be a nucleic acid encoding a dominant negative form of a polypeptide, an antisense nucleic acid, or a ribozyme capable of interacting specifically with an RNA. Yet other antagonists are molecules which bind to a polypeptide and inhibit its action. Such molecules include peptides, e.g., forms of target peptides which do not have biological activity, and which inhibit binding to receptors. Thus, such peptides will bind to the active site of a protein and prevent it from interacting with target peptides. Yet other antagonists include antibodies that specifically interact with an epitope of a molecule, such that binding interferes with the biological function of the polypeptide. In yet another preferred embodiment, the antagonist is a small molecule, such as a molecule capable of inhibiting the interaction between a polypeptide and a target receptor. Alternatively, the small molecule can function as an antagonist by interacting with sites other than the receptor binding site.

Modulators of IL-1 (e.g. IL-1α, IL-1β or IL-1 receptor antagonist) or a protein encoded by a gene that is in linkage disequilibrium with an IL-1 gene can comprise any type of compound, including a protein, peptide, peptidomimetic, small molecule, or nucleic acid. Preferred agonists include nucleic acids (e.g. encoding an IL-1 protein or a gene that is up- or down-regulated by an IL-1 protein), proteins (e.g. IL-1 proteins or a protein that is up- or down-regulated thereby) or a small molecule (e.g. that regulates expression or binding of an IL-1 protein). Preferred antagonists, which can be identified, for example, using the assays described herein, include nucleic acids (e.g. single (antisense) or double stranded (triplex) DNA or PNA and ribozymes), protein (e.g. antibodies) and small molecules that act to suppress or inhibit IL-1 transcription and/or protein activity.

4.6. Effective Dose and Formulations and Use

Toxicity and therapeutic efficacy of such compounds can be determined by standard pharmaceutical procedures in cell cultures or experimental animals, e.g., for determining The $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.7. Assays to Identify Therapeutics

Based on the identification of mutations that cause or contribute to the development of a disease or disorder that is associated with an IL-1 polymorphism or haplotype, the invention further features cell-based or cell free assays for identifying therapeutics. In one embodiment, a cell expressing an IL-1 receptor, or a receptor for a protein that is encoded by a gene which is in linkage disequilibrium with an IL-1 gene, on the outer surface of its cellular membrane is incubated in the presence of a test compound alone or in the presence of a test compound and another protein and the interaction between the test compound and the receptor or between the protein (preferably a tagged protein) and the receptor is detected, e.g., by using a microphysiometer (McConnell et al. (1992) Science 257:1906). An interaction between the receptor and either the test compound or the protein is detected by the microphysiometer as a change in the acidification of the medium. This assay system thus provides a means of identifying molecular antagonists which, for example, function by interfering with protein-receptor interactions, as well as molecular agonist which, for example, function by activating a receptor.

Cellular or cell-free assays can also be used to identify compounds which modulate expression of an IL-1 gene or a gene in linkage disequilibrium therewith, modulate translation of an mRNA, or which modulate the stability of an mRNA or protein. Accordingly, in one embodiment, a cell which is capable of producing an IL-1, or other protein is incubated with a test compound and the amount of protein produced in the cell medium is measured and compared to that produced from a cell which has not been contacted with the test compound. The specificity of the compound vis a vis the protein can be confirmed by various control analysis, e.g., measuring the expression of one or more control genes. In particular, this assay can be used to determine the efficacy of antisense, ribozyme and triplex compounds.

Cell-free assays can also be used to identify compounds which are capable of interacting with a protein, to thereby modify the activity of the protein. Such a compound can, e.g., modify the structure of a protein thereby effecting its ability to bind to a receptor. In a preferred embodiment, cell-free assays for identifying such compounds consist essentially in a reaction mixture containing a protein and a test compound or a library of test compounds in the presence or absence of a binding partner. A test compound can be, e.g., a derivative of a binding partner, e.g., a biologically inactive target peptide, or a small molecule.

Accordingly, one exemplary screening assay of the present invention includes the steps of contacting a protein or functional fragment thereof with a test compound or library of test compounds and detecting the formation of complexes. For detection purposes, the molecule can be labeled with a specific marker and the test compound or library of test compounds labeled with a different-marker. Interaction of a test compound with a protein or fragment thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the protein or functional fragment thereof is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an IL-1 or other protein, (ii) an appropriate receptor, and (iii) a test compound; and (b) detecting interaction of the protein and receptor. A statistically significant change (potentiation or inhibition) in the interaction of the protein and receptor in the presence of the test compound, relative to the interaction in the absence of the test compound, indicates a potential antagonist (inhibitor). The compounds of this assay can be contacted simultaneously. Alternatively, a protein can first be contacted with a test compound for an appropriate amount of time, following which the receptor is added to the reaction mixture. The efficacy of the compound can be assessed by generating dose response curves from data obtained using various concentrations of the test compound. Moreover, a control assay can also be performed to provide a baseline for comparison.

Complex formation between a protein and receptor may be detected by a variety of techniques. Modulation of the formation of complexes can be quantitated using, for example, detectably labeled proteins such as radiolabeled, fluorescently labeled, or enzymatically labeled proteins or receptors, by immunoassay, or by chromatographic detection.

Typically, it will be desirable to immobilize either the protein or the receptor to facilitate separation of complexes from uncomplexed forms of one or both of the proteins, as well as to accommodate automation of the assay. Binding of protein and receptor can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the receptor, e.g. an $^{35}$S-labeled receptor, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PACE, and the level of protein or receptor found in the bead fraction quantitated from the gel using standard electrophoretic techniques such as described in the appended examples. Other techniques for immobilizing proteins on matrices are also available for use in the subject assay. For instance, either protein or receptor can be immobilized utilizing conjugation of biotin and streptavidin. Transgenic animals can also be made to identify agonists and antagonists or to confirm the safety and efficacy of a candidate therapeutic. Transgenic animals of the invention can include non-human animals containing a restenosis causative mutation under the control of an appropriate endogenous promoter or under the control of a heterologous promoter.

The transgenic animals can also be animals containing a transgene, such as reporter gene, under the control of an appropriate promoter or fragment thereof. These animals are useful, e.g., for identifying drugs that modulate production of an IL-1 protein, such as by modulating gene expression. Methods for obtaining transgenic non-human animals are well known in the art. In preferred embodiments, the expression of the restenosis causative mutation is restricted to specific subsets of cells, tissues or developmental stages utilizing, for example, cis-acting sequences that control expression in the desired pattern. In the present invention, such mosaic expression of a protein can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the mutation in certain spatial patterns. Moreover, temporal patterns of expression can be provided by, for example, conditional recombination systems or prokaryotic transcriptional regulatory sequences. Genetic techniques, which allow for the expression of a mutation can be regulated via site-specific genetic manipulation in vivo, are known to those skilled in the art.

The transgenic animals of die present invention all include within a plurality of their cells a causative mutation transgene of the present invention, which transgene alters the phenotype of the "host cell". In an illustrative embodiment, either the cre/loxP recombinase system of bacteriophage P1 (Lakso et al. (1992) PNAS 89:6232-6236; Orban et al. (1992) PNAS 89:6861-6865) or the FLP recombinase system of *Saccharomyces cerevisiae* (O'Gorman et al. (1991) Science 251:1351-1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J Biol. Chem. 259:1509-1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the causative mutation transgene can be regulated via control of recombinase expression.

Use of the cre/loxP system to regulate expression of a causative mutation transgene requires the construction of a transgenic animal containing transgenes encoding both the Cre recombinase and the subject protein. Animals containing both the Cre recombinase and the restenosis causative mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/J6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment the transgene construct is introduced into a single stage embryo. The zygote is the best target for microinjection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al. (1985) PNAS 82:4438-4442). As a consequence, all cells of the transgenic animal will carry the incorporated transgene. This will in general also be reflected in efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of offspring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. Further, in such embodiments the sequence will be attached to a transcriptional control element e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) Nature 292:154-156; Bradley et al. (1984) Nature 309:255-258; Gossler et al. (1986) PNAS 83:9065-9069; and Robertson et al. (1986) Nature 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468-1474.

The present invention is further illustrated by the following examples which should not be construed as limiting in any way. The contents of all cited references (including literature references, issued patents, published patent applications as cited throughout this application) are hereby expressly incorporated by reference. The practice of the present invention will employ, unless otherwise indicated, conventional techniques that are within the skill of the art. Such techniques are explained fully in the literature. See, for example, Molecular Cloning A Laboratory Manual, (2nd ed., Sambrook; Fritsch and Maniatis, eds., Cold Spring Harbor Laboratory Press: 1989); DNA Cloning, Volumes I and II (D. N. Glover ed., 1985); Oligonucleotide Synthesis (M. J. Gait ed., 1984); U.S. Pat. No. 4,683,195; U.S. Pat. No. 4,683,202; and Nucleic Acid Hybridization (B. D. Hames & S. J. Higgins eds., 1984).

5. EXAMPLES

The following examples further support, but do not exclusively represent, preferred embodiments of the present invention.

Example 1

IL-1 Gene Locus Mapping and Characterization

The six novel genes encoding proteins with the IL-1 fold have been identified. The classical family are involved in inflammatory signaling. Clone-based and radiation hybrid mapping has placed all six novel genes close to or within the same cluster as the three original gene family members (IL1A, IL1B, IL1RN), in a ~400 kb interval on chromosome 2. We have combined the incomplete public database sequence with our own sequence to generate a reference sequence and map that encompasses all of the novel genes, allowing determination of the gene structures, precise localisation of exons and determination of distances between conventional SNP and microsatellite markers. Gene order from centromere to telomere is IL1A-IL1B-IL1F7-IL1F9-IL1F6-IL1F8-IL1F5-IL1F10-IL1RN, of which IL1A, IL1B and IL1F8 only are transcribed towards the centromere. The gene order relates to the evolutionary relationship between the genes. Key features of exon boundaries are conserved. There is no evidence for other IL-1 family members within the cluster.

Recently, it was shown that the most closely related receptor to IL-1R1, known as IL-1 receptor related protein 2 (IL-1Rrp2, gene IL1RL2) confers responsiveness to IL-1F9 on transfected cells, and that the response is very effectively inhibited by IL-1F5 (IL-1L1), which most closely resembles IL-1ra. The interaction with IL-1F5 seems to be of high affinity. Both IL-1F5 and IL-1F9 are relatively abundant in epithelia, and it has been suggested that they have a role in the regulation of inflammation in this specific compartment. The functions of the other genes are unknown, but low affinity interactions have been reported between IL-1F7 and IL-18R1 (Pan et al., J Immunol. 2001 Dec. 1; 167(11):6559-67), and between IL-1F10 and IL-1R1 (Lin et al., 2001). The biological role for the new IL-1 family members is under investigation, but mRNA expression appears to be far more restricted than has been seen in IL-1α, IL-1β, IL-1ra and IL-18. It is possible, therefore, that the cell types involved in the function of the new IL-1 family members are much more specialised than is the case for IL-1.

Material and Methods

Sequencing and Sequence Assembly.

BACs were identified according to partial sequence in the public domain (Lander et al., 2001) as containing IL1A, IL1B, IL1RN and IL1F5, which had previously been mapped to a gene cluster (Nicklin et al., 1994; Notwang et al., 1996; Barton et al., 2000). The nine selected BACs were RP11-1I24, RP11-477F18, RP11-554I7, RP11-368A17, RP11-434I13, RP11-67L14, RP11-725J3, RP11-339F22, RP11-97J14 and RP11-65I12. Much of the public data was unfinished and contained no order or orientation information. Aligning the public sequence of individual BACs against one another provided minimal overlap information. In order to generate a minimally tiled scaffold across the region, seven BACs were chosen (RP11-477F18, RP11-554I7, RP11-434I13, RP11-67L14, RP11-725J3, RP11-339F22, RP11-97J14) and sequenced to 3× coverage. Small insert plasmid clones (~3500 bp) were sequenced in both the forward and reverse directions, providing paired reads across clones. PHRED and PHRAP (Ewing et al., 1998; Ewing and Green, 1998) were used for the base calls and assemblies of the seven BACs. Internal contig viewing tools were used to analyze the resulting assemblies. We ordered contigs by matching sequenced contig ends whose paired reads fell on other contig ends. At this low coverage, the BACs assembled to a large number of contigs, but the order and orientation were established. Public data for the seven internally sequenced BACs as well as two externally finished BACs (RP11-1I24 and RP11-65I12) were imported from Genbank. Various software tools were used to compare and align the internal, public, and overlapping sequences, providing order and orientation information across all available data. Contigs were then chosen from these alignments to create as much contiguous sequence as possible across the region and assembled using Sequencher (version 4.0.5).

Sequence Alignment and Exon Assignment.

Primer and cDNA sequences were initially matched to genomic sequences with a 2-sequence BLAST routine (Altschul et al., 1997) running on the NCBI server. Exon alignments were made with the est2genome routine (Mott, 1997), running on the HGMP server (Cambridge, UK). The program was set to identify consensus exon boundaries. 5' exons which could not be identified because of their shortness were localised manually to the closest corresponding sequence terminating at a consensus splice donor dinucleotide (GT). No attempt was made to map the 3' ends of non-coding regions as mRNA size data are largely not available.

Results

The Sequence of the IL-1 Cluster.

A 900 kilobase region was assembled into 14 ordered contiguous sequences combining the internal and public sequences. The telomeric portion of this sequence contains the gene PAX8. Subsequently, a shorter region, composed of seven of the contigs, totalling 496 kb was extracted from the region. Recent updates of the public database have allowed us to patch five of the six gaps in the sequence, (see FIG. 17). We have submitted an annotated sequence, as described in this report, of 495475 nucleotides to the public databases (accession ***). The single remaining gap (marked "gap" on FIG. 17) is centromeric of the IL-1 cluster. The sequence is not of finished quality but provides a framework for the finished sequence and allows us to examine the structure of the genes within the IL-1 cluster. The new map is consistent with previously published maps (Nicklin et al., 1994; Nothwang et al., 1996) but differs substantially from the incomplete public genome assembly project (Lander et al., 2001).

The closest identified flanking gene towards the centromere is unrelated to IL-1. It is the plasma membrane phosphate transporter SLC20A1 (previously identified as the human homologue of the gibbon-ape leukaemia virus receptor, GLVR1, accession XM_002217), which maps between 63 kb and 45 kb to the left of the origin on FIG. 1. Towards the telomere of the cluster lies TIC (Accession NM_012455), which is most probably an ARF6-selective guanine nucleotide exchange factor (MN and Tomas Klenka, manuscript in preparation), at the telomeric flank. Its map position is shown in FIG. 17.

Gene Structures

We have mapped all of the IL-1 family cDNA sequences onto the genomic sequence (FIG. 17) where the extent of the genes is shown with black rectangles. FIG. 17 shows a map of the IL-1 gene cluster. Scale bars (in kb) are provided above and below the data to aid alignments. The sources of the data described are indicated by the top three lines. "Novel sequence" was determined entirely at Genome Therapeutics. "Public DB" indicates sequence taken from Genbank. "Combined sequence" were assembled from a combination of the two sources. Above the bar representing the contig, the positions of previously described polymorphic markers (summarised by Cox et al., 1996 and di Giovine et al., 2000) are indicated with labelled arrows. The single unfilled gap is also indicated. CpG-rich regions as defined in the text are indicated "CpGr". The probable sites of the rare cutter restriction enzyme sites clusters that were used in previous mapping are also marked as "Xrec", "Yrec?", and "Zrec". The extent of the mapping of the cDNA sequences of FIG. 18 onto the contig is indicated by the solid black rectangles below the contig line, except the non-cytokine gene TIC, which is marked grey. The positions of the coding sequences for CE1, CE2 and CE3 are indicated by vertical bars. The gene symbols are followed or preceded by a chevron to indicate the direction of transcription. FIG. 17 further shows the detailed structure of the IL-1 Cluster. Each gene is listed in order from centromere to telomere. "Gene" the conventional locus name for the gene. "Orientation" is either "forward", where the deposited sequence is the sense strand, or "reverse" where it is the anti-sense. "Position" is the nucleotide numbers on the deposited sequence corresponding to each exon.

When cDNA sequences are known to be incomplete, likely extensions of exons are marked with "<" and ">" symbols. "Exon" is the name we are assigning to each exon, based on its presence in the cDNA for one of the corresponding transcripts; thus IL1RN-a4/b5/c6 is the $4^{th}$ exon of cDNA a (X52015), the $5^{th}$ of cDNA b (M55646) and the $6^{th}$ of cDNA c. The identities of the corresponding mRNAs has been agreed (**). An asterisk (*) against adjacent entries indicates that two exons share a splice donor site as a result of the use of alternative promoters. "Exon Boundaries" are the 15 nucleotide sequences within the exon that flank the intron. An ellipsis ( . . . ) at either end indicates that the exon is likely to be incomplete because the cDNA sequence has been truncated. "Exon type" indicates the coding potential of the exon: 5'N, 5'-non-translated region; 5'SO, potentially translated 5' short open reading frame; Ps, peptide presequence (indicates that this has been proposed); cs, unconserved coding sequence; CE, conserved exons; 3'N, 3'-non translated region. An ellipsis indicates that the exon assignment is probably not complete and that some or all non-coding sequence has been omitted. "Coding" indicates the amino-acid sequence encoded by each exon. The exons are identified by the cDNA name and accession (indicated at the top of the box) that they compose. The coding capacity of each exon is indicated in lower case. Italicised residues are encoded partly on the next exon. The numeric superscript indicates the number of bases in the stated exon contained within the codon. The residue is omitted from the next exon. The nucleotides in the bridging codon are indicated by italics in the "exon boundaries" box. Where the succeeding exon is alternative, the bridging residue may change. This is indicated in parenthesis. Underscored residues are from the terminal complete codons of the exon and their codons are underscored in the "exon boundaries" box. An asterisk indicates translational termination.

ILA is the most centromeric gene and is transcribed towards the centromere, as is the adjacent gene, IL1B. The remaining genes, ending with IL1RN, the most telomeric member of the cluster, are transcribed towards the telomere, with the exception of IL1F8. The three last exons of each gene, which we have called common exons (CE)1,2 and 3, encode the IL-1-homologous domain (as shown in FIG. 18 and defined elsewhere) and fall in compact regions within the sequence. CE1, CE2 and CE3 are indicated by vertical bars in FIG. 1, but at the resolution of FIG. 17, some cannot be distinguished. Additional exons with little or no coding content extend the span of most of the genes considerably. The largest spans are IL1RN and IL1F8. In the latter case, the first non-coding exon is 20 kb telomeric of the rest of the gene. Details of the mapping of the genes are given in, along with the encoded peptide sequence from each exon. Where splice variants exist this information allows die reader to assemble the different possible protein forms. It is currently uncertain whether all of these forms are likely to be biologically relevant (see Discussion).

FIG. 18 (sheets 1-7) shows the alignment of the encoded sequence of the three common exons of the ten known members of the IL-1 family. In each case the common exons are the last three of a transcript; e.g. exons 5, 6 and 7 out of the 7 exons of IL-1α. Alignment was done by eye by seeking amino acid identities and blocks of similar residues. Gaps were then minimised. Crystallographic data for IL-1β and IL-1ra were incorporated and used further to refine the alignment Translations of the three common exon portions are shown in order. Numbers indicate the first and last codons of the mature product that are encoded by each exon. Gene products are listed in accordance with their probable phylogeny. (!) indicates that processing at a proteolytic site yields the mature protein, but that some of the presequence is also encoded within the first common exon. Blocked residues are common to at least three sequences. For simplicity, similarity is not indicated. For IL-1β and IL-1ra, on the first line below the coding sequence, (labelled "crystallography") the approximate positions of the ends of the β-sheets are indicated by vertical bars and the span of the sheet is shaded grey and labelled with the number of the sheet. In the next line (labelled "contacts"), numbers indicate the domain of the IL-1R interacting with the side chain of each residue. A numbered residue contains at least one heavy atom (C, N, O, S) that lies within 4 Å of a heavy atom of the type I IL-1 receptor (PDB data), as visualized with the program RasMol (Sayle and Milner-White). In the line below IL-1F5 (labelled NMR), a (^) indicates residues of IL-1F5 that show a strong (>0.7 ppm) upfield shift in their α-$^{13}$C NMR signal, which is taken to indicate a high probability of its residing within a β-sheet. The final line of the block (labelled "consensus") indicates, in lower case, residues that occur at least 7/10 times in that position. Where capitalized, the residue is present in all cases. An ellipsis indicates that sheet 1 of a particular sequence probably begins on a previous exon. (*) indicates translational termination.

CpG-rich Regions.

The program CpGplot (Larsen et al, 1992) was used to identify five potential CpG islands with ≧60% C+G content, ≧60% of the expected frequency of the CpG dinucieotide and of ≧300 nucleotides in length. With the exceptions of the first and the two last CpG-rich sequences, these regions are short and probably do not constitute "CpG islands". There are thus no CpG islands in the IL-1 cluster. We have attempted to locate the clusters of restriction sites that were used previously for physical mapping (Nicklin et al., 1994). CpG-rich sequences are labeled CpGr in FIG. 1. Two are further labeled Xrec and Zrec. These two regions contain the specific rare cutter restriction sites that were identified previously, and so probably correspond to the cluster's flanks, as previously assigned. The sequence data gives a length of 392 kb compared with the previous estimate of 430 kb from Southern hybridization of restriction digests of genomic DNA. A close pairing of Nae I and Eag I sites, which was previously used to map IL1B is seen around the site labelled Yrec?, but was not selected by the program CpGplot, even with less stringent parameters. Only Xrec and Zrec mark substantial CpG islands. Database searching and the public genome annotation effort has not yet revealed genes to be associated with either of these loci. One possibility is that Zrec marks an unrecognised upstream exon of TIC, a non-cytokine gene that is abundantly expressed in all tissues tested (Tomas Klenka and MN, unpublished data).

Polymorphic Markers in the IL-1 Cluster.

We have placed the polymorphisms in this region that have been described previously (indicated by arrows in FIG. 17 and listed in FIG. 19). This has allowed us to reassess disequilibrium data described previously (Cox et al., 1998). Our analysis gives a slightly better correlation coefficient between map distance and decay of disequilibrium (data not shown).

Scanning the IL-1 Cluster for Further IL-1-like Genes.

We investigated whether there are further IL-1-like sequences within the IL-1 cluster. Because of its relatively small size, the genomic sequence of the cluster was amenable to very low stringency searching with the BLAST algorithm (Altschul et al., 1997). The NCBI server for two-sequence BLAST comparisons was used with its default settings, except that the sensitivity was raised to expect 5000 hits per genome (from its default value of 10). Translations of individual exons were submitted for TBLASTN analysis of the IL-1 cluster genomic sequence. This algorithm performs a search of the coding sequence against the six possible reading frames derived from the genomic sequence fragment. We assumed that exon structure would be conserved, so matches were subsequently discounted if they were interrupted with stop codons.

Because it is one of the more distantly related sequences, we searched first with the CE3 of IL1A. This matched only itself. CE3 of IL1B returned CE3 of all known family members on the IL-1 cluster except IL1A. One uninterrupted hit was found, but it shared only 6 identical putative residues, was longer than typical for a CE3 and actually lay in reverse orientation within IL1B. The sequence was discounted as there was no evidence for a corresponding potential upstream CE2. We next searched with CE3 of IL1F5, which also returned all of the CE3s except IL1A. One long, potential CpG-rich exon lacked the conserved core residues of CE3. As another outlier, we used CE3 of IL18 (accession XM_041373). This returned IL1F5 from the IL-1 cluster and no novel sequences. We next tested CE2 (exons 6) from IL1A and IL1B. The former returned only itself, the latter returned IL1F6, IL1F8, IL1F9 and IL1F10 and no other sequence. CE2 of IL1F5 returned IL1RN, IL1F6, IL1F9 and IL1F10, but no novel uninterrupted exons. CE2 of IL18 returned none. Finally CE2 of IL1F9 was tested. It returned CE2 of IL1F6, IL1F8, IL1RN, ILF10 and no other sequence. We conclude that there are no further IL-1 family genes within the IL-1 cluster unless they have either a highly divergent sequence or differ from all of the other family members in having a more fragmented exon structure.

Evolutionary Considerations

To investigate the phylogeny of the IL-1 family, We ran the program Tree-Puzzle (Strimmer and von Haesler, 1996) on the alignment of CE3 shown in FIG. 2a. IL-18 was set as the outgroup member of the family. The result was visualised in a radial dendrogram (Page, 1996) shown in FIG. 3.

Example 2

Case—Cohort Study of Inflammatory Genes and Coronary Heart Disease (a Sub-study of the Atherosclerosis Risk in Communities (ARIC) Project)

ARIC is a prospective cohort study designed to investigate the etiology and natural history of atherosclerosis, the etiology of clinical atherosclerotic diseases, and variation in cardiovascular risk factors, medical care, and disease by race, gender, place and time.

The ARIC cohort consists of a probability sample of 15,792 individuals, age 45-64 years at baseline, from four U.S. communities. ILGN has approval to genotype all participants in the ARIC program as appropriate to meet the objectives of the two collaborative sub-studies. In our ongoing study of incident cardiovascular events we now have DNA samples from 955 ARIC participants who have experienced acute clinical events along with a randomly sampled cohort control group. These samples represent all incident cardiovascular cases during the first 11 years of longitudinal monitoring. The genotyping of all samples was recently completed and partial results are available. These results demonstrate significant associations between risk of clinical events and IL-1(+4845) allele 2 for subjects with total cholesterol (TC) <200 mg/dl. Key aspects of these findings include:

+4845 genotype significantly associated with clinical events (*Survival Analysis Relative Risk*~4.0, p<0.01)

Analysis included all ages

In a multivariate model, the IL-1 genotype findings were independent of age, gender, smoking, race, diabetes, hypertension, BMI, LDL, HDL Number of subjects included with TC<200 was 955

Locus: IL1A (+4845), Total Cholesterol<200 mg/dl Stratum Time to First Acute Coronary Artery Disease Event Within each table there are three models. The first is the crude model which has just the genotype variables. This is identified by "Crude" in the Adjustment column. The models with "Group 1" in the Adjustment column adjust for age, sex and race/center. Those with "Group 2" in the Adjustment column adjust for age, sex, race/center, current smoker (yes/no), diabetic (yes/no), hypertensive (yes/no), LDL cholesterol, and HDL cholesterol.

TABLE 1

Comparing '1.2' and '2.2' against the baseline of '1.1'

| Adjustment | Genotype | BETA | SE | T | P | RR | LOWER_95 | UPPER_95 |
|---|---|---|---|---|---|---|---|---|
| Crude | 1.2 | −0.27372 | 0.21851 | −1.25269 | 0.21032 | 0.76054 | 0.49559 | 1.16714 |
|  | 2.2 | 0.34378 | 0.40769 | 0.84324 | 0.39909 | 1.41027 | 0.63426 | 3.13573 |
| Group 1 | 1.2 | −0.05382 | 0.24299 | −0.22151 | 0.82469 | 0.94760 | 0.58856 | 1.52566 |
|  | 2.2 | 0.72707 | 0.47274 | 1.53798 | 0.12405 | 2.06901 | 0.81913 | 5.22602 |
| Group 2 | 1.2 | −0.02903 | 0.28294 | −0.10261 | 0.91827 | 0.97139 | 0.55789 | 1.6913 |
|  | 2.2 | 1.38022 | 0.49320 | 2.79850 | 0.00513 | 3.97577 | 1.51217 | 10.4530 |

TABLE 2

Comparing '2.2' against the baseline of '1.1' and '1.2' together

| Adjustment | Genotype | BETA | SE | T | P | RR | LOWER_95 | UPPER_95 |
|---|---|---|---|---|---|---|---|---|
| Crude | 2.2 | 0.46712 | 0.39696 | 1.17673 | 0.23930 | 1.59539 | 0.73277 | 3.47352 |
| Group 1 | 2.2 | 0.75024 | 0.45891 | 1.63485 | 0.10208 | 2.11752 | 0.86139 | 5.20541 |
| Group 2 | 2.2 | 1.39344 | 0.47638 | 2.92505 | 0.00344 | 4.02869 | 1.58365 | 10.2487 |

TABLE 3

| | Comparing '2.2' against the baseline of '1.1' with subjects having '1.2' excluded | | | | | | | |
|---|---|---|---|---|---|---|---|---|
| Adjustment | Genotype | BETA | SE | T | P | RR | LOWER_95 | UPPER_95 |
| Crude | 2.2 | 0.34181 | 0.40774 | 0.83831 | 0.40186 | 1.40750 | 0.63295 | 3.12987 |
| Group 1 | 2.2 | 0.75725 | 0.48656 | 1.55634 | 0.11963 | 2.13241 | 0.82168 | 5.53400 |
| Group 2 | 2.2 | 1.60027 | 0.57185 | 2.79840 | 0.00514 | 4.95436 | 1.61517 | 15.1970 |

Example 3

The San Francisco Study of Osteoporotic Fractures (SOF)

The Multi-center Study of Osteoporotic Fractures under the direction of Dr. Steven Cummings at the University of California in San Francisco, consists of a large cohort of women of European/Caucasian origin from 4 different clinical centers. These women have been examined since 1986 for various medical and lifestyle findings, including hip, wrist and spine fractures and changes in bone mineral density in lumbar spine and femoral neck. At baseline visit (1986/1987) all participants (n=9,704) were 65 year or older, ambulatory and not institutionalized. Blood samples were collected from approximately 4,000 subjects and stored at −70° C. for DNA analysis.

A recent analysis of cause of death in the SOF cohort determined that IL-1A(4845) allele 2 was significantly associated with early death from cardiovascular disease.

TABLE 4

| CVD death | N = 452; | Relative Risk | LOWER CI | UPPER CI | UNIT | PVALUE |
|---|---|---|---|---|---|---|
| IL1A_1 | IL-1A 1.2 VS 1.1 | 1.03 | 0.49 | 2.167 | 1 | 0.937 |
| IL1A_2 | IL-1A 2.2 VS 1.1 | 3.138 | 1.203 | 8.184 | 1 | 0.0194 |
| RAGE2 | ADJUSTED CURRENT AGE | 2.431 | 1.842 | 3.209 | 5 | 0 |

Example 4

Functional Analysis of the +4845 IL-1 SNPs

+4845 SNP is a non-synonymous SNP (i.e. a naturally-occurring polymorphism which alters the amino acid of and leads to an amino acid change in the IL-1a cytokine). The variant proteins are expressed in insect cells using bacculoviral vectors and analyzed for structural and functional differences. The variant cDNAs used for the expression of the protein in insect cells and in mammalian cells are confirmed by sequence analysis to only contain one SNP leading to an amino acid change. Here are 2 pieces of data related to this SNP.

Figure 12:
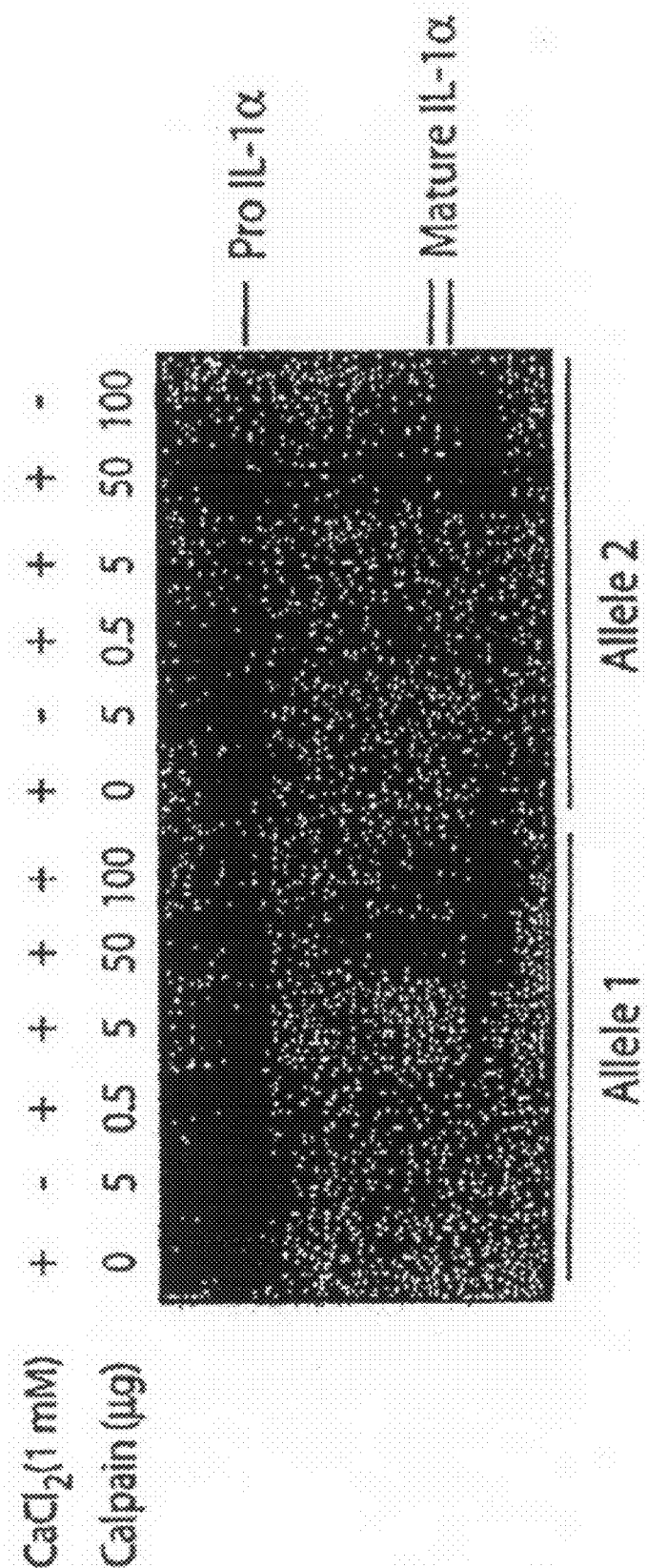
FIG. 12 shows that the difference in cleavage by calpain protease of IL-1α variant corresponding to alleles 1 and 2 of IL-1A +4845.

In the Western Blot analysis (see FIG. 12), we provide data to show that the 2 variants of the IL-1a cytokine are processed differently with calpain digestion. Calpain is an enzyme known to cleave the full length IL-1a cytokine (31 kDa) to form the mature protein (17 kDa). The allele-1 (Ala) IL-1a cytokine gives rise to a single 17 kDa molecule, whereas, the allele-2 (Ser) IL-1a cytokine yields 2 bands, one which is identical in size to the band found with the allele-1 but additionally, it also gives rise to another band which is slightly larger in molecular weight. This result indicates that there is a structural difference in the 2 variants. We also postulate that the Ala to Ser mutation leads to differential post-translational modification of the proteins, for example, differences in phosphorylation or myristolation. This amino acid change could lead to an alteration (addition or removal) of the recognition signal for the post-translation modification.

Figure 13:
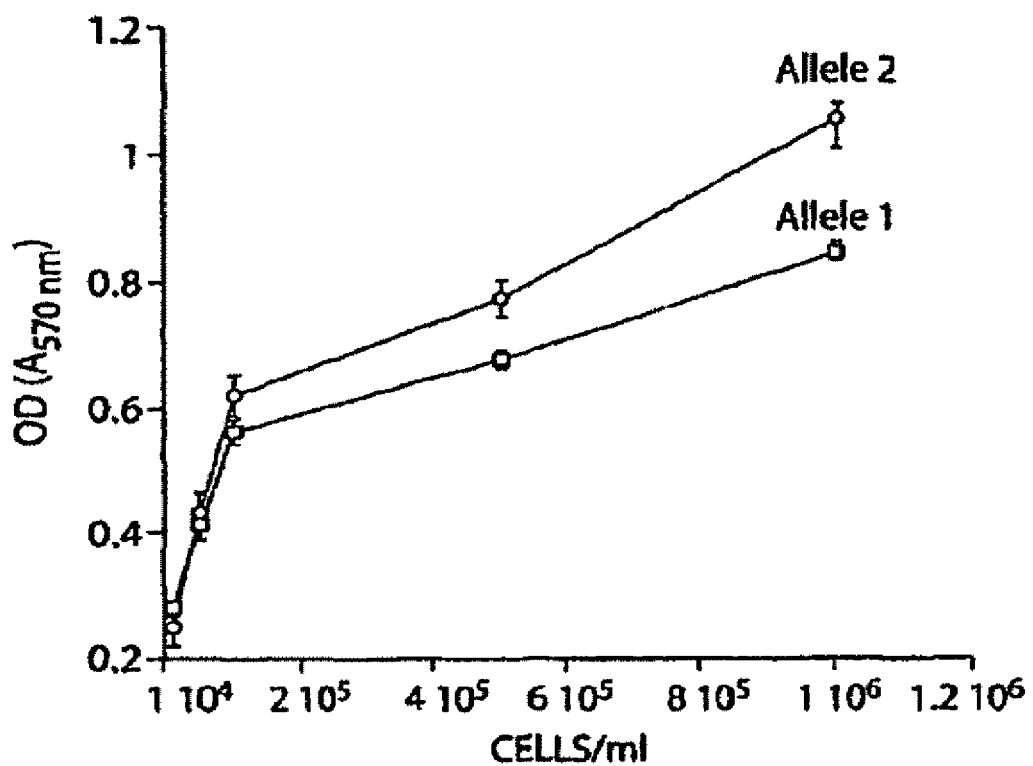
FIG. 13 shows the rate of proliferation of fibroblast cells stably transfected with vectors expressing the allele 1 and allele 2 variants of IL-1+4845.

Fibroblast cells stably transfected with the ala and ser variant cDNAs in expression vectors were found to have a different rate of proliferation. The allele-2 variant has a faster growth rate than the allele-1 variant that supports our claim that allele-2 is predictive of a proinflammatory profile, (see FIG. 13). Accordingly, the altered amino acid in the allele-2 variant shows evidence of a more potent proinflammatory cytokine than the allele-1 variant.

Example 5

Systematic Functional Analysis of the IL-1A, IL-1B and IL-1RN SNPs

In this example, selected IL-1A, IL-1B, and IL-1RN polymorphisms are constructed in a background of otherwise "wild type" IL-1 sequence and the effects are measured in a fibroblast cell line.

Figure 14B:
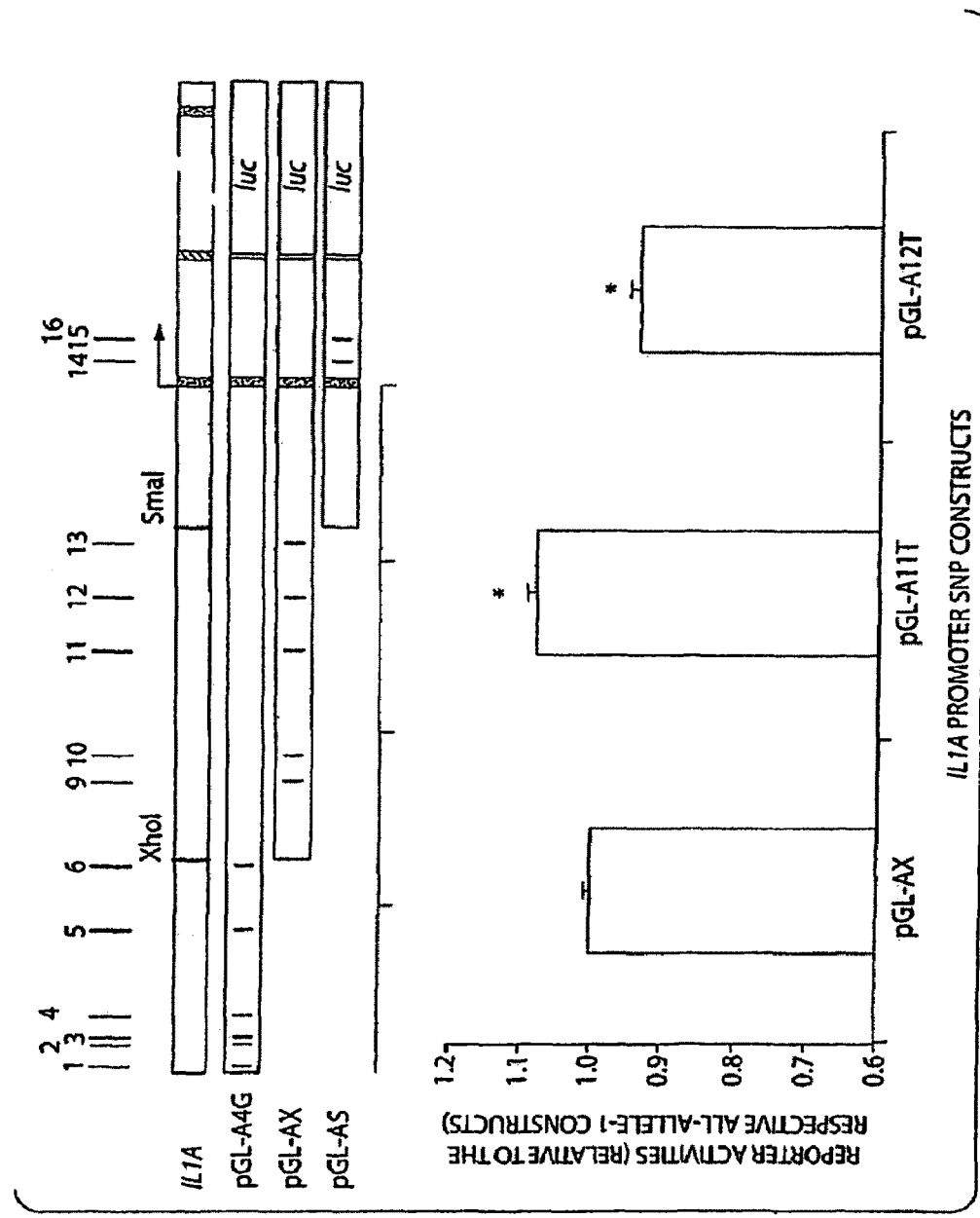
FIGS. 14 (A and B) shows the genotypes of IL-1A SNP constructs (A) and selected reporter activities in a fibroblast cell line (B).

Transcriptional analysis of IL-1A, IL-1B, IL-1RN gene promoter SNPs by reporter-promoter constructs. Each gene's data is in separate figure (i.e. FIGS. 14, 15 and 16 respectively). The FIGS. 14, 15, and 16 panel A (and FIG. 15 D) shows the SNPs and the various allele-2 mutations that were created in separate luciferase constructs and also the different lengths of promoter-luciferase constructs annotated with the SNPs investigated in the transfection analysis. In addition, we also provide luciferase assay results for only the functional SNPs that show an altered activity of the gene transcription with respect to the wild type (allele-1 at all loci). For the B gene, we also provide data for the functional SNPs in a backbone where SNP#14 (−511) and SNP#2 (−31) are also allele-2.

Note that these constructs were tested in a fibroblast cell line (i.e. WI38—which models a specific role of IL-1 in the inflammatory response. Accordingly, other cell lines which model other mechanistic aspects of IL-1-mediated inflammatory diseases and disorders will be specifically tested. For example, human cell monocyte cell lines (e.g. U937) and human karatinocyte cell line (e.g. A143) and in a human osteoblast cell line (e.g. to investigate affects upon osteoporosis IL-1 inflammatory processes.

Example 6

Annotation of the IL-1 Gene Cluster SNPs

We have further annotated polymorphisms throughout the IL-1 gene cluster (see FIGS. 8-11). As these polymorphisms occur within established IL-1 haplotypes as herein supported (see FIGS. 1-7), they provide compositions and methods which are supported in the instant application.

Example 7

Use of Composite Genotypes of the IL-1 Gene Cluster to Predict IL-1β and C-Reactive Protein Levels Interleukin-1β (IL-1β) is a potent cytokine involved in critical pathobiological processes of cardiovascular disease including recruitment of blood leukocytes, activation of downstream mediators such as IL-6 and CRP, and modulation of clot formation/dissolution. Extracellular release of IL-1β is regulated by complex feedback loops involving both the IL-1B gene, encoding the pro-inflammatory cytokine, as well as the IL-1RN gene encoding its natural antagonist.

In this study IL-1 SNPs shown in Table 5 were evaluated for genetic association with IL-1β levels from gingival crevicular fluid and levels of serum CRP. A schematic illustration of the IL-1 gene cluster showing these SNPs is provided in FIG. 20.

TABLE 5

| Gene | Position | Nucleotide |
|---|---|---|
| IL-1B | −511 | 1 = C, 2 = T |
| IL-1RN | +2018 | 1 = T, 2 = C |
| IL-1B | +3954 | 1 = C, 2 = T |
| IL-1B | +3877 | 1 = G, 2 = A |
| IL-1A | +4845 | 1 = G, 2 = T |

Study participants were obtained from the Atherosclerosis Risk in Communities (ARIC) Study, a prospective study of etiology and natural history of atherosclerosis having 15,972 subjects (age 45-65 at baseline) in each of four communities (Forsyth County, North Carolina, Jackson, Miss., the suburbs of Minneapolis, Minn., and Washington County, Maryland). The subjects' age range was 45-65 at baseline examinations done 1987-1989. Dental exams were performed on a subset of ARIC participants. Study participant characteristics are provided in Table 6.

TABLE 6

|  | Caucasians (n = 900) | African Americans (n = 227) |
|---|---|---|
| Age, mean (sd) | 61.7 (5.3) | 59.8 (4.6) |
| Male gender | 45% | 37% |
| Current smoking | 22% | 14% |
| Diabetes | 15% | 32% |
| BMI, mean (sd) | 27.9 (5.0) | 31.0 (6.8) |
| IL-1B (−511) allele 2 | 34% | 57% |
| IL-1RN (+2018) allele 2 | 27% | 8% |
| IL-1B (+3954) allele 2 | 22% | 13% |
| IL-1B (+3877) allele 2 | 36% | 18% |
| IL-1A (+4845) allele 2 | 28% | 20% |

Generally, prior studies have examined the IL-1 cluster 1 SNP at a time, but SNPs in IL-1 cluster exhibit strong linkage disequilibrium (LD). Table 7 shows two blocks of SNPs in LD.

TABLE 7

| IL-1A | IL-1B |  | IL-1 RN |  |
|---|---|---|---|---|
| +4845 | +3954 | +3877 | −511 | +2018 |
| LD Block 2 |  |  | LD Block 1 |  |

LD Block 1 contains IL-1B (−511), which is associated with risk of myocardial infarction and IL-1β release from PBMC (Iacoviello, 2005). LD Block 2 contains SNPs associated with elevated CRP and/or fibrinogen (Berger, 2002; Latkovskis, 2004). The present study identified composite genotypes encompassing markers from these two LD blocks and the association with inflammatory biomarkers and the risk for inflammatory-associated disease outcomes. FIG. 21 shows the composite genotype frequencies of study participants. LD Block 1 genotype is 1/1, 1/2, or 2/2 as determined by IL-1B (−511). LD Block 2 is carriers of allele 2 at both IL-1A(+4845) and IL-1B(+3954) who are also 1/1 at IL-1B (+3877) are considered as "+". All others are "−".

Statistical analysis of the data was performed as follows. Ordinary linear regression is performed after log transforming IL-1β and CRP values. Results are adjusted for age, BMI, sex, and diabetes. Results are presented as percentage increase compared to reference group of 2/2−. The data excluded current smokers and focused on a subset of Caucasians.

FIG. 22 shows IL-1β levels in the composite genotypes. Subjects having an LD Block 1 genotype 1/1 have increased IL-1β levels.

FIG. 23 shows C-reactive protein levels in the composite genotypes. Subjects having an LD Block 2+/+ genotype have increased C-reactive protein levels. Subjects having an LD Block 2−/− genotype and an LD Block 1½ genotype also have increased C-reactive protein levels.

Table 8 Summarizes the Results of the Studies of and C-reactive Protein

TABLE 8

| LD block 1 | LD block 2 | IL-1β | CRP |
|---|---|---|---|
| 1/1 | + | ↑ | ↑ |
| 1/1 | − | ↑ |  |
| 1/2 | + |  | ↑ |
| 1/2 | − |  |  |
| 2/2 | + |  |  |
| 2/2 | − |  |  |

These studies demonstrate that composite genotypes of the IL-1 gene cluster are useful for segmenting this population of Caucasians according to levels of inflammatory biomarkers. Specifically, two composite genotypes, both with 1/1 at LD Block 1, are associated with high levels of IL-1β. Also, two composite genotypes, both with "+" at LD Block 2, are associated with high levels of CRP. In certain embodiments, these genotypes also include the IL-RN (+2018) allele. The composite genotypes used in this study vary in frequency between Caucasians and African Americans. These results are useful in diverse ethnic/racial groups. Also, the composite genotypes are useful to predict clinical events, including myocardial infarctions.

Example 8

The Use of IL-1B Genotypes to Predict IL-1β and C-Reactive Protein Levels

Inflammation appears to be a central mechanism in the initiation and progression of multiple chronic diseases of aging. Among overtly healthy persons, some individuals are consistently in the upper range for certain inflammatory mediators, such as IL-1β and C-reactive protein (CRP). Moreover, compared to those in the lower end of the spectrum, these individuals are at increased risk for many diseases. Factors such as smoking, body mass index, and hormone replacement therapy explain a portion of the variance of inflammatory mediators in overtly healthy individuals, but genetic differences also appear to be an important determinant of inter-individual variance in inflammatory mediator levels. Here we show haplotypes that are correlated with increased IL-1β expression and increased CRP expression, leading to the correlation of these haplotypes, and the alleles contained within these haplotypes with inflammation and the initiation and progression of many chronic diseases associated with aging.

Inflammation is a major component of multiple diseases, and interleukin-1, which is regulated by the IL-1 gene cluster, is a primary initiator of the inflammatory process. Below we show that certain haplotype pairs of IL1B are predictive of a higher expression of IL-1β in gingival crevicular fluid as well as higher levels of CRP in serum.

The study sample was selected from the Atherosclerosis Risk in Communities study (ARIC), as described in Example 7, above. The study sample, used below, comprises the 900 Caucasians from ARIC with both dental examinations and IL1 genotypes. IL-1β levels from these subjects were assessed from samples of gingival crevicular fluid (GCF). Since the gingival crevice epithelium is in constant contact with a microbial biofilm, the level of IL-1β within the gingival crevicular fluid represents a serum transudate that is enriched by the local evoked gingival tissue response that has reached a steady state. Gingival crevicular fluid was collected as described in detail previously (Champagne et al., Periodontology 2000, 2003; 31: 167-180). Briefly, four GCF strips were eluted and analyzed separately (from the mesio-lingual of each first molar) from each subject and pooled to provide a patient mean value in pg/mL. IL-1β concentrations were measured on the GCF strip, using Enzyme-Linked Immunoadsorbent Assays (ELISA, Caymen Chemical Ann Arbor, Mich.).

C-reactive protein (CRP) in serum was measured, in these subjects, with a high sensitivity assay. Fasting blood samples were taken from all subjects and serum was frozen for subsequent analysis as previously described (Papp et al. Thrombosis & Haemostasis 1989 61(1): 15-19). Serum C-reactive protein (CRP) concentrations were measured by latex-enhanced nephelometry (High Sensitivity CRP assay) on a BNII nephelometer (Dade Behring, Deerfield, Ill.). The BN II high sensitivity CRP assay utilizes a monoclonal antibody attached to polystyrene particles and fixed-time kinetic nephelometric measurements. This fully automated system creates a seven point standard curve from 0.4975 µg/ml (1:40 dilution of Rh Standard SL) to 0.0078 µg/ml (1:2560 dilution). The BN II makes a 1:400 dilution to measure sample CRP concentrations between 3.5 and 210 mg/L and a 1:20 dilution below 3.5 mg/L. This is an FDA, CLIA-complaint assay. Individuals with values above or below the limits of detection were excluded from analysis.

Since the GCF volume and protein composition is influenced by the local tissue inflammation, two periodontal endpoints were included in the study as covariates. One endpoint was the assessment of the percent of pocket depths of 4 or more millimeters. The second variable is composite measure of periodontal disease composed of pocket depth, bleeding on probing and interproximal attachment level of 3 millimeters or more measured on a 6-point ordinal scale. This composite measure is a more detailed version of an index developed to assess the inflammatory status of the periodontal tissue-biofilm interface (Offenbacher et al., Oral Biosci Med. 2005; 213:215-220).

Blood samples were collected in ethylenediaminetetraacetic acid (EDTA)-containing tubes and DNA was extracted for genotyping in the Division of Genomic Medicine, University of Sheffield, Sheffield UK Blood used for plasma factors was centrifuged and frozen at $-70°$ until analyzed. All genetic and blood analyses were performed by individuals unaware of other data.

Single nucleotide polymorphisms (SNPs) were tested at three locations within the IL1B promoter, IL1B(−511) (C→T transition), IL1B(−1464) (G→C transition), and IL1B(−3737) (C→T transition). Two additional SNPs, IL1A(+4845) (G→T transition) and IL1B(+3954) (C→T transition), were also genotyped to facilitate comparisons with other studies. The first nucleotide designated for each polymorphism is the common allele in Caucasians (e.g. −511C) and is referred to as "1", while the second nucleotide (e.g. −511T) is the less common allele and is termed "2". Genotyping was performed by Taqman™ 5' nuclease assay, as previously described (di-Giovine et al., 2000 Detection and population analysis of IL-1 and TNF gene polymorphisms. In: Cytokine Molecular Biology. Oxford University Press, Oxford, UK Practical Approach Series, Chapter 2, pp. 21-46).

HAPLO.SCORE (Schaid, Am J Hum Genet, 2002; 70:425-434) was used to identify haplotype frequencies with non-negligible frequencies (>0.5%). Next, each possible pair of haplotypes drawn from this set were formed and determined whether the resulting haplotype-pair groups could be recreated unambiguously from phase unknown genotypes of the individual SNPs.

The overall null hypothesis of equal mean IL-1β levels across all haplotype pair groups was tested using analysis of variance (ANOVA) with degrees of freedom equal to the total number of groups minus one. The log-transformed values were used because of skewness in the distribution of IL-1β.

To identify specific haplotype groups associated with high IL-1β levels, mean levels of IL-1β were compared between each pair of haplotype groups. Next, the nominal p-values were calculated for each comparison the pairs were ranked from most to least significant. Finally, patterns of haplotypes clustering among the most significant pairs were sought.

Linear regression was used to estimate the magnitude of difference in IL-1β for different haplotype-pair groups. To do so, the set of non-genetic covariates was identified that associate with IL-1β. Then, with these covariates in the model, indicator variables for the haplotype pair groups were added. A similar approach was taken for CRP analysis except 1-sided p-values were calculated to reflect an a priori expectation of die direction of the effect based on the IL-1β results.

Demographic characteristics of the 900 Caucasian study participants are presented in Table 9. The study group was made up of 900 Caucasian subjects. Plus-minus values are ±SD.

TABLE 9

Subject characteristics.

| Variable | |
|---|---|
| Age - yr | 61.7 ± 5.3 |
| Female sex - no. (%) | 498 (55) |
| Current smoker - no. (%) | 199 (22) |
| Diabetes - no. (%) | 133 (15) |
| Body mass index - kg/m$^2$ | 27.9 ± 5.0 |
| IL-1β - pg/mL | |
| Median | 155 |
| Interquartile range | 95-235 |
| C-reactive protein - mg/L | |
| Median | 4.2 |
| Interquartile range | 1.9-8.9 |

It has previously been reported that the gene for IL-1β had no detectable non-synonymous exonic SNPs and had four SNPs in the promoter-enhancer region that showed functional activity that was dependent on haplotype context, in multiple ethnic groups studied, two of the functional SNPs, IL-1B(−31) and IL-1B(−511) were perfectly concordant; therefore we used the three SNPs shown in Table 10 to characterize the functionally important IL-1B genetic variation. The nucleotide transition at the indicated locus shown has the first nucleotide as the most common allele, i.e. allele 1, in Caucasian populations. "ND" means that the allele was not detected in the study population.

TABLE 10

Promoter haplotype frequencies

| Haplotype | IL1B(−511) (C to T) | IL1B(−1464) (G to C) | IL1B(−3737) (C to T) | Frequency |
|---|---|---|---|---|
| B1 | 1 | 1 | 2 | 46% |
| B2 | 2 | 2 | 1 | 28% |
| B3 | 1 | 1 | 1 | 20% |
| B4 | 2 | 1 | 1 | 6% |
| B5 | 1 | 2 | 1 | ND |
| B6 | 1 | 2 | 2 | ND |
| B7 | 2 | 1 | 2 | ND |
| B8 | 2 | 2 | 2 | ND |

Analysis of the 900 subject Caucasian population using HAPLO.SCORE (Schaid 2002) indicated that of the eight potential three-SNP haplotypes only four haplotypes were detected, which we have denoted B1, B2, B3, and B4 (Table 10).

Given the four observed haplotypes, there are ten possible three-SNP genotype patterns (ignoring phase) arising from these haplotypes (Table 11).

TABLE 11

Possible composite genotypes from 4 observed haplotypes

| Haplotype pairs | IL-1B(−511) | IL-1B(−1464) | IL-1B(−3737) | Frequency |
|---|---|---|---|---|
| B1/B1 | 1.1 | 1.1 | 2.2 | 22% |
| B1/B2 | 1.2 | 1.2 | 1.2 | 25% |
| B1/B3 | 1.1 | 1.1 | 1.2 | 17% |
| B1/B4 | 1.2 | 1.1 | 1.2 | 8% |
| B2/B2 | 2.2 | 2.2 | 1.1 | 7% |
| B2/B3 | 1.2 | 1.2 | 1.1 | 12% |
| B2/B4 | 2.2 | 1.2 | 1.1 | 3% |
| B3/B3 | 1.1 | 1.1 | 1.1 | 4% |
| B3/B4 | 1.2 | 1.1 | 1.1 | 2% |
| B4/B4 | 2.2 | 1.1 | 1.1 | <1% |

Because each of the ten haplotype pairs is unique, haplotypes can be assigned unambiguously for any individual. All of the ten possible composite genotype patterns were observed in the study population, but less than 1% of individuals (n=3) were homozygous for the B4 haplotype (Table 11). In addition, we point out that IL1B(−511) and IL1B(−1464) largely convey the same information in this population of Caucasians, as they are concordant in all haplotypes except for the least common, B4.

Correlating genotypes with IL-1β expression levels, the null hypothesis that the mean IL-1β protein levels (logIL-1β) were equal across the ten haplotype pairs shown in Table 11 was first tested. The null hypothesis was rejected (ANOVA; 9 degrees of freedom; p=0.005), indicating that there were significantly different IL-1β levels based on haplotype pairs. Exclusion of the small B4/B4 group did not impact this conclusion (p=0.003).

Having established an overall difference in the mean log of IL-1β across haplotype pair groups, we turned our attention to the identification of a specific set of haplotype pairs associated with high levels of this cytokine. To do this, we compared each haplotype pair against every other pair, producing comparisons and characterized the two tertiles of comparisons with the most significant p-values (Table 12). The gingival fluid log IL-1β protein concentration for individuals with each of the 10 possible IL1 haplotype-pairs was compared to every other haplotype-pair, and the most significant comparisons are listed in order of nominal p-values. The first column from the left shows the haplotype-pair with the higher IL-1β protein in this specific comparison. The second column from the left shows the haplotype-pair with the lower IL-1β protein in this specific comparison. The column marked "Percent Higher" shows the mean percent increase in IL-1β protein level in individuals with the higher IL1 haplotype-pair compared to individuals with the lower IL1 haplotype-pair. The column marked "Rank" shows the relative rank of the 30 most significant haplotype-pair comparisons. The pairs marked with an asterisk (*) are the haplotype-pairs in the most significant comparisons that are comprised of genotype 1/1 at IL1B(−511). The pairs marked with a dagger (†) are the haplotype-pairs in the most significant comparisons that are comprised of genotype 1/2 at IL1B(−511) and 1/1 at IL1B(−3737).

TABLE 12

| Higher Haplotype Pair | Lower Haplotype Pair | Percent Higher | Nominal p-value | Rank |
|---|---|---|---|---|
| B1/B1* | B1/B2 | 39% | 0 | 1 |
| B1/B3* | B1/B2 | 32% | 0.002 | 2 |
| B3/B3* | B1/B2 | 53% | 0.006 | 3.5 |
| B1/B1* | B1/B4 | 37% | 0.006 | 3.5 |
| B1/B1* | B2/B2 | 34% | 0.008 | 5 |
| B1/B3* | B1/B4 | 30% | 0.025 | 6 |
| B3/B3* | B1/B4 | 51% | 0.027 | 7 |
| B3/B3* | B2/B2 | 48% | 0.032 | 8.5 |
| B1/B3* | B2/B2 | 27% | 0.032 | 8.5 |
| B1/B1* | B2/B3† | 19% | 0.042 | 10 |
| B3/B4† | B1/B2 | 47% | 0.066 | 11 |
| B3/B3* | B2/B3 | 32% | 0.072 | 12 |
| B3/B4† | B1/B4 | 46% | 0.081 | 13.5 |
| B2/B3† | B1/B2 | 17% | 0.081 | 13.5 |
| B3/B4† | B2/B2 | 42% | 0.099 | 15 |
| B1/B1* | B2/B4 | 24% | 0.113 | 16 |
| B3/B3* | B2/B4 | 37% | 0.129 | 17 |
| B1/B3* | B2/B3† | 13% | 0.132 | 18 |
| B3/B4† | B2/B4 | 32% | 0.151 | 19 |
| B1/B1* | B4/B4 | 48% | 0.169 | 20 |
| B3/B3* | B1/B3* | 16% | 0.173 | 21 |
| B2/B3† | B1/B4 | 15% | 0.182 | 22 |

TABLE 12-continued

| Higher Haplotype Pair | Lower Haplotype Pair | Percent Higher | Nominal p-value | Rank |
|---|---|---|---|---|
| B3/B4† | B2/B3† | 26% | 0.19 | 23 |
| B1/B3* | B2/B4 | 18% | 0.191 | 24 |
| B3/B4† | B4/B4 | 57% | 0.196 | 25 |
| B1/B3* | B4/B4 | 40% | 0.214 | 26 |
| B2/B3† | B2/B2 | 12% | 0.217 | 27.5 |
| B3/B3* | B4/B4 | 63% | 0.217 | 27.5 |

From this evaluation, we found haplotype pairs to partition very nicely into three groups. The first group comprises any combination of B1 and B3 haplotypes (marked with asterisks (*) in Table 12). The second group includes individuals with one copy of B3 and one copy of either B2 or B4 (marked with daggers (†) in Table 12). The third group includes all other combinations.

Of the 28 most significant haplotype-pair comparisons, the first group i.e. individuals with any combination of B1 and B3, occurs as the "high IL-1β" haplotype-pair 21 of 28 times and is never the "low IL-1β" haplotype-pair relative to any other haplotype pair. The second group i.e. individuals with one copy of B3 and one copy of either B2 or B4, occurs the remaining 9 of 28 times as the "high IL-1β" haplotype-pair and is the "low IL-1β" haplotype-pair in the most significant comparisons only when compared to the haplotype pairs in the first group. Linear regression revealed that, relative to the third group (42.6% frequency), the first group (42.7% frequency) has a 33% increased IL-1β ($p<0.0001$) and the second group (14.8% frequency) has a 28% increased IL-1β ($p<0.01$).

Gingival fluid is a serum transudate that also reflects the local periodontal tissue inflammation. Since levels of gingival fluid IL-1β are strongly associated with the severity of local periodontal disease, the analysis included adjustment for two periodontal disease severity endpoints available in this database: 1) percentage of periodontal pocket depths exceeding 4 mm, and 2) a composite measure of periodontal disease. With the two periodontal endpoints included in the model, no other covariates except for IL-1 genotypes were significant predictors of IL-1β levels in GCF.

The first group of IL-1β over-expressing haplotype-pairs translates more simply into carriage of 1/1 at IL1B(−511). Equivalently, the second group includes those who are both 1/2 at IL1B(−511) and 1/1 at IL1B(−3737). Because the group comprising individuals with 1/1 at IL1B(−511) is relatively large (>40% of this study population), we repeated our analysis splitting the group into its three haplotype pair groups: B3/B3, B1/B3, and B1/B1. Each of these components, as well as the B2/B3+B4/B3 group was significantly higher in IL-1β levels than the remaining individuals (FIG. 24). Interestingly, only two of these four groups were associated with increased serum CRP, namely B3/B3 and B2/B3+B4/B3 (FIG. 24).

The two groups associated with higher CRP levels are distinguished from the other pro-inflammatory patterns by homozygosity for the common allele (1/1) at IL1B(−3737). The combined B3/B3 and B2/B3+B4/B3 group had 33% higher CRP values versus all others ($p=0.007$) after adjustment for BMI, smoking, and gender.

Two additional SNPs in the IL-1 gene cluster, IL1A(+4845) and IL1B(−3954), have been associated with differential expression of inflammatory mediators (Berger 2002) and clinical phenotypes, and typically carriage of the minor alleles has been reported to be pro-inflammatory. The frequency of carrying a minor allele at both IL1A(+4845) and IL1B(−3954) is 35% in our study population, but this frequency increases to 84% in the B3/B3 and B2/B3+B4/B3 group compared to 23% in others. In this data set CRP was less strongly associated with IL1A(+4845), IL1B(+3954), or composites of these two SNPs than the combined B3/B3 and B2/B3+B4/B3 group.

Another pro-inflammatory haplotype pair is characterized by a 1/2 genotype at IL1B(−511) together with a 1/1 genotype at IL1B(−3737). It has been reported that individuals with 1/2 at IL1B(−511) are also at increased risk of both clinical and biochemical endpoints, but less significantly than those carrying 1/1 at IL1B(−511). As shown herein, this intermediate risk group of heterozygotes is actually comprised of two distinct groups, one with 1/1 at IL1B(−3737) and the other with 1/2 at IL1B(−3737). The former, we speculate, would be associated with clinical endpoints and biochemical measurements, perhaps as significantly as those carrying 1/1 at IL1B(−511), and the latter would be more similar to those with 2/2 at IL1B(−511). In this Caucasian population approximately 47% of the individuals carried IL1B(−511) genotype 1/2, which was divided between 14% of the population which also carried IL1B(−3737) genotype 1/1 and 33% which also carried IL1B(−3737) genotype 1/2. In this population, no individuals carried IL1B(−511) genotype 1/2 and IL1B(−3737) genotype 2/2.

Previous work has found that haplotypes with allele 2 (C nucleotide) at IL1B(−1464) consistently showed decreased promoter activity in both single SNP and haplotype constructs. In Caucasians, most haplotypes with IL1B(−511) allele 2 also included IL1B(−1464) allele 2 (haplotype B2=28% vs. B4=6%; Table 2). This is consistent with the observation in this study that genotypes composed of two copies of haplotype B2 had the lowest IL-1β levels. In addition, genotypes that included one copy of B2 showed higher levels of IL-1β only if they were also genotype 1/1 (C/C) at IL1B(−3737). NF-κB components show increased binding to IL1B (−3737) allele 1 compared to allele 2, and allele 1 at this locus increased activity of promoter constructs in certain haplotypes.

IL1B(−3737) also appears to be a key determinant of whether or not an IL1B promoter pattern associated with high IL1β is also associated with increased serum CRP levels. Specifically, individuals who carry at least one 2 allele at IL1B(−3737) do not seem to manifest high CRP values, even if they have high IL1β values. This may be due to potential temporal differences in IL-1β expression, and subsequent differential downstream effects, with haplotypes that include different IL1B(−3737) alleles.

Multiple studies have reported association of other IL1 SNPs with clinical outcomes and biochemical measurements. Frequently, authors have concluded that carriage of minor alleles at IL1A(+4845) and/or IL1B(+3954) represents a pro-inflammatory genotype. For example, allele 2 at IL1B(+3954) is strongly associated with increased CRP in individuals presenting for cardiac catheterization. However, not all studies demonstrate such significance. One possibility is that IL1A(+4845) and IL1B(+3954) act only as surrogates for the causative genetic variants, possibly defined by IL1B haplotype pair groups. In fact, among our haplotype pairs groups associated with elevated logIL-1β expression, 84% carried a minor allele at both IL1A(+4845) and IL1B(−3954) compared to 23% in the remaining haplotype pair groups.

EQUIVALENTS AND INCORPORATION BY REFERENCE

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

The instant application includes numerous citations to learned texts, published articles and patent applications as well as issued U.S. and foreign patents. The entire contents of all of these citations are hereby incorporated by reference herein:

We claim:

1. A method for determining whether a subject has or is predisposed to an increased risk of having an increased expression level of IL-β protein comprising detecting a IL-1B (−511) allele and a IL-1RN (+2018) allele in the subject, wherein the presence of C/C at IL-1B (−511) allele indicates said subject has or is predisposed to an increased risk of having an increased expression level of IL-1β protein.

2. The method of claim 1, wherein said subject who possesses the C/C at IL-1B (−511) allele has or is predisposed to developing a disease or condition associated with an increased expression level of 1L-1β protein.

* * * * *

```
                        SEQUENCE LISTING

<160> NUMBER OF SEQ ID NOS: 260

<210> SEQ ID NO 1
<211> LENGTH: 25
<212> TYPE: DNA
<213> ORGANISM: Homo sapiens

<400> SEQUENCE: 1
gcatgagcca yggcacccag ccact                                          25

<210> SEQ ID NO 2
<211> LENGTH: 23
<212> TYPE: DNA
<213> ORGANISM: Homo sapiens

<400> SEQUENCE: 2
tgaactagaa ytcaagaaat tga                                            23

<210> SEQ ID NO 3
<211> LENGTH: 24
<212> TYPE: DNA
<213> ORGANISM: Homo sapiens

<400> SEQUENCE: 3
cacactctca yatgaattct ccat                                           24

<210> SEQ ID NO 4
<211> LENGTH: 23
<212> TYPE: DNA
<213> ORGANISM: Homo sapiens

<400> SEQUENCE: 4
catattctgg raccttcaat aaa                                            23

<210> SEQ ID NO 5
<211> LENGTH: 26
<212> TYPE: DNA
<213> ORGANISM: Homo sapiens

<400> SEQUENCE: 5
aaaagttatg yttttctctt cattca                                         26

<210> SEQ ID NO 6
<211> LENGTH: 23
<212> TYPE: DNA
<213> ORGANISM: Homo sapiens

<400> SEQUENCE: 6
tctttataag ycatcacttg gtg                                            23

<210> SEQ ID NO 7
<211> LENGTH: 25
<212> TYPE: DNA
<213> ORGANISM: Homo sapiens
```

-continued

```
<400> SEQUENCE: 7
cgagaggtgg rtgcctgaag ccacc                                           25

<210> SEQ ID NO 8
<211> LENGTH: 25
<212> TYPE: DNA
<213> ORGANISM: Homo sapiens

<400> SEQUENCE: 8
tgttcacagt yccagaaaag cgggc                                           25

<210> SEQ ID NO 9
<211> LENGTH: 25
<212> TYPE: DNA
<213> ORGANISM: Homo sapiens

<400> SEQUENCE: 9
taaagaggaa ycaaggtaag cagaa                                           25

<210> SEQ ID NO 10
<211> LENGTH: 25
<212> TYPE: DNA
<213> ORGANISM: Homo sapiens

<400> SEQUENCE: 10
acacaagctg ytttcctccc agatc                                           25

<210> SEQ ID NO 11
<211> LENGTH: 23
<212> TYPE: DNA
<213> ORGANISM: Homo sapiens

<400> SEQUENCE: 11
ccaggcaaca ycattgaagg ctc                                             23

<210> SEQ ID NO 12
<211> LENGTH: 24
<212> TYPE: DNA
<213> ORGANISM: Homo sapiens

<400> SEQUENCE: 12
aaagctacag yctctccttt cttt                                            24

<210> SEQ ID NO 13
<211> LENGTH: 23
<212> TYPE: DNA
<213> ORGANISM: Homo sapiens

<400> SEQUENCE: 13
ctgattcgtt wtactgaggg acg                                             23

<210> SEQ ID NO 14
<211> LENGTH: 25
<212> TYPE: DNA
<213> ORGANISM: Homo sapiens

<400> SEQUENCE: 14
actgagggac rgcagaacta gtttc                                           25

<210> SEQ ID NO 15
<211> LENGTH: 23
<212> TYPE: DNA
<213> ORGANISM: Homo sapiens
```

-continued

```
<400> SEQUENCE: 15
cttgaatctt maatactttt gtt                                           23

<210> SEQ ID NO 16
<211> LENGTH: 22
<212> TYPE: DNA
<213> ORGANISM: Homo sapiens

<400> SEQUENCE: 16
ctcactagag rtccagagac ct                                            22

<210> SEQ ID NO 17
<211> LENGTH: 20
<212> TYPE: DNA
<213> ORGANISM: Homo sapiens

<400> SEQUENCE: 17
aagaagagac rgttgagttt                                               20

<210> SEQ ID NO 18
<211> LENGTH: 20
<212> TYPE: DNA
<213> ORGANISM: Homo sapiens

<400> SEQUENCE: 18
tctggattgg matattccta                                               20

<210> SEQ ID NO 19
<211> LENGTH: 20
<212> TYPE: DNA
<213> ORGANISM: Homo sapiens

<400> SEQUENCE: 19
attcctaata ycccctccag                                               20

<210> SEQ ID NO 20
<211> LENGTH: 21
<212> TYPE: DNA
<213> ORGANISM: Homo sapiens

<400> SEQUENCE: 20
gcctaggtca kcaccttta g                                              21

<210> SEQ ID NO 21
<211> LENGTH: 20
<212> TYPE: DNA
<213> ORGANISM: Homo sapiens

<400> SEQUENCE: 21
gcccccacct vcccacccca                                               20

<210> SEQ ID NO 22
<211> LENGTH: 25
<212> TYPE: DNA
<213> ORGANISM: Homo sapiens

<400> SEQUENCE: 22
ccttttctca mcatcttgtt ctcta                                         25

<210> SEQ ID NO 23
<211> LENGTH: 21
<212> TYPE: DNA
<213> ORGANISM: Homo sapiens
```

-continued

```
<400> SEQUENCE: 23
tttgccttct rcttttaagt t                                                21

<210> SEQ ID NO 24
<211> LENGTH: 21
<212> TYPE: DNA
<213> ORGANISM: Homo sapiens

<400> SEQUENCE: 24
aaatacttct ygaagccgag c                                                21

<210> SEQ ID NO 25
<211> LENGTH: 22
<212> TYPE: DNA
<213> ORGANISM: Homo sapiens

<400> SEQUENCE: 25
ctgagtgtga scaggcatcc tc                                               22

<210> SEQ ID NO 26
<211> LENGTH: 23
<212> TYPE: DNA
<213> ORGANISM: Homo sapiens

<400> SEQUENCE: 26
gcctgggtcc yagacttgac aaa                                              23

<210> SEQ ID NO 27
<211> LENGTH: 20
<212> TYPE: DNA
<213> ORGANISM: Homo sapiens

<400> SEQUENCE: 27
agaaaagaca yagagtagga                                                  20

<210> SEQ ID NO 28
<211> LENGTH: 20
<212> TYPE: DNA
<213> ORGANISM: Homo sapiens

<400> SEQUENCE: 28
tccaaaggaa rgacaaggtc                                                  20

<210> SEQ ID NO 29
<211> LENGTH: 30
<212> TYPE: DNA
<213> ORGANISM: Homo sapiens

<400> SEQUENCE: 29
gggaggagaa tggaatgtyc cttggactct                                       30

<210> SEQ ID NO 30
<211> LENGTH: 23
<212> TYPE: DNA
<213> ORGANISM: Homo sapiens

<400> SEQUENCE: 30
gaagaagccc rttggagatg atg                                              23

<210> SEQ ID NO 31
<211> LENGTH: 25
<212> TYPE: DNA
<213> ORGANISM: Homo sapiens
```

```
<400> SEQUENCE: 31
gataactggc ygcgaagccc atgat                                         25

<210> SEQ ID NO 32
<211> LENGTH: 23
<212> TYPE: DNA
<213> ORGANISM: Homo sapiens

<400> SEQUENCE: 32
ggaagacagg rtctgataca tac                                           23

<210> SEQ ID NO 33
<211> LENGTH: 25
<212> TYPE: DNA
<213> ORGANISM: Homo sapiens

<400> SEQUENCE: 33
cctgtcactg rctttgatcc tcctt                                         25

<210> SEQ ID NO 34
<211> LENGTH: 25
<212> TYPE: DNA
<213> ORGANISM: Homo sapiens

<400> SEQUENCE: 34
atcctccttc rttcagcttg taatc                                         25

<210> SEQ ID NO 35
<211> LENGTH: 26
<212> TYPE: DNA
<213> ORGANISM: Homo sapiens

<400> SEQUENCE: 35
cactcccttg sataatgcag agcgag                                        26

<210> SEQ ID NO 36
<211> LENGTH: 23
<212> TYPE: DNA
<213> ORGANISM: Homo sapiens

<400> SEQUENCE: 36
agagagctcc ygaggcagag aac                                           23

<210> SEQ ID NO 37
<211> LENGTH: 29
<212> TYPE: DNA
<213> ORGANISM: Homo sapiens

<400> SEQUENCE: 37
ttttgaaagc yataaaaaca gcgagggag                                     29

<210> SEQ ID NO 38
<211> LENGTH: 30
<212> TYPE: DNA
<213> ORGANISM: Homo sapiens

<400> SEQUENCE: 38
gctctgggat yctcttcagc caatcttcat                                    30

<210> SEQ ID NO 39
<211> LENGTH: 28
<212> TYPE: DNA
<213> ORGANISM: Homo sapiens
```

```
<400> SEQUENCE: 39
actactttcc yattacaagt ccctccag                              28

<210> SEQ ID NO 40
<211> LENGTH: 25
<212> TYPE: DNA
<213> ORGANISM: Homo sapiens

<400> SEQUENCE: 40
aaattttgcc rcctcgcctc acgag                                 25

<210> SEQ ID NO 41
<211> LENGTH: 27
<212> TYPE: DNA
<213> ORGANISM: Homo sapiens

<400> SEQUENCE: 41
ctatcttctt ygacacatgg gataacg                               27

<210> SEQ ID NO 42
<211> LENGTH: 25
<212> TYPE: DNA
<213> ORGANISM: Homo sapiens

<400> SEQUENCE: 42
ccttctcccc rcccccatcc ctagg                                 25

<210> SEQ ID NO 43
<211> LENGTH: 24
<212> TYPE: DNA
<213> ORGANISM: Homo sapiens

<400> SEQUENCE: 43
atagcctgga mtttcctgtt gtct                                  24

<210> SEQ ID NO 44
<211> LENGTH: 28
<212> TYPE: DNA
<213> ORGANISM: Homo sapiens

<400> SEQUENCE: 44
ctttaattaa sactgaaaat atataagc                              28

<210> SEQ ID NO 45
<211> LENGTH: 23
<212> TYPE: DNA
<213> ORGANISM: Homo sapiens

<400> SEQUENCE: 45
cagtgcacat ytggaacagg atc                                   23

<210> SEQ ID NO 46
<211> LENGTH: 25
<212> TYPE: DNA
<213> ORGANISM: Homo sapiens

<400> SEQUENCE: 46
gttgggtcac rtacccgacg tgcta                                 25

<210> SEQ ID NO 47
<211> LENGTH: 25
<212> TYPE: DNA
<213> ORGANISM: Homo sapiens
```

<400> SEQUENCE: 47
actgttcaca kagccaagat atgga                                    25

<210> SEQ ID NO 48
<211> LENGTH: 25
<212> TYPE: DNA
<213> ORGANISM: Homo sapiens

<400> SEQUENCE: 48
tgtttgcttg ktcttctctc tcagc                                    25

<210> SEQ ID NO 49
<211> LENGTH: 25
<212> TYPE: DNA
<213> ORGANISM: Homo sapiens

<400> SEQUENCE: 49
agctgggtct rtgagttgtg gtggc                                    25

<210> SEQ ID NO 50
<211> LENGTH: 25
<212> TYPE: DNA
<213> ORGANISM: Homo sapiens

<400> SEQUENCE: 50
gtgtgtgtgt ytgtgtttgt gtgtg                                    25

<210> SEQ ID NO 51
<211> LENGTH: 25
<212> TYPE: DNA
<213> ORGANISM: Homo sapiens

<400> SEQUENCE: 51
gagagaatga raatatgagt ggtgg                                    25

<210> SEQ ID NO 52
<211> LENGTH: 25
<212> TYPE: DNA
<213> ORGANISM: Homo sapiens

<400> SEQUENCE: 52
tatcttgctc ytccattcct gatgc                                    25

<210> SEQ ID NO 53
<211> LENGTH: 25
<212> TYPE: DNA
<213> ORGANISM: Homo sapiens

<400> SEQUENCE: 53
gtcaccatca ytggggttgt ggatc                                    25

<210> SEQ ID NO 54
<211> LENGTH: 25
<212> TYPE: DNA
<213> ORGANISM: Homo sapiens

<400> SEQUENCE: 54
tgagccaagg yggaagagaa cagga                                    25

<210> SEQ ID NO 55
<211> LENGTH: 25
<212> TYPE: DNA
<213> ORGANISM: Homo sapiens

```
<400> SEQUENCE: 55
gcagatagca ycaggtccat tttgc                                          25

<210> SEQ ID NO 56
<211> LENGTH: 25
<212> TYPE: DNA
<213> ORGANISM: Homo sapiens

<400> SEQUENCE: 56
ctctcagaga sggcttccct ggcca                                          25

<210> SEQ ID NO 57
<211> LENGTH: 25
<212> TYPE: DNA
<213> ORGANISM: Homo sapiens

<400> SEQUENCE: 57
tctcagagag rgcttccctg gccac                                          25

<210> SEQ ID NO 58
<211> LENGTH: 26
<212> TYPE: DNA
<213> ORGANISM: Homo sapiens

<400> SEQUENCE: 58
tattttattt gytaacttgt ttcttg                                         26

<210> SEQ ID NO 59
<211> LENGTH: 25
<212> TYPE: DNA
<213> ORGANISM: Homo sapiens

<400> SEQUENCE: 59
gcacacatgc mtgagctggc ggcag                                          25

<210> SEQ ID NO 60
<211> LENGTH: 25
<212> TYPE: DNA
<213> ORGANISM: Homo sapiens

<400> SEQUENCE: 60
gggaggggag rctgggctcc tcctt                                          25

<210> SEQ ID NO 61
<211> LENGTH: 25
<212> TYPE: DNA
<213> ORGANISM: Homo sapiens

<400> SEQUENCE: 61
cccaggtact rcccgggtgc tactt                                          25

<210> SEQ ID NO 62
<211> LENGTH: 25
<212> TYPE: DNA
<213> ORGANISM: Homo sapiens

<400> SEQUENCE: 62
ggaagacctc rgaagacctc ctgtc                                          25

<210> SEQ ID NO 63
<211> LENGTH: 25
<212> TYPE: DNA
<213> ORGANISM: Homo sapiens
```

```
<400> SEQUENCE: 63
cctgtcctat saggccctcc ccatg                                           25

<210> SEQ ID NO 64
<211> LENGTH: 25
<212> TYPE: DNA
<213> ORGANISM: Homo sapiens

<400> SEQUENCE: 64
tctcattttt ycacctgaga aatga                                           25

<210> SEQ ID NO 65
<211> LENGTH: 25
<212> TYPE: DNA
<213> ORGANISM: Homo sapiens

<400> SEQUENCE: 65
ggaggcatcc rtgggagacc atgca                                           25

<210> SEQ ID NO 66
<211> LENGTH: 25
<212> TYPE: DNA
<213> ORGANISM: Homo sapiens

<400> SEQUENCE: 66
gtgcatactc kgactggaaa ctgga                                           25

<210> SEQ ID NO 67
<211> LENGTH: 25
<212> TYPE: DNA
<213> ORGANISM: Homo sapiens

<400> SEQUENCE: 67
aaaggataga satggaacca tgtgc                                           25

<210> SEQ ID NO 68
<211> LENGTH: 25
<212> TYPE: DNA
<213> ORGANISM: Homo sapiens

<400> SEQUENCE: 68
agggtaaatt mttttagga tccaa                                            25

<210> SEQ ID NO 69
<211> LENGTH: 25
<212> TYPE: DNA
<213> ORGANISM: Homo sapiens

<400> SEQUENCE: 69
aactagttgc yggatacttg caagg                                           25

<210> SEQ ID NO 70
<211> LENGTH: 25
<212> TYPE: DNA
<213> ORGANISM: Homo sapiens

<400> SEQUENCE: 70
gccaggaaag ycaatgtatg tgggc                                           25

<210> SEQ ID NO 71
<211> LENGTH: 25
<212> TYPE: DNA
<213> ORGANISM: Homo sapiens
```

```
<400> SEQUENCE: 71
caatgtatgt rggcatcacg tcact                                          25

<210> SEQ ID NO 72
<211> LENGTH: 25
<212> TYPE: DNA
<213> ORGANISM: Homo sapiens

<400> SEQUENCE: 72
cactttgccc stctgtctgc agcag                                          25

<210> SEQ ID NO 73
<211> LENGTH: 29
<212> TYPE: DNA
<213> ORGANISM: Homo sapiens

<400> SEQUENCE: 73
tgcacaaacc ctaggkcaat gtcctaatc                                      29

<210> SEQ ID NO 74
<211> LENGTH: 25
<212> TYPE: DNA
<213> ORGANISM: Homo sapiens

<400> SEQUENCE: 74
aaaccctagg tgcmatgtcc taatc                                          25

<210> SEQ ID NO 75
<211> LENGTH: 25
<212> TYPE: DNA
<213> ORGANISM: Homo sapiens

<400> SEQUENCE: 75
tgtattcaag yttgaagctg ggagg                                          25

<210> SEQ ID NO 76
<211> LENGTH: 25
<212> TYPE: DNA
<213> ORGANISM: Homo sapiens

<400> SEQUENCE: 76
attcaagttt raagctggga gggcc                                          25

<210> SEQ ID NO 77
<211> LENGTH: 25
<212> TYPE: DNA
<213> ORGANISM: Homo sapiens

<400> SEQUENCE: 77
aaaaataccc rgggtctctt catta                                          25

<210> SEQ ID NO 78
<211> LENGTH: 25
<212> TYPE: DNA
<213> ORGANISM: Homo sapiens

<400> SEQUENCE: 78
ttattgctgc ytcctcttct attaa                                          25

<210> SEQ ID NO 79
<211> LENGTH: 25
<212> TYPE: DNA
<213> ORGANISM: Homo sapiens
```

```
<400> SEQUENCE: 79
aaacaaccaa wattttttct tatga                                          25

<210> SEQ ID NO 80
<211> LENGTH: 25
<212> TYPE: DNA
<213> ORGANISM: Homo sapiens

<400> SEQUENCE: 80
gcagagtgcc wggcttgcgc tgggc                                          25

<210> SEQ ID NO 81
<211> LENGTH: 25
<212> TYPE: DNA
<213> ORGANISM: Homo sapiens

<400> SEQUENCE: 81
gcatggcggc kgacttccaa aaggg                                          25

<210> SEQ ID NO 82
<211> LENGTH: 25
<212> TYPE: DNA
<213> ORGANISM: Homo sapiens

<400> SEQUENCE: 82
cgcttattat racttctgct tgcat                                          25

<210> SEQ ID NO 83
<211> LENGTH: 25
<212> TYPE: DNA
<213> ORGANISM: Homo sapiens

<400> SEQUENCE: 83
aagccagtca ygtggctaag tctag                                          25

<210> SEQ ID NO 84
<211> LENGTH: 25
<212> TYPE: DNA
<213> ORGANISM: Homo sapiens

<400> SEQUENCE: 84
gctcagacag yggccccacc accag                                          25

<210> SEQ ID NO 85
<211> LENGTH: 25
<212> TYPE: DNA
<213> ORGANISM: Homo sapiens

<400> SEQUENCE: 85
aactagttgc yggatacttg caagg                                          25

<210> SEQ ID NO 86
<211> LENGTH: 25
<212> TYPE: DNA
<213> ORGANISM: Homo sapiens

<400> SEQUENCE: 86
gccaggaaag ycaatgtatg tgggc                                          25

<210> SEQ ID NO 87
<211> LENGTH: 25
<212> TYPE: DNA
<213> ORGANISM: Homo sapiens
```

```
<400> SEQUENCE: 87
caatgtatgt rggcatcacg tcact                                    25

<210> SEQ ID NO 88
<211> LENGTH: 25
<212> TYPE: DNA
<213> ORGANISM: Homo sapiens

<400> SEQUENCE: 88
cactttgccc stctgtctgc agcag                                    25

<210> SEQ ID NO 89
<211> LENGTH: 25
<212> TYPE: DNA
<213> ORGANISM: Homo sapiens

<400> SEQUENCE: 89
aaaccctagg tgcmatgtcc taatc                                    25

<210> SEQ ID NO 90
<211> LENGTH: 25
<212> TYPE: DNA
<213> ORGANISM: Homo sapiens

<400> SEQUENCE: 90
tgtattcaag yttgaagctg ggagg                                    25

<210> SEQ ID NO 91
<211> LENGTH: 25
<212> TYPE: DNA
<213> ORGANISM: Homo sapiens

<400> SEQUENCE: 91
attcaagttt raagctggga gggcc                                    25

<210> SEQ ID NO 92
<211> LENGTH: 25
<212> TYPE: DNA
<213> ORGANISM: Homo sapiens

<400> SEQUENCE: 92
aaaaataccc rgggtctctt catta                                    25

<210> SEQ ID NO 93
<211> LENGTH: 25
<212> TYPE: DNA
<213> ORGANISM: Homo sapiens

<400> SEQUENCE: 93
ttattgctgc ytcctcttct attaa                                    25

<210> SEQ ID NO 94
<211> LENGTH: 25
<212> TYPE: DNA
<213> ORGANISM: Homo sapiens

<400> SEQUENCE: 94
aaacaaccaa wattttttct tatga                                    25

<210> SEQ ID NO 95
<211> LENGTH: 25
<212> TYPE: DNA
<213> ORGANISM: Homo sapiens
```

<400> SEQUENCE: 95
gcagagtgcc wggcttgcgc tgggc                                              25

<210> SEQ ID NO 96
<211> LENGTH: 25
<212> TYPE: DNA
<213> ORGANISM: Homo sapiens

<400> SEQUENCE: 96
gcatggcggc kgacttccaa aaggg                                              25

<210> SEQ ID NO 97
<211> LENGTH: 25
<212> TYPE: DNA
<213> ORGANISM: Homo sapiens

<400> SEQUENCE: 97
cgcttattat racttctgct tgcat                                              25

<210> SEQ ID NO 98
<211> LENGTH: 25
<212> TYPE: DNA
<213> ORGANISM: Homo sapiens

<400> SEQUENCE: 98
aagccagtca ygtggctaag tctag                                              25

<210> SEQ ID NO 99
<211> LENGTH: 25
<212> TYPE: DNA
<213> ORGANISM: Homo sapiens

<400> SEQUENCE: 99
gctcagacag yggccccacc accag                                              25

<210> SEQ ID NO 100
<211> LENGTH: 25
<212> TYPE: DNA
<213> ORGANISM: Homo sapiens

<400> SEQUENCE: 100
ggcgtcacaa saacctggtc acagg                                              25

<210> SEQ ID NO 101
<211> LENGTH: 25
<212> TYPE: DNA
<213> ORGANISM: Homo sapiens
<220> FEATURE:
<221> NAME/KEY: modified_base
<222> LOCATION: (11)..(11)
<223> OTHER INFORMATION: may or may not be present

<400> SEQUENCE: 101
ctcccccacc aggctgggag ctctg                                              25

<210> SEQ ID NO 102
<211> LENGTH: 25
<212> TYPE: DNA
<213> ORGANISM: Homo sapiens

<400> SEQUENCE: 102
gcaaaaaaga yatggggcag cactg                                              25

<210> SEQ ID NO 103

```
<211> LENGTH: 25
<212> TYPE: DNA
<213> ORGANISM: Homo sapiens

<400> SEQUENCE: 103
aacagcctct rctggaaaca accca                                              25

<210> SEQ ID NO 104
<211> LENGTH: 25
<212> TYPE: DNA
<213> ORGANISM: Homo sapiens

<400> SEQUENCE: 104
aaagttccct rcttcctgtg acttc                                              25

<210> SEQ ID NO 105
<211> LENGTH: 14
<212> TYPE: DNA
<213> ORGANISM: Homo sapiens

<400> SEQUENCE: 105
cctgtcgccc cctg                                                          14

<210> SEQ ID NO 106
<211> LENGTH: 14
<212> TYPE: DNA
<213> ORGANISM: Homo sapiens

<400> SEQUENCE: 106
tctgtcgccc cctg                                                          14

<210> SEQ ID NO 107
<211> LENGTH: 14
<212> TYPE: DNA
<213> ORGANISM: Homo sapiens

<400> SEQUENCE: 107
cttgtcgccc cctg                                                          14

<210> SEQ ID NO 108
<211> LENGTH: 14
<212> TYPE: DNA
<213> ORGANISM: Homo sapiens

<400> SEQUENCE: 108
cccgtcgccc cctg                                                          14

<210> SEQ ID NO 109
<211> LENGTH: 14
<212> TYPE: DNA
<213> ORGANISM: Homo sapiens

<400> SEQUENCE: 109
cctttcgccc cctg                                                          14

<210> SEQ ID NO 110
<211> LENGTH: 14
<212> TYPE: DNA
<213> ORGANISM: Homo sapiens

<400> SEQUENCE: 110
cctgccgccc cctg                                                          14

<210> SEQ ID NO 111
```

```
<211> LENGTH: 14
<212> TYPE: DNA
<213> ORGANISM: Homo sapiens

<400> SEQUENCE: 111
cctgttgccc cctg                                                        14

<210> SEQ ID NO 112
<211> LENGTH: 12
<212> TYPE: DNA
<213> ORGANISM: Homo sapiens

<400> SEQUENCE: 112
ttgcataggg ct                                                          12

<210> SEQ ID NO 113
<211> LENGTH: 12
<212> TYPE: DNA
<213> ORGANISM: Homo sapiens

<400> SEQUENCE: 113
ctgcataggg ct                                                          12

<210> SEQ ID NO 114
<211> LENGTH: 11
<212> TYPE: DNA
<213> ORGANISM: Homo sapiens

<400> SEQUENCE: 114
tgcatagggc t                                                           11

<210> SEQ ID NO 115
<211> LENGTH: 11
<212> TYPE: DNA
<213> ORGANISM: Homo sapiens

<400> SEQUENCE: 115
cgcatagggc t                                                           11

<210> SEQ ID NO 116
<211> LENGTH: 11
<212> TYPE: DNA
<213> ORGANISM: Homo sapiens

<400> SEQUENCE: 116
tacatagggc t                                                           11

<210> SEQ ID NO 117
<211> LENGTH: 11
<212> TYPE: DNA
<213> ORGANISM: Homo sapiens

<400> SEQUENCE: 117
tgtatagggc t                                                           11

<210> SEQ ID NO 118
<211> LENGTH: 11
<212> TYPE: DNA
<213> ORGANISM: Homo sapiens

<400> SEQUENCE: 118
tgcgtagggc t                                                           11

<210> SEQ ID NO 119
```

```
<211> LENGTH: 11
<212> TYPE: DNA
<213> ORGANISM: Homo sapiens

<400> SEQUENCE: 119
tgcacagggc t                                                          11

<210> SEQ ID NO 120
<211> LENGTH: 11
<212> TYPE: DNA
<213> ORGANISM: Homo sapiens

<400> SEQUENCE: 120
tgcatggggc t                                                          11

<210> SEQ ID NO 121
<211> LENGTH: 11
<212> TYPE: DNA
<213> ORGANISM: Homo sapiens

<400> SEQUENCE: 121
tgcataaggc t                                                          11

<210> SEQ ID NO 122
<211> LENGTH: 11
<212> TYPE: DNA
<213> ORGANISM: Homo sapiens

<400> SEQUENCE: 122
tgcatagagc t                                                          11

<210> SEQ ID NO 123
<211> LENGTH: 11
<212> TYPE: DNA
<213> ORGANISM: Homo sapiens

<400> SEQUENCE: 123
tgcatagggc t                                                          11

<210> SEQ ID NO 124
<211> LENGTH: 11
<212> TYPE: DNA
<213> ORGANISM: Homo sapiens

<400> SEQUENCE: 124
tgcatagggt t                                                          11

<210> SEQ ID NO 125
<211> LENGTH: 11
<212> TYPE: DNA
<213> ORGANISM: Homo sapiens

<400> SEQUENCE: 125
tgcatagggc c                                                          11

<210> SEQ ID NO 126
<211> LENGTH: 12
<212> TYPE: DNA
<213> ORGANISM: Homo sapiens

<400> SEQUENCE: 126
tgcatagggc tc                                                         12

<210> SEQ ID NO 127
```

```
<211> LENGTH: 12
<212> TYPE: DNA
<213> ORGANISM: Homo sapiens

<400> SEQUENCE: 127
tgcatagggc tt                                                          12

<210> SEQ ID NO 128
<211> LENGTH: 12
<212> TYPE: DNA
<213> ORGANISM: Homo sapiens

<400> SEQUENCE: 128
ttgcataggg tc                                                          12

<210> SEQ ID NO 129
<211> LENGTH: 12
<212> TYPE: DNA
<213> ORGANISM: Homo sapiens

<400> SEQUENCE: 129
ctgcataggg tc                                                          12

<210> SEQ ID NO 130
<211> LENGTH: 11
<212> TYPE: DNA
<213> ORGANISM: Homo sapiens

<400> SEQUENCE: 130
tgcatagggt c                                                           11

<210> SEQ ID NO 131
<211> LENGTH: 11
<212> TYPE: DNA
<213> ORGANISM: Homo sapiens

<400> SEQUENCE: 131
cgcatagggt c                                                           11

<210> SEQ ID NO 132
<211> LENGTH: 11
<212> TYPE: DNA
<213> ORGANISM: Homo sapiens

<400> SEQUENCE: 132
tacatagggt c                                                           11

<210> SEQ ID NO 133
<211> LENGTH: 11
<212> TYPE: DNA
<213> ORGANISM: Homo sapiens

<400> SEQUENCE: 133
tgtatagggt c                                                           11

<210> SEQ ID NO 134
<211> LENGTH: 11
<212> TYPE: DNA
<213> ORGANISM: Homo sapiens

<400> SEQUENCE: 134
tgcgtagggt c                                                           11

<210> SEQ ID NO 135
```

```
<211> LENGTH: 11
<212> TYPE: DNA
<213> ORGANISM: Homo sapiens

<400> SEQUENCE: 135
tgcacagggt c                                                          11

<210> SEQ ID NO 136
<211> LENGTH: 11
<212> TYPE: DNA
<213> ORGANISM: Homo sapiens

<400> SEQUENCE: 136
tgcatggggt c                                                          11

<210> SEQ ID NO 137
<211> LENGTH: 11
<212> TYPE: DNA
<213> ORGANISM: Homo sapiens

<400> SEQUENCE: 137
tgcataaggt c                                                          11

<210> SEQ ID NO 138
<211> LENGTH: 11
<212> TYPE: DNA
<213> ORGANISM: Homo sapiens

<400> SEQUENCE: 138
tgcatagagt c                                                          11

<210> SEQ ID NO 139
<211> LENGTH: 11
<212> TYPE: DNA
<213> ORGANISM: Homo sapiens

<400> SEQUENCE: 139
tgcataggct c                                                          11

<210> SEQ ID NO 140
<211> LENGTH: 11
<212> TYPE: DNA
<213> ORGANISM: Homo sapiens

<400> SEQUENCE: 140
tgcatagggc c                                                          11

<210> SEQ ID NO 141
<211> LENGTH: 11
<212> TYPE: DNA
<213> ORGANISM: Homo sapiens

<400> SEQUENCE: 141
tgcatagggt t                                                          11

<210> SEQ ID NO 142
<211> LENGTH: 12
<212> TYPE: DNA
<213> ORGANISM: Homo sapiens

<400> SEQUENCE: 142
tgcatagggt ct                                                         12

<210> SEQ ID NO 143
```

```
<211> LENGTH: 12
<212> TYPE: DNA
<213> ORGANISM: Homo sapiens

<400> SEQUENCE: 143
tgcatagggt cc                                                          12

<210> SEQ ID NO 144
<211> LENGTH: 15
<212> TYPE: DNA
<213> ORGANISM: Homo sapiens

<400> SEQUENCE: 144
ttgcgctctg gcagg                                                       15

<210> SEQ ID NO 145
<211> LENGTH: 15
<212> TYPE: DNA
<213> ORGANISM: Homo sapiens

<400> SEQUENCE: 145
gtgcgctctg gcagg                                                       15

<210> SEQ ID NO 146
<211> LENGTH: 15
<212> TYPE: DNA
<213> ORGANISM: Homo sapiens

<400> SEQUENCE: 146
tggcgctctg gcagg                                                       15

<210> SEQ ID NO 147
<211> LENGTH: 15
<212> TYPE: DNA
<213> ORGANISM: Homo sapiens

<400> SEQUENCE: 147
ttacgctctg gcagg                                                       15

<210> SEQ ID NO 148
<211> LENGTH: 15
<212> TYPE: DNA
<213> ORGANISM: Homo sapiens

<400> SEQUENCE: 148
ttgtgctctg gcagg                                                       15

<210> SEQ ID NO 149
<211> LENGTH: 15
<212> TYPE: DNA
<213> ORGANISM: Homo sapiens

<400> SEQUENCE: 149
ttgcactctg gcagg                                                       15

<210> SEQ ID NO 150
<211> LENGTH: 10
<212> TYPE: DNA
<213> ORGANISM: Homo sapiens

<400> SEQUENCE: 150
ctctggcagg                                                             10

<210> SEQ ID NO 151
```

```
<211> LENGTH: 10
<212> TYPE: DNA
<213> ORGANISM: Homo sapiens

<400> SEQUENCE: 151
ttctggcagg                                                            10

<210> SEQ ID NO 152
<211> LENGTH: 10
<212> TYPE: DNA
<213> ORGANISM: Homo sapiens

<400> SEQUENCE: 152
ccctggcagg                                                            10

<210> SEQ ID NO 153
<211> LENGTH: 10
<212> TYPE: DNA
<213> ORGANISM: Homo sapiens

<400> SEQUENCE: 153
ctttggcagg                                                            10

<210> SEQ ID NO 154
<211> LENGTH: 10
<212> TYPE: DNA
<213> ORGANISM: Homo sapiens

<400> SEQUENCE: 154
ctccggcagg                                                            10

<210> SEQ ID NO 155
<211> LENGTH: 12
<212> TYPE: DNA
<213> ORGANISM: Homo sapiens

<400> SEQUENCE: 155
ctctggcagg ag                                                         12

<210> SEQ ID NO 156
<211> LENGTH: 12
<212> TYPE: DNA
<213> ORGANISM: Homo sapiens

<400> SEQUENCE: 156
ctctggcagg gg                                                         12

<210> SEQ ID NO 157
<211> LENGTH: 12
<212> TYPE: DNA
<213> ORGANISM: Homo sapiens

<400> SEQUENCE: 157
ctctggcagg ac                                                         12

<210> SEQ ID NO 158
<211> LENGTH: 30
<212> TYPE: DNA
<213> ORGANISM: Homo sapiens

<400> SEQUENCE: 158
gagatgcctg agataacatt aattaccttg                                      30

<210> SEQ ID NO 159
```

```
<211> LENGTH: 30
<212> TYPE: DNA
<213> ORGANISM: Homo sapiens

<400> SEQUENCE: 159
tgaaatttga catggccagt gctgctgaag                                    30

<210> SEQ ID NO 160
<211> LENGTH: 30
<212> TYPE: DNA
<213> ORGANISM: Homo sapiens

<400> SEQUENCE: 160
aaatcatcaa gcctaatctg gatgaagcag                                    30

<210> SEQ ID NO 161
<211> LENGTH: 30
<212> TYPE: DNA
<213> ORGANISM: Homo sapiens

<400> SEQUENCE: 161
aaatccttct atcatatgac tcagaggaag                                    30

<210> SEQ ID NO 162
<211> LENGTH: 30
<212> TYPE: DNA
<213> ORGANISM: Homo sapiens

<400> SEQUENCE: 162
tgaaaatgaa gaagactgtc tctgaatcag                                    30

<210> SEQ ID NO 163
<211> LENGTH: 30
<212> TYPE: DNA
<213> ORGANISM: Homo sapiens

<400> SEQUENCE: 163
aagtcaagat ggccagaaga actgttacag                                    30

<210> SEQ ID NO 164
<211> LENGTH: 30
<212> TYPE: DNA
<213> ORGANISM: Homo sapiens

<400> SEQUENCE: 164
aagctgccag ccagatttga gtcagcaaag                                    30

<210> SEQ ID NO 165
<211> LENGTH: 16
<212> TYPE: PRT
<213> ORGANISM: Homo sapiens

<400> SEQUENCE: 165

Met Ala Lys Val Pro Asp Met Phe Glu Asp Leu Lys Asn Cys Tyr Ser
1               5                   10                  15

<210> SEQ ID NO 166
<211> LENGTH: 16
<212> TYPE: PRT
<213> ORGANISM: Homo sapiens

<400> SEQUENCE: 166

Glu Asn Glu Glu Asp Ser Ser Ser Ile Asp His Leu Ser Leu Asn Gly
1               5                   10                  15
```

<210> SEQ ID NO 167
<211> LENGTH: 75
<212> TYPE: PRT
<213> ORGANISM: Homo sapiens

<400> SEQUENCE: 167

Lys Ser Phe Tyr His Val Ser Tyr Gly Pro Leu His Glu Gly Cys Met
1               5                   10                  15

Asp Gln Ser Val Ser Leu Ser Ile Ser Glu Thr Ser Lys Thr Ser Lys
            20                  25                  30

Leu Thr Phe Lys Glu Ser Met Val Val Ala Thr Asn Gly Lys Val
        35                  40                  45

Leu Lys Lys Arg Arg Leu Ser Leu Ser Gln Ser Ile Thr Asp Asp Asp
50                  55                  60

Leu Glu Ala Ile Ala Asn Asp Ser Glu Glu Glu
65                  70                  75

<210> SEQ ID NO 168
<211> LENGTH: 57
<212> TYPE: PRT
<213> ORGANISM: Homo sapiens

<400> SEQUENCE: 168

Ile Ile Lys Pro Arg Ser Ala Pro Phe Ser Phe Leu Ser Asn Val Lys
1               5                   10                  15

Tyr Asn Phe Met Arg Ile Ile Lys Tyr Glu Phe Ile Leu Asn Asp Ala
            20                  25                  30

Leu Asn Gln Ser Ile Ile Arg Ala Asn Asp Gln Tyr Leu Thr Ala Ala
        35                  40                  45

Ala Leu His Asn Leu Asp Glu Ala Val
50                  55

<210> SEQ ID NO 169
<211> LENGTH: 41
<212> TYPE: PRT
<213> ORGANISM: Homo sapiens

<400> SEQUENCE: 169

Lys Phe Asp Met Gly Ala Tyr Lys Ser Ser Lys Asp Asp Ala Lys Ile
1               5                   10                  15

Thr Val Ile Leu Arg Ile Ser Lys Thr Gln Leu Tyr Val Thr Ala Gln
            20                  25                  30

Asp Glu Asp Gln Pro Val Leu Leu Lys
        35                  40

<210> SEQ ID NO 170
<211> LENGTH: 66
<212> TYPE: PRT
<213> ORGANISM: Homo sapiens

<400> SEQUENCE: 170

Glu Met Pro Glu Ile Pro Lys Thr Ile Thr Gly Ser Glu Thr Asn Leu
1               5                   10                  15

Leu Phe Phe Trp Glu Thr His Gly Thr Lys Asn Tyr Phe Thr Ser Val
            20                  25                  30

Ala His Pro Asn Leu Phe Ile Ala Thr Lys Gln Asp Tyr Trp Val Cys
        35                  40                  45

Leu Ala Gly Gly Pro Pro Ser Ile Thr Asp Phe Gln Ile Leu Glu Asn
50                  55                  60

Gln Ala
65

<210> SEQ ID NO 171
<211> LENGTH: 30
<212> TYPE: DNA
<213> ORGANISM: Homo sapiens

<400> SEQUENCE: 171
agtgtagatc ccaaataaac ttcactgaag                                          30

<210> SEQ ID NO 172
<211> LENGTH: 30
<212> TYPE: DNA
<213> ORGANISM: Homo sapiens

<400> SEQUENCE: 172
tggtgttctc catgtactct acagctggag                                          30

<210> SEQ ID NO 173
<211> LENGTH: 30
<212> TYPE: DNA
<213> ORGANISM: Homo sapiens

<400> SEQUENCE: 173
aacctatctt cttcgatatg gagcaacaag                                          30

<210> SEQ ID NO 174
<211> LENGTH: 30
<212> TYPE: DNA
<213> ORGANISM: Homo sapiens

<400> SEQUENCE: 174
tgctccttcc aggactcatc tttgaagaag                                          30

<210> SEQ ID NO 175
<211> LENGTH: 30
<212> TYPE: DNA
<213> ORGANISM: Homo sapiens

<400> SEQUENCE: 175
tggcaatgag gatgacctaa acagatgaag                                          30

<210> SEQ ID NO 176
<211> LENGTH: 30
<212> TYPE: DNA
<213> ORGANISM: Homo sapiens

<400> SEQUENCE: 176
gtgtctggaa gcagcgatgg cttattacag                                          30

<210> SEQ ID NO 177
<211> LENGTH: 30
<212> TYPE: DNA
<213> ORGANISM: Homo sapiens

<400> SEQUENCE: 177
accaacctct tcgagatctt cattgctcaa                                          30

<210> SEQ ID NO 178
<211> LENGTH: 16
<212> TYPE: PRT
<213> ORGANISM: Homo sapiens

<400> SEQUENCE: 178

```
Met Ala Glu Val Pro Lys Leu Ala Ser Glu Met Met Ala Tyr Tyr Ser
1               5                   10                  15
```

<210> SEQ ID NO 179
<211> LENGTH: 17
<212> TYPE: PRT
<213> ORGANISM: Homo sapiens

<400> SEQUENCE: 179

```
Gly Asn Glu His Asp Leu Phe Phe Glu Ala Asp Gly Pro Lys Gln Met
1               5                   10                  15

Lys
```

<210> SEQ ID NO 180
<211> LENGTH: 68
<212> TYPE: PRT
<213> ORGANISM: Homo sapiens

<400> SEQUENCE: 180

```
Cys Ser Phe Gln Asp Leu Asp Leu Cys Pro Leu Asp Gly Gly Ile Gln
1               5                   10                  15

Leu Arg Ile Ser Asp His His Tyr Ser Lys Gly Phe Arg Gln Ala Ala
            20                  25                  30

Ser Val Val Ala Met Asp Lys Leu Arg Lys Met Leu Val Pro Cys
        35                  40                  45

Pro Gln Thr Phe Gln Glu Asn Asp Leu Ser Thr Phe Phe Pro Phe Ile
    50                  55                  60

Phe Glu Glu Glu
65
```

<210> SEQ ID NO 181
<211> LENGTH: 55
<212> TYPE: PRT
<213> ORGANISM: Homo sapiens

<400> SEQUENCE: 181

```
Pro Ile Phe Phe Asp Thr Trp Asp Asn Gln Ala Tyr Val His Asp Ala
1               5                   10                  15

Pro Val Arg Ser Leu Asn Cys Thr Leu Arg Asp Ser Gln Gln Lys Ser
            20                  25                  30

Leu Val Met Ser Gly Pro Tyr Glu Leu Lys Ala Leu His Leu Gln Gly
        35                  40                  45

Gln Asp Met Glu Gln Gly Val
    50                  55
```

<210> SEQ ID NO 182
<211> LENGTH: 43
<212> TYPE: PRT
<213> ORGANISM: Homo sapiens

<400> SEQUENCE: 182

```
Val Phe Ser Met Ser Phe Val Gln Gly Glu Glu Ser Asn Asp Lys Ile
1               5                   10                  15

Pro Val Ala Leu Ala Leu Lys Glu Lys Asn Leu Tyr Leu Ser Cys Val
            20                  25                  30

Leu Lys Asp Asp Lys Pro Thr Leu Gln Leu Glu
        35                  40
```

<210> SEQ ID NO 183
<211> LENGTH: 70

```
<212> TYPE: PRT
<213> ORGANISM: Homo sapiens

<400> SEQUENCE: 183

Ser Val Asp Pro Lys Asn Tyr Pro Lys Lys Met Glu Lys Pro Phe
1               5                   10                  15

Val Phe Asn Lys Ile Glu Ile Asn Asn Lys Leu Glu Phe Glu Ser Ala
            20                  25                  30

Gln Phe Pro Asn Trp Tyr Ile Ser Thr Ser Gln Ala Glu Asn Met Pro
        35                  40                  45

Val Phe Leu Gly Gly Thr Lys Gly Gly Gln Asp Ile Thr Asp Phe Thr
    50                  55                  60

Met Gln Phe Val Ser Ser
65                  70

<210> SEQ ID NO 184
<211> LENGTH: 30
<212> TYPE: DNA
<213> ORGANISM: Homo sapiens

<400> SEQUENCE: 184
cttcattcca ttttcagtgc tgcttagaag                                30

<210> SEQ ID NO 185
<211> LENGTH: 30
<212> TYPE: DNA
<213> ORGANISM: Homo sapiens

<400> SEQUENCE: 185
acccggctgg aagccatttt gttcacacaa                                30

<210> SEQ ID NO 186
<211> LENGTH: 30
<212> TYPE: DNA
<213> ORGANISM: Homo sapiens

<400> SEQUENCE: 186
atgtcaggct gtgatagaag cgcttaagag                                30

<210> SEQ ID NO 187
<211> LENGTH: 30
<212> TYPE: DNA
<213> ORGANISM: Homo sapiens

<400> SEQUENCE: 187
gtccaaaggt gaagaactac atacgcccag                                30

<210> SEQ ID NO 188
<211> LENGTH: 30
<212> TYPE: DNA
<213> ORGANISM: Homo sapiens

<400> SEQUENCE: 188
agatcttctt tgcattccct tcagctgaag                                30

<210> SEQ ID NO 189
<211> LENGTH: 30
<212> TYPE: DNA
<213> ORGANISM: Homo sapiens

<400> SEQUENCE: 189
aaggagaaac tgatgaacct gctcactaaa                                30
```

```
<210> SEQ ID NO 190
<211> LENGTH: 28
<212> TYPE: PRT
<213> ORGANISM: Homo sapiens

<400> SEQUENCE: 190

Met Ser Phe Val Gly Glu Asn Ser Gly Val Lys Met Gly Ser Glu Asp
1               5                   10                  15

Trp Glu Lys Asp Glu Pro Gln Cys Cys Leu Glu Asp
            20                  25

<210> SEQ ID NO 191
<211> LENGTH: 21
<212> TYPE: PRT
<213> ORGANISM: Homo sapiens
<220> FEATURE:
<221> NAME/KEY: MOD_RES
<222> LOCATION: (21)..(21)
<223> OTHER INFORMATION: Ser or Lys

<400> SEQUENCE: 191

Pro Ala Gly Ser Pro Leu Glu Pro Gly Pro Ser Leu Pro Thr Met Asn
1               5                   10                  15

Phe Val His Thr Xaa
            20

<210> SEQ ID NO 192
<211> LENGTH: 23
<212> TYPE: PRT
<213> ORGANISM: Homo sapiens

<400> SEQUENCE: 192

Met Ser Gly Cys Asp Arg Arg Glu Thr Glu Thr Lys Gly Lys Asn Ser
1               5                   10                  15

Phe Lys Lys Arg Leu Arg Gly
            20

<210> SEQ ID NO 193
<211> LENGTH: 40
<212> TYPE: PRT
<213> ORGANISM: Homo sapiens

<400> SEQUENCE: 193

Pro Lys Val Lys Asn Leu Asn Pro Lys Lys Phe Ser Ile His Asp Gln
1               5                   10                  15

Asp His Lys Val Leu Val Leu Asp Ser Gly Asn Leu Ile Ala Val Pro
            20                  25                  30

Asp Lys Asn Tyr Ile Arg Pro Glu
        35                  40

<210> SEQ ID NO 194
<211> LENGTH: 45
<212> TYPE: PRT
<213> ORGANISM: Homo sapiens

<400> SEQUENCE: 194

Ile Phe Phe Ala Leu Ala Ser Ser Leu Ser Ser Ala Ser Ala Glu Lys
1               5                   10                  15

Gly Ser Pro Ile Leu Leu Gly Val Ser Lys Gly Glu Phe Cys Leu Tyr
            20                  25                  30

Cys Asp Lys Asp Lys Gly Gln Ser His Leu Gln Leu Lys
        35                  40                  45
```

<210> SEQ ID NO 195
<211> LENGTH: 80
<212> TYPE: PRT
<213> ORGANISM: Homo sapiens

<400> SEQUENCE: 195

Lys Glu Lys Leu Met Lys Leu Ala Ala Gln Lys Glu Ser Ala Arg Arg
1               5                   10                  15

Pro Phe Ile Phe Tyr Arg Ala Gln Val Gly Ser Trp Asn Met Leu Glu
            20                  25                  30

Ser Ala His Pro Gly Trp Phe Ile Cys Thr Ser Cys Asn Cys Asn
        35                  40                  45

Glu Pro Val Gly Val Thr Asp Lys Phe Glu Asn Arg Lys His Ile Glu
    50                  55                  60

Phe Ser Phe Gln Pro Val Cys Lys Ala Glu Met Ser Glu Val Ser Asp
65                  70                  75                  80

<210> SEQ ID NO 196
<211> LENGTH: 30
<212> TYPE: DNA
<213> ORGANISM: Homo sapiens

<400> SEQUENCE: 196
gagccacgat tcagtaccct ttcttgccag                                    30

<210> SEQ ID NO 197
<211> LENGTH: 30
<212> TYPE: DNA
<213> ORGANISM: Homo sapiens

<400> SEQUENCE: 197
gtgctgagac aaccaccgtc tatcaatcaa                                    30

<210> SEQ ID NO 198
<211> LENGTH: 30
<212> TYPE: DNA
<213> ORGANISM: Homo sapiens

<400> SEQUENCE: 198
tgtgtaaacc tattaacagt gtgaccccag                                    30

<210> SEQ ID NO 199
<211> LENGTH: 30
<212> TYPE: DNA
<213> ORGANISM: Homo sapiens

<400> SEQUENCE: 199
tcactgttgc tgttaacatt gcagctaaaa                                    30

<210> SEQ ID NO 200
<211> LENGTH: 30
<212> TYPE: DNA
<213> ORGANISM: Homo sapiens

<400> SEQUENCE: 200
gagcagaaga tcatgctaaa actgatataa                                    30

<210> SEQ ID NO 201
<211> LENGTH: 19
<212> TYPE: PRT
<213> ORGANISM: Homo sapiens

<400> SEQUENCE: 201

```
Met Arg Gly Thr Pro Gly Asp Ala Asp Gly Gly Arg Ala Val Tyr
1               5                   10                  15

Gln Ser Met

<210> SEQ ID NO 202
<211> LENGTH: 35
<212> TYPE: PRT
<213> ORGANISM: Homo sapiens

<400> SEQUENCE: 202

Cys Lys Pro Ile Thr Gly Thr Ile Asn Asp Leu Asn Gln Gln Val Trp
1               5                   10                  15

Thr Leu Gln Gly Gln Asn Leu Val Ala Val Pro Arg Ser Asp Ser Val
                20                  25                  30

Thr Pro Val
        35

<210> SEQ ID NO 203
<211> LENGTH: 46
<212> TYPE: PRT
<213> ORGANISM: Homo sapiens

<400> SEQUENCE: 203

Thr Val Ala Val Ile Thr Cys Lys Tyr Pro Glu Ala Leu Glu Gln Gly
1               5                   10                  15

Arg Gly Asp Pro Ile Tyr Leu Gly Ile Gln Asn Pro Glu Met Cys Leu
                20                  25                  30

Tyr Cys Glu Lys Val Gly Glu Gln Pro Thr Leu Gln Leu Lys
            35                  40                  45

<210> SEQ ID NO 204
<211> LENGTH: 69
<212> TYPE: PRT
<213> ORGANISM: Homo sapiens

<400> SEQUENCE: 204

Glu Gln Lys Ile Met Asp Leu Tyr Gly Gln Pro Glu Pro Val Lys Pro
1               5                   10                  15

Phe Leu Phe Tyr Arg Ala Lys Thr Gly Arg Thr Ser Thr Leu Glu Ser
                20                  25                  30

Val Ala Phe Pro Asp Trp Phe Ile Ala Ser Ser Lys Arg Asp Gln Pro
            35                  40                  45

Ile Ile Leu Thr Ser Glu Leu Gly Lys Ser Tyr Asn Thr Ala Phe Glu
        50                  55                  60

Leu Asn Ile Asn Asp
65

<210> SEQ ID NO 205
<211> LENGTH: 10
<212> TYPE: DNA
<213> ORGANISM: Homo sapiens

<400> SEQUENCE: 205
atggaaaaag                                                          10

<210> SEQ ID NO 206
<211> LENGTH: 30
<212> TYPE: DNA
<213> ORGANISM: Homo sapiens

<400> SEQUENCE: 206
```

```
cattgaaaat tgacaaccgt atgtctccag                              30
```

<210> SEQ ID NO 207
<211> LENGTH: 30
<212> TYPE: DNA
<213> ORGANISM: Homo sapiens

<400> SEQUENCE: 207

```
tcactattgc cttaaacact gcagctgaag                              30
```

<210> SEQ ID NO 208
<211> LENGTH: 30
<212> TYPE: DNA
<213> ORGANISM: Homo sapiens

<400> SEQUENCE: 208

```
gaaaaggata taatgactat gctgttttaa                              30
```

<210> SEQ ID NO 209
<211> LENGTH: 4
<212> TYPE: PRT
<213> ORGANISM: Homo sapiens

<400> SEQUENCE: 209

Met Glu Lys Ala
1

<210> SEQ ID NO 210
<211> LENGTH: 38
<212> TYPE: PRT
<213> ORGANISM: Homo sapiens

<400> SEQUENCE: 210

Leu Lys Ile Asp Thr Pro Gln Gln Gly Ser Ile Gln Asp Ile Asn His
1               5                   10                  15

Arg Val Trp Val Leu Gln Asp Gln Thr Leu Ile Ala Val Pro Arg Lys
            20                  25                  30

Asp Arg Met Ser Pro Val
        35

<210> SEQ ID NO 211
<211> LENGTH: 46
<212> TYPE: PRT
<213> ORGANISM: Homo sapiens

<400> SEQUENCE: 211

Thr Ile Ala Leu Ile Ser Cys Arg His Val Glu Thr Leu Glu Lys Asp
1               5                   10                  15

Arg Gly Asn Pro Ile Tyr Leu Gly Leu Asn Gly Leu Asn Leu Cys Leu
            20                  25                  30

Met Cys Ala Lys Val Gly Asp Gln Pro Thr Leu Gln Leu Lys
        35                  40                  45

<210> SEQ ID NO 212
<211> LENGTH: 70
<212> TYPE: PRT
<213> ORGANISM: Homo sapiens

<400> SEQUENCE: 212

Glu Lys Asp Ile Met Asp Leu Tyr Asn Gln Pro Glu Pro Val Lys Ser
1               5                   10                  15

Phe Leu Phe Tyr His Ser Gln Ser Gly Arg Asn Ser Thr Phe Glu Ser

```
                    20                  25                  30
Val Ala Phe Pro Gly Trp Phe Ile Ala Val Ser Ser Glu Gly Gly Cys
            35                  40                  45

Pro Leu Ile Leu Thr Gln Glu Leu Gly Lys Ala Asn Thr Thr Asp Phe
        50                  55                  60

Gly Leu Thr Met Leu Phe
65                  70

<210> SEQ ID NO 213
<211> LENGTH: 30
<212> TYPE: DNA
<213> ORGANISM: Homo sapiens

<400> SEQUENCE: 213
gtagaaagaa gtggatagtt tttcccatgt                                        30

<210> SEQ ID NO 214
<211> LENGTH: 30
<212> TYPE: DNA
<213> ORGANISM: Homo sapiens

<400> SEQUENCE: 214
cttcagggct cccaagggga ataggagtgg                                        30

<210> SEQ ID NO 215
<211> LENGTH: 30
<212> TYPE: DNA
<213> ORGANISM: Homo sapiens

<400> SEQUENCE: 215
gaaaaaaata tcatggattc tgtggaataa                                        30

<210> SEQ ID NO 216
<211> LENGTH: 30
<212> TYPE: DNA
<213> ORGANISM: Homo sapiens

<400> SEQUENCE: 216
tcactcttca tttaaacttt gcagcttaag                                        30

<210> SEQ ID NO 217
<211> LENGTH: 30
<212> TYPE: DNA
<213> ORGANISM: Homo sapiens

<400> SEQUENCE: 217
gggaggcagc acccagcagc attaagcctg                                        30

<210> SEQ ID NO 218
<211> LENGTH: 30
<212> TYPE: DNA
<213> ORGANISM: Homo sapiens

<400> SEQUENCE: 218
cctcctcacc accattcatg aacccacaac                                        30

<210> SEQ ID NO 219
<211> LENGTH: 30
<212> TYPE: DNA
<213> ORGANISM: Homo sapiens

<400> SEQUENCE: 219
gacacgggtt cctcccttca cttttcctag                                        30
```

<210> SEQ ID NO 220
<211> LENGTH: 5
<212> TYPE: PRT
<213> ORGANISM: Homo sapiens

<400> SEQUENCE: 220

Met Asn Pro Gln Arg
1               5

<210> SEQ ID NO 221
<211> LENGTH: 36
<212> TYPE: PRT
<213> ORGANISM: Homo sapiens

<400> SEQUENCE: 221

Glu Ala Ala Pro Lys Ser Tyr Ala Ile Arg Asp Ser Arg Gln Met Val
1               5                   10                  15

Trp Val Leu Ser Gly Asn Ser Leu Ile Ala Ala Pro Leu Ser Arg Ser
            20                  25                  30

Ile Lys Pro Val
        35

<210> SEQ ID NO 222
<211> LENGTH: 46
<212> TYPE: PRT
<213> ORGANISM: Homo sapiens

<400> SEQUENCE: 222

Thr Leu His Leu Ile Ala Cys Arg Asp Thr Glu Phe Ser Asp Lys Glu
1               5                   10                  15

Lys Gly Asn Met Val Tyr Leu Gly Ile Lys Gly Lys Asp Leu Cys Leu
            20                  25                  30

Phe Cys Ala Glu Ile Gln Gly Lys Pro Thr Leu Gln Leu Lys
        35                  40                  45

<210> SEQ ID NO 223
<211> LENGTH: 70
<212> TYPE: PRT
<213> ORGANISM: Homo sapiens

<400> SEQUENCE: 223

Glu Lys Asn Ile Met Asp Leu Tyr Val Glu Lys Lys Ala Gln Lys Pro
1               5                   10                  15

Phe Leu Phe Phe His Asn Lys Glu Gly Ser Thr Ser Val Phe Gln Ser
            20                  25                  30

Val Ser Tyr Pro Gly Trp Phe Ile Ala Thr Ser Thr Thr Ser Gly Gln
        35                  40                  45

Pro Ile Phe Leu Thr Lys Glu Arg Gly Ile Thr Asn Asn Thr Asn Phe
    50                  55                  60

Tyr Leu Asp Ser Val Glu
65                  70

<210> SEQ ID NO 224
<211> LENGTH: 44
<212> TYPE: PRT
<213> ORGANISM: Homo sapiens

<400> SEQUENCE: 224

Leu Gln Gly Ser Gln Asp Asn Ile Gly Lys Asp Thr Cys Trp Lys Leu
1               5                   10                  15

Val Gly Ile His Thr Cys Ile Asn Leu Asp Val Arg Glu Ser Cys Phe
            20                  25                  30

Met Gly Thr Leu Asp Gln Trp Gly Ile Gly Val Gly
        35                  40

<210> SEQ ID NO 225
<211> LENGTH: 33
<212> TYPE: PRT
<213> ORGANISM: Homo sapiens

<400> SEQUENCE: 225

Arg Lys Lys Trp Lys Ser Ser Phe Gln His His His Leu Arg Lys Lys
1               5                   10                  15

Asp Lys Asp Phe Ser Ser Met Arg Thr Asn Ile Gly Met Pro Gly Arg
            20                  25                  30

Met

<210> SEQ ID NO 226
<211> LENGTH: 30
<212> TYPE: DNA
<213> ORGANISM: Homo sapiens

<400> SEQUENCE: 226
aaggaaggag ggagagaagg agtgaaaaag                                    30

<210> SEQ ID NO 227
<211> LENGTH: 30
<212> TYPE: DNA
<213> ORGANISM: Homo sapiens

<400> SEQUENCE: 227
cgctgggaat cctgcaagga acattctgag                                    30

<210> SEQ ID NO 228
<211> LENGTH: 30
<212> TYPE: DNA
<213> ORGANISM: Homo sapiens

<400> SEQUENCE: 228
gggagtctac accctggcgc tgtgcttccg                                    30

<210> SEQ ID NO 229
<211> LENGTH: 30
<212> TYPE: DNA
<213> ORGANISM: Homo sapiens

<400> SEQUENCE: 229
aatgaaggac tcggcggaag gtcattaaag                                    30

<210> SEQ ID NO 230
<211> LENGTH: 30
<212> TYPE: DNA
<213> ORGANISM: Homo sapiens

<400> SEQUENCE: 230
gtgaagagat cagcgactct aacactagag                                    30

<210> SEQ ID NO 231
<211> LENGTH: 30
<212> TYPE: DNA
<213> ORGANISM: Homo sapiens

<400> SEQUENCE: 231

```
ccagtgaaca tcatgagaaa gagaaacaaa                                          30
```

<210> SEQ ID NO 232
<211> LENGTH: 16
<212> TYPE: PRT
<213> ORGANISM: Homo sapiens

<400> SEQUENCE: 232

```
Met Ala Gly Arg Lys Asp Arg Gly Arg Lys Glu Gly Glu Gly Lys Glu
1               5                   10                  15
```

<210> SEQ ID NO 233
<211> LENGTH: 10
<212> TYPE: PRT
<213> ORGANISM: Homo sapiens

<400> SEQUENCE: 233

```
Met Val Leu Ser Gly Ala Leu Cys Phe Arg
1               5                   10
```

<210> SEQ ID NO 234
<211> LENGTH: 29
<212> TYPE: PRT
<213> ORGANISM: Homo sapiens

<400> SEQUENCE: 234

```
Met Lys Asp Ser Ala Leu Lys Val Leu Tyr Leu His Asn Asn Gln Leu
1               5                   10                  15

Leu Ala Gly Gly Leu His Ala Gly Lys Val Ile Lys Gly
            20                  25
```

<210> SEQ ID NO 235
<211> LENGTH: 42
<212> TYPE: PRT
<213> ORGANISM: Homo sapiens

<400> SEQUENCE: 235

```
Glu Glu Ile Ser Val Val Pro Asn Arg Trp Leu Asp Ala Ser Leu Ser
1               5                   10                  15

Pro Val Ile Leu Gly Val Gln Gly Gly Ser Gln Cys Leu Ser Cys Gly
            20                  25                  30

Val Gly Gln Glu Pro Thr Leu Thr Leu Glu
        35                  40
```

<210> SEQ ID NO 236
<211> LENGTH: 74
<212> TYPE: PRT
<213> ORGANISM: Homo sapiens

<400> SEQUENCE: 236

```
Pro Val Asn Ile Met Glu Leu Tyr Leu Gly Ala Lys Glu Ser Lys Ser
1               5                   10                  15

Phe Thr Phe Tyr Arg Arg Asp Met Gly Leu Thr Ser Ser Phe Glu Ser
            20                  25                  30

Ala Ala Tyr Pro Gly Trp Phe Leu Cys Thr Val Pro Glu Ala Asp Gln
        35                  40                  45

Pro Val Arg Leu Thr Gln Leu Pro Glu Asn Gly Gly Trp Asn Ala Pro
    50                  55                  60

Ile Thr Asp Phe Tyr Phe Gln Gln Cys Asp
65                  70
```

<210> SEQ ID NO 237

```
<211> LENGTH: 30
<212> TYPE: DNA
<213> ORGANISM: Homo sapiens

<400> SEQUENCE: 237
ggcagtggga ctgggggcaa gatactacat                                        30

<210> SEQ ID NO 238
<211> LENGTH: 30
<212> TYPE: DNA
<213> ORGANISM: Homo sapiens

<400> SEQUENCE: 238
aattaaatat gcagaacaac tgctgtgcag                                        30

<210> SEQ ID NO 239
<211> LENGTH: 30
<212> TYPE: DNA
<213> ORGANISM: Homo sapiens

<400> SEQUENCE: 239
gctgtggcct ctccttccct acagctggag                                        30

<210> SEQ ID NO 240
<211> LENGTH: 30
<212> TYPE: DNA
<213> ORGANISM: Homo sapiens

<400> SEQUENCE: 240
agaagatctg catactccct acagctggag                                        30

<210> SEQ ID NO 241
<211> LENGTH: 30
<212> TYPE: DNA
<213> ORGANISM: Homo sapiens

<400> SEQUENCE: 241
gatgtgaaca ttgagttatt gtaaacctct                                        30

<210> SEQ ID NO 242
<211> LENGTH: 11
<212> TYPE: PRT
<213> ORGANISM: Homo sapiens

<400> SEQUENCE: 242

Met Cys Ser Leu Pro Met Ala Arg Tyr Tyr Ile
1               5                   10

<210> SEQ ID NO 243
<211> LENGTH: 29
<212> TYPE: PRT
<213> ORGANISM: Homo sapiens

<400> SEQUENCE: 243

Ile Lys Tyr Ala Asp Gln Lys Ala Leu Tyr Thr Arg Asp Gly Gln Leu
1               5                   10                  15

Leu Val Gly Asp Pro Val Ala Asp Asn Cys Cys Ala Glu
            20                  25

<210> SEQ ID NO 244
<211> LENGTH: 72
<212> TYPE: PRT
<213> ORGANISM: Homo sapiens

<400> SEQUENCE: 244
```

```
Met Ser Ser Ser Phe Leu Pro Glu Pro Leu Ala Lys Ser Leu Gln
1               5                   10                  15

His Gly Val Pro Leu Ser Leu Asp Ser Ser Leu Ser Ser Leu Glu
                20                  25                  30

Lys Ile Cys Ile Leu Pro Asn Arg Gly Leu Ala Arg Thr Lys Val Pro
                35                  40                  45

Ile Phe Leu Gly Ile Gln Gly Gly Ser Arg Cys Leu Ala Cys Val Glu
    50                  55                  60

Thr Glu Glu Gly Leu Gln Leu Glu
65              70
```

<210> SEQ ID NO 245
<211> LENGTH: 40
<212> TYPE: PRT
<213> ORGANISM: Homo sapiens

<400> SEQUENCE: 245

```
Lys Ile Cys Thr Leu Pro Asn Arg Gly Leu Asp Arg Thr Lys Val Pro
1               5                   10                  15

Ile Phe Leu Gly Ile Gln Gly Gly Ser Arg Cys Leu Ala Cys Val Glu
                20                  25                  30

Thr Glu Glu Gly Leu Gln Leu Glu
        35                  40
```

<210> SEQ ID NO 246
<211> LENGTH: 68
<212> TYPE: PRT
<213> ORGANISM: Homo sapiens

<400> SEQUENCE: 246

```
Asp Val Asn Ile Glu Glu Leu Tyr Lys Gly Gly Glu Ala Thr Arg
1               5                   10                  15

Phe Thr Phe Phe Gln Ser Ser Ser Gly Ser Ala Phe Arg Leu Glu Ala
                20                  25                  30

Ala Ala Trp Pro Gly Trp Phe Leu Cys Gly Pro Ala Glu Pro Gln Gln
            35                  40                  45

Pro Val Gln Leu Thr Lys Glu Ser Glu Ala Arg Thr Lys Phe Tyr Phe
    50                  55                  60

Glu Gln Ser Trp
65
```

<210> SEQ ID NO 247
<211> LENGTH: 30
<212> TYPE: DNA
<213> ORGANISM: Homo sapiens

<400> SEQUENCE: 247
gggcagctcc acccttcccc atggctttag                                    30

<210> SEQ ID NO 248
<211> LENGTH: 30
<212> TYPE: DNA
<213> ORGANISM: Homo sapiens

<400> SEQUENCE: 248
ctgacttgta tgaagatgct gactcaaagg                                    30

<210> SEQ ID NO 249
<211> LENGTH: 30
<212> TYPE: DNA

<213> ORGANISM: Homo sapiens

<400> SEQUENCE: 249
gctgcagtca cagaagatgc aagccttcag          30

<210> SEQ ID NO 250
<211> LENGTH: 30
<212> TYPE: DNA
<213> ORGANISM: Homo sapiens

<400> SEQUENCE: 250
agacgatctg ccgacgatgc aagccttcag          30

<210> SEQ ID NO 251
<211> LENGTH: 30
<212> TYPE: DNA
<213> ORGANISM: Homo sapiens

<400> SEQUENCE: 251
aatctgggat gttaaatgtc aatttagaag          30

<210> SEQ ID NO 252
<211> LENGTH: 30
<212> TYPE: DNA
<213> ORGANISM: Homo sapiens

<400> SEQUENCE: 252
aaaagataga tgtggagact ccagctggag          30

<210> SEQ ID NO 253
<211> LENGTH: 30
<212> TYPE: DNA
<213> ORGANISM: Homo sapiens

<400> SEQUENCE: 253
gcagttaaca tcactaatct tgaaaatgcc          30

<210> SEQ ID NO 254
<211> LENGTH: 4
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Glu or Ala

<400> SEQUENCE: 254

Met Ala Leu Xaa
1

<210> SEQ ID NO 255
<211> LENGTH: 21
<212> TYPE: PRT
<213> ORGANISM: Homo sapiens

<400> SEQUENCE: 255

Asp Leu Tyr Glu Glu Gly Gly Gly Gly Gly Gly Glu Gly Glu Asp Asn
1               5                   10                  15

Ala Asp Ser Lys Glu
            20

<210> SEQ ID NO 256
<211> LENGTH: 37
<212> TYPE: PRT
<213> ORGANISM: Homo sapiens

<400> SEQUENCE: 256

Met Glu Ile Cys Arg Gly Leu Arg Ser His Leu Ile Thr Leu Leu Leu
1               5                   10                  15

Phe Leu Phe His Ser Glu Thr Ile Cys Arg Gly Arg Lys Ser Ser Lys
                20                  25                  30

Met Gln Ala Phe Arg
            35

<210> SEQ ID NO 257
<211> LENGTH: 15
<212> TYPE: PRT
<213> ORGANISM: Homo sapiens

<400> SEQUENCE: 257

Thr Ile Cys Arg Gly Arg Lys Ser Ser Lys Met Gln Ala Phe Arg
1               5                   10                  15

<210> SEQ ID NO 258
<211> LENGTH: 30
<212> TYPE: PRT
<213> ORGANISM: Homo sapiens

<400> SEQUENCE: 258

Ile Trp Asp Val Asn Gln Lys Thr Phe Tyr Leu Arg Asn Asn Gln Leu
1               5                   10                  15

Val Ala Gly Tyr Leu Gln Gly Pro Asn Val Asn Leu Glu Glu
                20                  25                  30

<210> SEQ ID NO 259
<211> LENGTH: 37
<212> TYPE: PRT
<213> ORGANISM: Homo sapiens

<400> SEQUENCE: 259

Lys Ile Asp Val Val Pro Ile Glu Pro His Ala Leu Phe Leu Gly Ile
1               5                   10                  15

His Gly Gly Lys Met Cys Leu Ser Cys Val Lys Ser Gly Asp Glu Thr
                20                  25                  30

Arg Leu Gln Leu Glu
            35

<210> SEQ ID NO 260
<211> LENGTH: 71
<212> TYPE: PRT
<213> ORGANISM: Homo sapiens

<400> SEQUENCE: 260

Ala Val Asn Ile Thr Asp Leu Ser Glu Asn Arg Lys Gln Asp Lys Arg
1               5                   10                  15

Phe Ala Phe Ile Arg Ser Asp Ser Gly Pro Thr Thr Ser Phe Glu Ser
                20                  25                  30

Ala Ala Cys Pro Gly Trp Phe Leu Cys Thr Ala Met Glu Ala Asp Gln
            35                  40                  45

Pro Val Ser Leu Thr Asn Met Pro Asp Glu Gly Val Met Val Thr Lys
        50                  55                  60

Phe Tyr Phe Gln Glu Asp Glu
65                  70